United States Patent [19]

Hayden et al.

[11] Patent Number: 5,849,995
[45] Date of Patent: Dec. 15, 1998

[54] MOUSE MODEL FOR HUNTINGTON'S DISEASE AND RELATED DNA SEQUENCES

[75] Inventors: Michael Hayden, Vancouver, Canada; Biaoyang Lin, London, United Kingdom; Jamal Nasir, Vancouver, Canada

[73] Assignee: The University of British Columbia, Vancouver

[21] Appl. No.: 457,273

[22] Filed: Jun. 1, 1995

Related U.S. Application Data

[63] Continuation-in-part of Ser. No. 127,971, Sep. 27, 1993, abandoned.

[51] Int. Cl.$^6$ .............................. C12N 5/00; C12N 15/00; C07H 21/04; A61K 49/00
[52] U.S. Cl. ................. 800/2; 800/DIG. 1; 435/320.1; 536/23.5; 536/24.31; 536/24.33; 424/9.2; 935/9; 935/22
[58] Field of Search .................................. 800/2, DIG. 1; 424/9.2; 435/172.3, 320.1; 536/23.5, 24.31, 24.33; 935/9.22

[56] References Cited

U.S. PATENT DOCUMENTS

| | | | |
|---|---|---|---|
| 5,175,383 | 12/1992 | Leder et al. ................................. | 800/2 |
| 5,175,385 | 12/1992 | Wagner et al. .............................. | 800/2 |

OTHER PUBLICATIONS

J. Dorin et al.; Cystic fibrosis in the mouse by targeted insertional mutagenesis *Nature* 359:211–215 (1992).

J. L. Breslow; Transgenic mouse models of lipoprotein metabolism and atherosclerosis *Proc. Natl. Acad. Sci. U.S.A.* 90:8314–8318 (1993).

Dutch–Belgian Fragile X Consortium; Fmr1 Knockout Mice: A Model to Study Fragile X Mental Retardation *Cell.* 78:23–33 (1994).

V. L. J. Tybulewicz et al.; Neonatal Lethality and Lymphopenia in Mice with a Homozygous Disruption of the c–abl Proto–Oncogene *Cell.* 65:1153–1163 (1991).

E. Lee et al., Mice deficient for Rb are nonviable and show defects in neurogensis and haematopoiesis *Nature* 359:288–294 (1992).

G. L. Merlino; Transgenic animals in biomedical research *FASEB J.* 5:2996–3001 (1991).

M. Barinaga; Knockout Mice Offer First Animal Model for CF *Science* 257:1046–1047 (1992).

J. M. Rommens et al.; "A Transcription Map of the Region Containing the Huntington Disease Gene", *Human Molecular Genetics;* 2 No. 7:901–907 (1993).

A. B. Sachs, "Messenger RNA Degradation in Eukaryotes", *Cell;* 74:413–421.

H. Yasueda et al.; High–Level Direct Expression of Semi––Synthetic Human Interleukin–6 in *Escherichia Coli* and Production of N–Terminus Met–Free Product, *Bio/Technology* 8:1036–1040 (1990).

The Huntington's Disease Collaborative Research Group, A Novel Gene Containing a Trinucleotide Repeat that is Expanded and Unstable on Huntington's Disease Chromosomes, *Cell* 72:971–983 (1993).

*Primary Examiner*—Bruce R. Campell
*Attorney, Agent, or Firm*—Myers Bigel Sibley & Sajovec

[57] ABSTRACT

Isolation, cloning and sequencing of the murine Huntington's Disease gene as well as its transcripts and gene products are provided. A transgenic mouse model for Huntington's Disease exhibits cognitive defects similar to symptoms seen in Huntington's Disease in humans.

20 Claims, 46 Drawing Sheets

```
  1 ggttccgcttctgcctgccgccgcagagcccattcattgccttgctgctaagtggccgcgtagtgcc
  1

121 GGAACCCTGGAAAAGCTGATGAAGGCTTTCGAGTCGCTCAAGTCGTTT[AGCCAGCAGCAG]CAG
  2  G  T  L  E  K  L  M  K  A  F  E  S  L  K  S  F  Q  Q  Q  Q  Q  Q agtaggcttccaagtcttcaggtctgtcccatcgggcagtaagccgtgATG
                                                                              M 202 GCG[CCTCCTCCTCCTCCGCCTCCTCCT]CCTCAACCCCCTCAGCCGCCTCAGGGCAGCCG------              ----CCACCGCCGCAG
 29  A  P  P  P  P  P  P  P  P  P  Q  P  P  Q  P  P  Q  G  Q  P  -  -  -  -  -  -  -  -  -  P  P  P  Q
 42  P        G                                     A        T        T                   L
559 GTGGCT                                                                    A                 L 298 ------GAGGAACCGCTGCACCGACCCAAGAAGAAGGAACTCTCAGCCACCAAGAAAGACCGTGTGAATCAT
 60  -  -  E  E  P  L  H  R  P  K  K  K  E  L  S  A  T  K  K  D  R  V  N  H
 82  -     V  A CCGCCGCCACCACCGCCGCTGCCAGGTCCGGCA
                                            -  -  -  -  -  P  P  P  P  P  P  L  P  G  P  A
                                               P  Q  P  Q  P                    G TGTCTAACAATATGTGAAAACATTGTGGCACAGTCTCTCAGAAATTCTCCA
     C  L  T  I  C  E  N  I  V  A  Q  S  L  R  N  S  P
                                V
```

FIG.2A.

```
                                     G T C A                                                            G
                                     T                                                                                   A
679 GAATTCAGAAACTCTTGGGCATCGCTATGGAACTGTTTCTGCTGTGCAGTAACGATGCGG    AGTCAGATGTCAGAAATGGTGGCTGATGAGTGCCTCAACAAAGTCATCAAAGCTTTGTTG
412                                                                                                                      M
99  E F Q K L L G I A M E L F L L C S N D A                         E S D V R M V A D E C L N K V I K A L L
122                                              D

T    C C G                                                   G
799 GATTCTAATCTCTTCCAAGGCCTACAGTTAGAACTCTATAAGGAAATTAAAAAGAATGGCGCTC    CTCGAAGTTTGCTGCTGCCCTGTGGAGGTTTGCTGAGCTGGCTCACCTGGTTCGACCT
532
139 D S N L P R L Q E L Y K E I K K N G A                              P R S L R A A L W R F A E L A H L V R P
162

A                                C  G G          T                                 C A                  C
919 CAGAAGTGCAGGCCCTTACCTGGTGAATCTTCTTCCATGCCTGACCCGAACAAGCAAAAGAC    CGGAGGAATCAGTTCAGGAGACCTTGGCTGCAGCTGTTGCTGCAGCTGTCCTAAAATTATGGCTTCTTT
652
179 Q K C R P Y L V N L L P C L T R T S K R                          P E E S V Q E T L A A A V P K I M A S F
202
```

FIG. 2B.

```
                                T    A G C        G C              G
1039 
 772 GGCAATTTCGCAAATGACAATGAAATTAAGTTCTCTGTTGAAAGCTTTCATAGCAAATCT
 219  G  N  F  A  N  D  N  E  I  K  V  L  L  K  A  F  I  A  N  L
 242

C    A T      G T A       A
     GAAGTCAAGCTCTCCCACCGTGCGGCGGACAGCAGCCGGCTCAGCCGTGAGCATCTGCCAA
      K  S  S  S  P  T  V  R  R  T  A  A  G  S  A  V  S  I  C  Q
                                    I

C   A A         A  T  GT     A A         G T       CT A C    L
1159 
 892 CATTCTAGGAGGACACAGTACTTCTACAACTGGCTCCTTAATGTCCTCCTAGGTCTGCTG
 259  H  S  R  R  T  Q  Y  F  Y  N  W  L  L  N  V  L  L  G  L  L
 282                                 S

TG C G T A              G       T T C C      CC
     GTTCCCATGGAAGAGCACTCCACTCTCCTGATCCTCGGTGTGTTGCTCACATTGAGG
      V  P  M  E  E  E  H  S  T  L  L  I  L  G  V  L  L  T  L  R
                  V   D

A T G               G                                 G G      C A
1279
1012 TGTCTAGTGCCCTTGCTCCTCCAGCAGCAGCAGGTCAAGGACACAAGTCTAAAGGCAGCTTTGG
 299  C  L  V  P  L  L  Q  Q  Q  V  K  D  T  S  L  K  G  S  F  G
 322  Y

A                 G
     GTGACACGGAAAGAAAATGAAGTCTCCTCCTTCTACAGACAGCAGTTGTCCAGGTTTATGAA
      V  T  R  K  E  M  E  V  S  P  S  T  E  Q  L  V  Q  V  Y  E
                                       A

FIG. 2C.
```

```
                              G    A                  T   C  A  C              GT
         1132 CTGACTTTGCATCATATACTCAGCACCAGAGACCACAATGTGGTGACAGGGCACTGGAGCTCCT
         339   L  T  L  H  H  T  Q  H  Q  D  H  N  V  V  T  G  A  L  E  L  L

AA     G           C  GT          AC         G   GTC    G
         1252 GCAGCAGCTCTTCCGTACCCCTCCACTGAACTCCTGCAGCTCCTGCAAGCACTGACCACACCAGGA
         379   Q  Q  L  F  R  T  P  P  P  E  L  L  Q  A  L  T  T  P  G
                                                           T         A  V

CGCT C A G    G   T  TG T     A      T    T
         1252 GGGCTTGGGCAGCTCACTCTGGTTCAAGAGGCCCGAGGCCGAGGCCGAGGCGGGAGCAT
         379   G  L  G  Q  L  T  L  V  Q  E  E  A  R  G  R  G  R  S  G  S  I
                H            A  K                                  S  G

T   AA                       A                    T       A  A
         1372 CGTGGAGCTTTTAGCTGGAGGGGTTCCTGAGCCCTGTCAGCCCTCCTCAAGAAGCAG
         379   V  E  L  L  A  G  G  G  S  S  C  S  P  V  L  S  R  K  Q
                            H

A                           G    T A G A G
         1372 AAAGGCAAAGTGCTCTTAGGAGAAGAGGAAGCCTTGGAAGATGACTCGAGTCCAGTCAGA
         419   K  G  K  V  L  L  G  E  E  E  A  L  E  D  D  S  E  S  R  S  D

T   AA    A       GA               CA                         G
         1372 TGTCAGCAGCTCAGCTTTGCAGCTCTCTGTGAAGAGTGAGATTGGTGGAGAGCTCGCT
         419   V  S  S  S  A  F  A  A  S  V  K  S  E  I  G  G  E  L  A
                                  L  T        D                     S
```

```
2119    T  A      CA       A   C  A    C  G  G CC      G
1852 GAGGACGATGAGGAGGAGCTGCAGGTGTTCTTTCTGGTGAAGTCTCAGATGTTTCAGA
579   E  D  D  E  E  G  A  A  G  V  L  S  G  E  V  S  D  V  F  R
602   D  E                    T        I  P  D  A  E  A

CA       G    T    A  A  AC    AT   CT
     AACTCTTCTCTGGCCCCTCAACAGACACACTTGTTGGAAAGAATGGGCCATAGCAGGCAG
      N  S  L  A  L  Q  Q  T  H  L  L  E  R  M  G  H  S  R  Q
            M                A              K  N  S  C

2236          T         G T   AT   GTTG    A CA       C GG
1972 CCTTCCGACACAGCAGTATAGATAAGTATGTAACAGAGATGAGGTTGCTGAAGCCAGTGAT
619   P  S  D  S  S  I  D  K  Y  V  T  R  D  E  V  A  E  A  S  D
641                     V        F     L        A  T  P  G

A             C                T       TCC      C
     CCAGAAAGCAAGCCTTGCCCGAATCAAAGGTGACATAGGACACAGCCTAATGATGATGATTCT
      P  E  S  K  P  C  R  I  K  G  D  I  G  Q  P  N  D  D  D  S
      Q        N                                              S  T

2356    A    T   C  C       C                 G        C   A GG    A
2092 GCTCCTCTGGTACATTGTGTCCGTCTTTTATCTGCTTCCTTTTGTTAACTGGTGAAAAG
659   A  P  L  V  H  C  V  R  L  L  S  A  S  F  L  L  T  G  E  K
681                     S                                       G

T TG         G    G  T    G     C
     AAAGCACTGGTTCCAGACAGAGTCAGAGAGTCAGTGAAGCCCTGCCCTCAGCTGC
      K  A  L  V  P  D  R  D  V  R  V  S  V  K  A  L  A  L  S  C
      N  V                                                     T

FIG.2F.
```

```
                  G G  A  A           C   G G A T       A  C T     T
     2476                                                                                                                   
     2212 ATTGGTGCGGGCTGTGGCCCTTCATCCAGAGTCGTTCTTCAGCAGACTGTACAAAGTACCT
     699  I  G  A  A  V  A  L  H  P  E  S  F  F  S  R  L  Y  K  V  P
     721                                                           V                                                K

G C         TACC                                         C A
     2596
     2332 CTTAATACCGGAAAGTACTGAGAACAGTATGTTTCTGACATCTTGAACTACATCGAT
     739  L  N  T  T  E  E  Q  Y  V  S  D  I  L  N  Y  I  D
     761        D                        Y  P

T         C                    CA      G
     2596
     2332 CATGGAGAGACCCACAGGTCCGAGGAGTCCGCATTCCTCTGTGGACCCTTGTCTACTCC
     739  H  G  D  P  Q  V  R  G  A  T  A  I  L  C  G  T  L  V  Y  S
     761                                                    I     C

C      CT  AC  G ATA      C   T        C
     2716
     2452 ATCCTCAGTAGTCCCGTCTCCGTGTTGGTGACTGGCTGGGACTGGCTGGGCAACATCAGAACCCTGACA
     779  I  L  S  R  S  R  L  R  V  G  D  W  L  G  N  I  R  T  L  T
     801                                          F  H           M     T

T  C  T                G     G         AC                 G
     2716
     2452 GGAAATACATTTCTCTGGTGGACTGCATTCCTTTACTGCAGAAAACGTTGAAGGATGAA
     779  G  N  T  F  S  L  V  D  C  I  P  L  L  Q  K  T  L  K  D  E
     801                       A                      R

A                      A      A             C
     2716
     2452 TCTTCTGTTACTTGCAAGTTGGCTTGTACAGTTGGCACTGTGAGGCACTGTCCTGAGTCTTTGC
     779  S  S  V  T  C  K  L  A  C  T  A  V  R  H  C  V  L  S  L  C
     801                                                N           M
```

```
3196                                                                                   T         A           G          T T  C   C
2932 AGTGTCTACCTGAAGCTCCTGATGCATGAGACCCAGCCACCATCACACTTTCTGTCAGC
 939   S  V  Y  L  K  L  L  M  H  E  T  Q  P  P  S  H  F  S  V  S
 961                    T

A      A                A  C      A   C   C                            T
     ACCATCACCAGAATCTATAGAGGCTATAGTCTTACTGCCAAGAATAACAGAGATGTCACCATG
      T  I  T  R  I  Y  R  G  Y  S  L  L  P  R  I  T  D  V  T  M
                                                             S

3316            T  C  T                 A        A          A  C  A                 C   C
3052 GAAAACAATCTCTCAAGAGTTGTGCCGCAGTTTCTCATGAACTCATTACGTCAACAACA
 979   E  N  N  L  S  R  V  V  A  A  V  S  H  E  L  I  T  S  T  T
1001                         I

A A                                        T            T  CA T    C
     CGGGCACTCACATTTGGATGCTGTGAAGCCTTGTGTCTTCTCTCCAGCAGCCTTTCCAGTT
       R  A  L  T  F  G  C  C  E  A  L  C  L  L  S  A  A  F  P  V
                                                                     T

3436        T                                T               A
3172 TGCACTTGGAGTTTAGGATGGCACTGTGGAGTGCCCCACTGAGTGCCTCTGATGAGTCC
1019   C  T  W  S  L  G  W  H  C  G  V  P  P  L  S  A  S  D  E  S
1041        I

T     C                    A       A                          G      C   G   G
     AGGAAGAGCTGCACTGTTGGATGGCCTCCATGATATTCTCACCTTGCTTTCATCAGCTTGG
       R  K  S  C  T  V  G  M  A  S  M  I  L  T  L  L  S  S  A  W
                                                                     T
```

FIG. 21.

```
                                                                        C
                T                       A         T
3556
3292 TTCCACTGGATCTCTCAGCCCATCAGGATGCCTTGATTTGGCTGAAACTTGCTAGCA
1059  F  P  L  D  L  S  A  H  Q  D  A  L  I  L  A  G  N  L  L  A
1081

C      T    A              C
     GCGAGTGCCCCCAAGTCTCTGAGAAGTTCATGGACCTCTGAAGAAGAAGCCAACTCAGCA
     A  S  A  P  K  S  L  R  S  S  W  T  S  E  E  E  A  N  S  A
                                              A                    P

AG   A    GG         G   A  C       C     G    GG    A
3676
3412 GCCACCAGACAGGAGGAAATCTGCCCCTGCTCTGGGGATCGGACTCTAGTGCCCTTGGTG
1099  A  T  R  Q  E  E  I  C  P  A  L  G  D  R  T  L  V  P  L  V
1121              K                    V  W                    A  M

C                T  C    C   C   C   T  C
     GAGCAGCTTTTCTCCCACCTGCTGAAGGTGATCAATATCTGTGCTCATGTCTTGGACGAT
     E  Q  L  F  S  H  L  L  K  V  I  N  I  C  A  H  V  L  D  D

G         C       A
3796
3532 GTGACTCCTGGACCAGCAATCAAGGCAGCCTTGCCTTCTCTAACAAACCCCCCTTCTCTA
1139  V  T  P  G  P  A  I  K  A  A  L  P  S  L  T  N  P  P  S  L
1161  A

G  C        G              A               A    GT A    GT
     AGTCCTATTCGACGGAAAGGAAGGAGAAAGAACCTGGAGAACAAGCTTCTACTCCAATG
     S  P  I  R  R  K  G  K  E  K  E  P  G  E  Q  A  S  T  P  M
                                                             V
```

```
            GCA                          T         T       A           T T A                G
3652 AGTCCCAAGAAAGTTGGTGAGGCCAGTGCAGCCTCTCGACAATCAGACACCTCAGGACCT
1179  S  P  K  K  V  G  E  A  S  A  A  S  R  Q  S  D  T  S  G  P
         G  S

T       A     C    A                       T   T  A
3772 GTCACAGCAAGTAAATCATCCTCACTGGGGAGTTTCTACCATCCCCTCCTACCTCAAA
1219  V  T  A  S  K  S  S  S  L  G  S  F  Y  H  L  P  S  Y  L  K
                                                                  R

T A         T   C             GC G                  A
3772 CTGCATGATGTCCTGAAAGCCACTCACGCCAACTATAAGGTCACCTTAGATCTTCAGAAC
1219  L  H  D  V  L  K  A  T  H  A  N  Y  K  V  T  L  D  L  Q  N
                                                               T

CG          A  TC  A                T  T        A
3892 AGCAATGAAAAGTTTGGGGGTTCCTGCGCTTGGACGTCCTTTCTCAGATTCTA
1259  S  N  E  K  F  G  G  F  L  R  S  A  L  D  V  L  S  Q  I  L
                                                              T

C                   G                A        A            T      T A AT G
3892 GAGCTGGCGACACTGCAGGACATTGGAAGTGTGTTGAAGAGTCCTTGGATACCTGAAA
1259  E  L  A  T  L  Q  D  I  G  K  C  V  E  E  V  L  G  Y  L  K
                                                      I

4156 TCCTGCTTTAGTCGAGAACCAATGATGGCAACTGTCTGTGCAGCTATTGAAGACT
1259  S  C  F  S  R  E  P  M  M  A  T  V  C  V  Q  Q  L  L  K  T
```

FIG. 2L.

```
                                            T
          G   G   G   A                                                 A
4372 ACAACATCTGTACAATTGCAGAAGCAGGTTTTGGATTGCTGGCACAGCTGGTTCAGCTA
1419  T   T   S   V   Q   L   Q   K   Q   V   L   D   L   L   A   Q   L   V   Q   L
1441
                                                                                        T   T   C        AT    A
                    T                                                     C
     CGGGTCAATTACTGTCTACTGGATTCAGACCAGTTGTTCATCGGTTTGTGCTGAAGCAG
4492  R   V   N   Y   C   L   L   D   S   D   Q   V   F   I   G   F   V   L   K   Q
1459
1481
                    A                           C           C   C
4492 TTTGAGTACATTGAAGTGGGCCAGTTCAGGGAATCAGAGGCAATTATTCCAAATATATTT
1459  F   E   Y   I   E   V   G   Q   F   R   E   S   E   A   I   I   P   N   I   F
1481
                          T           A   A                 T
     TTCTTCCTGGTATTACTGTCTTATGAGCGTACCATTCAAAACAGATCATTGGAATTCCT
1459  F   F   L   V   L   L   S   Y   E   R   Y   H   S   K   Q   I   I   G   I   P
                          T               G                                  C
4612 AAAATCATCCAGCTGTGTGATGGCATCATGGCCAGTGGAAGGAAGGCCGTTACACATGCT
1499  K   I   I   Q   L   C   D   G   I   M   A   S   G   R   K   A   V   T   H   A
1521
                                        G                   A         C        A
     ATACCTGCTCTGCAGCCCATTGTCCATGACCTCTTTGTGTTACGAGGAACAAATAAAGCT
1499  I   P   A   L   Q   P   I   V   H   D   L   F   V   L   R   G   T   N   K   A
1521
```

```
                                              G    G      GC    T   C C G  T
5716                                                                                              
5449 GCCACTAGACTCTTCACCAGTGATGGCTGTGAAGGCAGCTTCTATACTCTAGAGAGCCT
1778  A  T  R  L  F  T  S  D  G  C  E  G  S  F  Y  T  L  E  S  L
1801                                    G                    D

CTTG     CT T      A CA    C      G       G
5836                                                                                              
5569 GAATGCACGGGTCCGATCCATGGTGCCACGGCCCAGCCCTGGTACTGCTCTGGTGTCAG
1818  N  A  R  V  R  S  M  V  P  T  H  P  A  L  V  L  L  W  C  Q
1841           L         A         I  T

A   G  G  TG             C        C       A                C
5836                                                                                              
5569 ATCCTACTTCTCATCAACCACACTGACTACCGGTGGTGGGCAGAGGTGCAGCAGACACC
1818  I  L  L  I  N  H  T  D  Y  R  W  W  A  E  V  Q  Q  T  P
1841              V

G  A            A     A     A       T    GT     A

CAAGAGACACAGTCTGTCCTGCACGAAGTCACTTAACCCCAGAAGTCTGGCGAAGAGAG
      K  R  H  S  L  S  C  T  K  S  L  N  P  Q  K  S  G  E  E  E
                        S              L        M

A   T       CA A                                   A    A

GATTCTGGCTGCCAGCTCAGCTGGAATGTGCAATAGAGAAATAGTGCGGAGAGGGC
      D  S  G  S  A  A  Q  L  G  M  C  N  R  E  I  V  R  R  G  A
                          D  L                    K

T  C                                          C           G   G

CCTTATTCTCTTCTGTGATTATGTCTGTCAGAATCTCCATGACTCAGAATACTTAACATGG
      L  I  L  F  C  D  Y  V  C  Q  N  L  H  D  S  E  H  L  T  W
```

FIG. 2P.

```
              A                     C T  C   C                          G
6076  CTCATTGTGAATCACATTCAAGATCTGATCAGCTTGTCTCTCATGAGCCTCCAGTACAAGAC
5809  CTCATTGTGAATCACATTCAAGATCTGATCAGCTTGTCTCTCATGAGCCTCCAGTACAAGAC
1898   L  I  V  N  H  I  Q  D  L  I  S  L  S  H  E  P  P  V  Q  D
1921

C              G   G  C  T C C G G  C                    G
      TTTATTAGTGCCATTCATCGTAATTCTGCAGCTAGTGGTCTTTTTATCCAGGCAATTCAG
       F  I  S  A  I  H  R  N  S  A  A  S  G  L  F  I  Q  A  I  Q
                         V

T           TG             T                        G       A             G  G              T           T
6196  TCTCGCTGCTGTGAAAATCTTTCAACGCCAACCACTCTGAAGAAAAACACTTCAGTGCTTGAA
5929  TCTCGCTGCTGTGAAAATCTTTCAACGCCAACCACTCTGAAGAAAAACACTTCAGTGCTTGAA
1938   S  R  C  E  N  L  S  T  P  T  T  L  K  K  T  L  Q  C  L  E
1961                                    M

G         A                                                              G                        T
      GGCATCCATCTCAGCCAGTCTGGGCTGTGCTCACACTATATGTGGACAGGCTCCTGGGC
       G  I  H  L  S  Q  S  G  A  V  L  T  L  Y  V  D  R  L  L  G

C T T              T                                       T     T   T                                                   T
6316  ACCTCCTCCCGTGGCTCGCTGGCTCGACATGGTCGACACCCTGGCCTGTCGCCGGGTAGAAATG
6049  ACCTCCTCCCGTGGCTCGCTGGCTCGACATGGTCGACACCCTGGCCTGTCGCCGGGTAGAAATG
1978   T  S  S  R  A  L  A  R  M  V  D  T  L  A  C  R  R  V  E  M
2001         P  F           V                        I

C                             AT    A    C                                                                       
      CTTTTGGCTGCAAATTTACAGAGCAGCATGGCCCAGTTGCCAGAGGAGAACTAAACAGA
       L  L  A  A  N  L  Q  S  S  M  A  Q  L  P  E  E  E  L  N  R
                                M
```

FIG. 2Q.

```
6436                           G       T   G    C    C  T  G
6169 ATCCAAGAACACCTCCAGAACAGTGGGCTTGCACAAAGACACCAAAGGCTCTATTCACTG
2018  I  Q  E  H  L  Q  N  S  G  L  A  Q  R  H  Q  R  L  Y  S  L
2041           Y                S
                                 G T   C  CA    A                          T    CT   T
     CTGGACAGATTCCGACTCTCTACTGTGCAGGAGACTCCACTTAGCCCCTTGCCCCAGTCACT
      L  D  R  F  R  L  S  T  V  Q  D  S  L  S  P  L  P  P  V  T
                                M                                S

6556     G         AC      GTG A                       G
6289 TCCCACCCACTGGGTCGGGATGGGCACACATCTCTGGAAACAGTGAGTCCAGACAAAGAC
2058  S  H  P  L  G  G  D  G  H  T  S  L  E  T  V  S  P  D  K  D
2081              D         V
            G T       A                                        G
     TGGTACCTCCAGTTGTGTCAGATCCCAGTGTTGGACCAGATCAGATTCTGCACTGCTGAA
      W  Y  L  Q  L  V  R  S  Q  C  W  T  R  S  D  S  A  L  L  E
                      K       V  H

6676      G T G T                          C              A
6409 GGTGCAGAGCTGGTCAACCGTATCCCTGCTGAAGATATGAATGACTTCATGATGAGCTCG
2098  G  A  E  L  V  N  R  I  P  A  E  D  M  N  D  F  M  M  S  S
2121                                              A           N
               GC A    C          A          G      T    GG
     GAGTTCAACCTAAGCCTTTTGGCTCCCTGTTTAAGCCTTGGCATGAGCGAGATTGCTAAT
      E  F  N  L  S  L  L  A  P  C  L  S  L  G  M  S  E  I  A  N
                                                              S  G
```

```
7156          G           G G G         A C  G C       A
6889 CTAGACTGCTGCTGCCTGGCACTACAGGTGCCTGGCCTCTGGGGGTGCTGTCCTCCCAGA
2258    L  D  C  C  C  L  A  L  Q  V  P  G  L  W  G  V  L  S  S  P  E
2281                                       S              V           T

TT  C C         TC      AC                    G
     GTACGTGACTGATGCCTGCTCCCTCATCCATTGTGTGCGATTCATCCTGGAAGCCATT
     Y  V  T  H  A  C  S  L  I  H  C  V  R  F  I  L  E  A  I
                     F        Y                                   V

7276       G G           G        TA   A   A A    C      A
7009 GCAGTACAACCTGGAGACCAGCTTCTCGGTCCTGAAAGCAGTCACATACTCCAAGAGC
2298    A  V  Q  P  G  D  Q  L  L  G  P  E  S  R  S  H  T  P  R  A
2321                   E                    S           R  T  N     K

GA   CG        GAGGAG          TC  A C C    G  T C T  AGT  A   G A
     TGTCAGAAGGAG-----GAAGTAGACTCAGATATACAAAACCTCAGTCATGTCACTTCG
     V  R  K  E  -  -  E  V  D  S  D  I  Q  N  L  S  H  V  T  S
     I  S  E           E  E                P  N  T        P  K  Y  I     A

7396        T           A        G T            G T                  T T
7123 GCCTGCGAGATGGTGGCAGACATGGTGGAATCCCTGCAGTCAGTGCTGGCCTTGGCCAC
2336    A  C  E  M  V  A  D  M  V  E  S  L  Q  S  V  L  A  L  G  H
2361                                         E

A   T       GG    G GG      GC AT   C G      CA  C        G
     AAGAGGAACAGCACCCTGCCTTCATTTCTCACAGCTGTGAAGAACATTGTTATCAGT
     K  R  N  S  T  L  P  S  F  L  T  A  V  L  K  N  I  V  I  S
                                    G V      A        P L R

FIG.2T.
```

```
                  G  G    T  C       C  A        G       CA        G  T
             7516                                                                                        
             7243 CTGGCCCGACTCCCCCTAGTTAACACAGCTATACTCGTGCCTCCTGGTATGGAAACTC
             2376  L  A  R  L  P  L  V  N  S  Y  T  R  V  P  P  L  V  W  K  L
             2401

A         G       C        G  T
             7636
             7363 GGTGGTCACCCAAGCCTGGAGGGGATTTTGGGACACAGTGTTTCCTGAGATCCCTGTAGAG
             2416  G  W  S  P  K  P  G  G  D  F  G  T  V  F  P  E  I  P  V  E
             2441                                               A

A     AG TT           A       C
             7636
             7363 TTCCTCCAGGAGAAGGAGATCCTCAAGGAGTTCATCTACCGCATCAACACCCTAGGGTGG
             2416  F  L  Q  E  K  E  I  L  K  E  F  I  Y  R  I  N  T  L  G  W
             2441        V                F

G     T  T                                     G

ACCAATCGTACCCAGTTCGAAGAAACTTGGGCCACCCTCCTTGGTGTCCTGGTGACTCAG
                   T  N  R  T  Q  F  E  E  T  W  A  T  L  L  G  V  L  V  T  Q
                             S

C        G              A             G  G
             7756
             7483 CCCCTGGTGATGGAACAGGAAGAGAGCCCACCAGAAGAAGACACAGAAAGAACCCAGAT
             2456  P  L  V  M  E  Q  E  E  S  P  P  E  E  D  T  E  R  T  Q  I
             2481

A  C                    C                    A  G                    T
                  CCATGTCCTGGCTGTGCAGGCCATCACCTCTAGTGCTCAGTCAATGACCGTGCCTGTG
                   H  V  L  A  V  Q  A  I  T  S  L  V  L  S  A  M  T  V  P  V
                             N

FIG. 2U.
```

```
7876          C            G                  T   A                                        G G G  T
7603 GCTGGCAATCCAGCTGTAAGCTGCTTGGAGCAACAGCCCCGAACAGCCACTGAAGGCT
2496  A  G  N  P  A  V  S  C  L  E  Q  Q  P  R  N  K  P  L  K  A
2521

C     G G G              T
     CTCGATACCAGATTTGAAGAAAGCTGAGCATGATCAGAGGGATTGTAGAACAAGAAATC
      L  D  T  R  F  G  R  K  L  S  M  I  R  G  I  V  E  Q  E  I
                                       I

7996          CA              T   C  T      TAT T    A
7723 CAAGAGATGGTTTCCCAGAGAGAATACTGCCACTCACCATTCTCCACCAGGCGTGGAT
2536  Q  E  M  V  S  Q  R  E  N  T  A  T  H  H  S  H  Q  A  W  D
2561       A                                  I            L  Y

CT G              C  C G G G
     CCTGTCCCTTCTCTGTTACCAGCTACTACAGGTCTGCTCTTATCAACCATGACAAGCTGCTG
      P  V  P  S  L  P  A  T  T  G  A  L  I  N  H  D  K  L  L
                  S                                     S        E

8116       A             C                TG  G G               A  C
7843 CTGCAGATCAACCCAGAGAGCGGAGCCAACATGAGTACAAGCTGGGCCAGTGTCCA
2576  L  Q  I  N  P  E  R  E  P  G  N  M  S  Y  K  L  G  Q  V  S
2601                         L                S

G C G                           G
     TACACTCCGTGTGGCTGGGAAATAACATCACACCCCTGAGAGAGGAGAATGGGATGAG
      I  H  S  V  W  L  G  N  N  I  T  P  L  R  E  E  E  W  D  E
                           S
```

FIG. 2V.

```
        8236                  C            G      GGCC   C  C          FF                  CAC
        7963 GAAGAAGAGGAAGAAAGTGATGTCCCTGCACCAACGTCACCACCTGTCTCCAGTCAAT
        2616  E  E  E  E  E  S  D  V  P  A  P  T  S  P  P  V  S  P  V  N
        2641                  A                  A      S                   T
                                                                                         T         G
        TCCAGAAAACCGTGCCGGGGTTGATATTCACTCCTGTCCAGTTTCTGCTTGAATTG
         S  R  K  H  R  A  G  V  D  I  H  S  C  S  Q  F  L  L  E  L

8356               C                                G       G    C
        8083 TACAGCCGATGGATCCTGCCATCCAGTGCAGCCAGAAGGACCCCGTCATCCTGATCAGT
        2656  Y  S  R  W  I  L  P  S  S  A  A  R  R  T  P  V  I  L  I  S
        2681                                                  A

G      CA   C    A   G G              G        G C A           G
        GAAGTGGTTCGATCTCTTCTTGTAGTGTCAGACTTATTCACCGAACGTACCCAGTTTGAA
         E  V  V  R  S  L  L  V  V  S  D  L  F  T  E  R  T  Q  F  E
                                                                      N

8476  C                 G                          G A G                       C
        8203 ATGATGTATCTGACGCTGACAGAACTACGGAGAGTGCACCCTTCAGAAGATGAGATCCTC
        2696  M  M  Y  L  T  L  T  E  L  R  R  V  H  P  S  E  D  E  I  L
        2721  V

GC               C                 G          GG C
        ATTCAGTACCTGGTGCCTGCCACCTGTAAGGCAGCTGCTGTCCTTGGAATGGACAAAACT
         I  Q  Y  L  V  P  A  T  C  K  A  A  A  V  L  G  M  D  K  T
                                                                        A

FIG. 2W.
```

```
                                        AG
8596                G          G   G    GC   C
8323 GTGGCAGAGCCAGTCAGCCGCCTACTGGAGAGCAGCCACCTGCCCAGCCA
2736  V  A  E  P  V  S  R  L  L  E  S  T  L  R  S  S  H  L  P  S  Q
2761                                                             R

GT                    C              C     C      GC    C
8716 GATCGGAGCCCTGCACGGCATCCTCTATGTGTTGGAGTGTGACCTTCTTGATGACACT
8443
2776  I  G  A  L  H  G  I  L  Y  V  V  L  E  C  D  L  L  D  D  T
2801  V

C   C G CA C      C       C         C  A C          G  T
8716 GCAAAGCAGCTCATTCCAGTTGTTAGTGACTATCTGTTCCAACTTCAAAGGAATAGCC
8443
2776  A  K  Q  L  I  P  V  V  S  D  Y  L  L  S  N  L  K  G  I  A
2801                                                I

C   T G        C  A GG                           G  G
8836 CACTGCCGTGAACATTCACAGCCAGCAGCATGTGCTGGTAATGTGTGCCACTGCTTTCTAC
8563
2816  H  C  V  N  I  H  S  Q  Q  H  V  L  V  M  C  A  T  A  F  Y

AA A
8836 CTGATGGAAAACTACCCTCTGGATGTGGGACCAGAATTTTCAGCATCTGTGATACAGATG
8563
2816  L  M  E  N  Y  P  L  D  V  G  P  E  F  S  A  S  V  I  Q  M
2841                                                I

G G
     TGTGGAGTAATGCTGTCTGGAAGTGAGGAGTCCACCCCCTCATCATTTACCACTGTGCC
      C  G  V  M  L  S  G  S  E  E  S  T  P  S  I  I  Y  H  C  A

FIG. 2X.
```

```
8956              A A   C       C         A         C   C C G  TG     A  G              G T
8683 CTCCGGGTCTGGAGCGGCTCCTGCTGTCTGTGCAGCTATCTCGTCTAGACACAGAGTCCCT
2856  L  R  G  L  E  R  L  L  L  S  V  Q  L  S  R  L  D  T  E  S  L
2881                      E                                A

T  G       A            C  G         G     G    G
GGGCAAGTCTAAGTGTGGGAGAGTGAATGTACACAGCCCACACAGGCCATGGCCAGCC
 G  K  L  S  V  G  R  V  N  V  H  S  P  H  R  A  M  A  A
        V          D

9076      G                  T            G   T
8803 CTAGGCCTGATGCTCACCTGCATGTACACAGGAAAAGCCAGTCCAGGCAGAACT
2896  L  G  L  M  L  T  C  M  Y  T  G  K  E  K  A  S  P  G  R  T
2921                                              V

A   T AT    AG C       A                 T         G A
TCTGACCCCAGCCTCTACACCTGACAGCGAGTCTGTGATTGTAGCTATGGAGCGAGTG
 S  D  P  S  P  A  T  P  D  S  E  S  V  I  V  A  M  E  R  V
           N                  A

9196                     T            AG A C           T      A G  C
8923 TCTGTTCTTCTTTGATAGGATCCGCAAGGGATTCCCTGTGAAGCCAGGTTGTGGCAAGGAT
2936  S  V  L  F  D  R  I  R  K  G  F  P  C  E  A  R  V  V  A  R  I
2961

C    T     C                  C    C      G  CA                  C
CCTGCTCAGTTCCTAGATGACTTCTTTCCACCTCAAGATGTCATGAACAAAGTCATT
 L  P  Q  F  L  D  D  F  F  P  P  Q  D  V  M  N  K  V  I
                                                        I

FIG. 2Y.
```

```
                                                                    C G G T
                                                  C
9316                                                                                          
9043 GGAGAGTTCCTGTCCAATCAGCAGCCATACCACAGTTCATGGCCACTGTAGTTTACAAG
2976 
3001 G E F L S N Q Q P Y P Q F M A T V V Y K

G                    CA C        G
9436
9163 GTTTTCAGACTTGCACAGTGGGCAGTCATCATCATGTCCGGGACTGGGTCATGCTG
2976
3001 V F Q T L H S A G Q S S M V R D W V M L
                                 T

C          G  G GG C C                           C
9436                                                                   
9163 TCCCTGTCCAACTTCACACAAGAACTCCAGTTGCCATGTGGAGCCTCTCCTGC
3016 S L S N F T Q R T P V A M M W S L S C
                           A       T

T       C  C  GG       GG  C
9436
9163 TTCCTTGTTAGCGCATCTACCAGCCCATGGGTTTCTGCCATCTTCCACATGTCATCAGC
3056 F L V S A S T S P W V S A I L P H V I S
                           F                        A

G AGG         C                                C
9556
9283 AGGATGGGCAAGCTGGAACTAATGGATGTGAACCTTTTCTGCCTTGTGCCACAGACTTC
3056 R M G K L E L M D V N L F C L V A T D F
                    Q V

GC              C                 C         T
                                                                      E   E
9556                                                                L   E
9283 TACAGACACCAGATAGAGGAGTTCGACCGGAGGGCTTTCCAGTCTGTGTTTGAGGAG
3056 Y R H Q I E E F D R R A F Q S V F E E V
                    L

```
                                           a                          t    ggcagtgg
9898  ccatg
9718  -----tggcaggagtgctttgcaatgagggctatgcaggaacatgcactatgt-------- ggageagct      gcacccatgt                     g                          t
9988
9781  --------gtgcta---------ggttgaccaggtgtttgtcttttcctagtgttcccc gaggccttccagaaagca
      ccaggcaggagtgtctgcagtcctgg    c
                                                 -----tgggggttgagccta---------
                          acctgctggttgtt                         t    t  c   c    gc
      tggccatagtc------------------gccaggttgcagctgccctggtatgtggatcag cc   c    ag  c       ttg    ct    gt   tgcagtagaaggtg
10089
9868  aagtcctagctcttgccagatggttctg--agcccgcctgct--cc---------- g   cc          tg       tgcc    cc     c
10191 ggtgt
9948  -----gcatacctgccacacca-gtgtctgga--cacaaatga---atgg--tgtg-t g
      ccgtgagcaggctttggaac            c     t    g     c   c   c
      --------------------actgggctggagag-ctccctcccacattaccagtag c
         ccagt                    t   a  a  c            g      c    c   cc
      ggg----ggctgggaactgggct-gccaggtgtccagcaccatttccttctgtgtt c
10295
10047 ttctttctcaggagttaaatttaattatatcagtaaagagattaatttaatgtaaaaa
```

FIG. 2B'

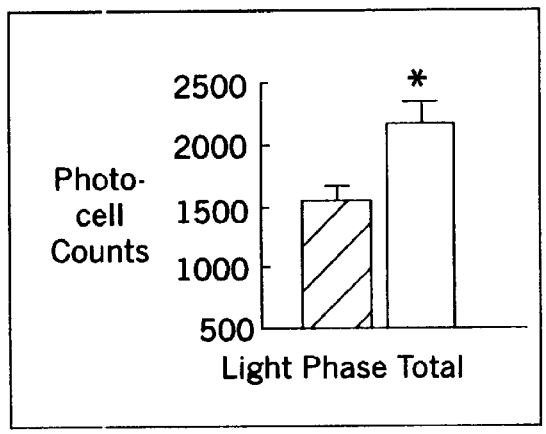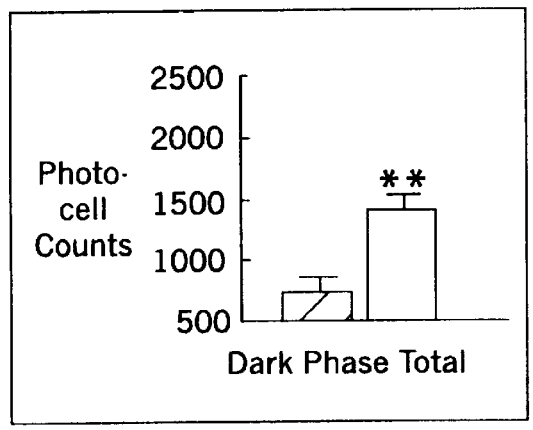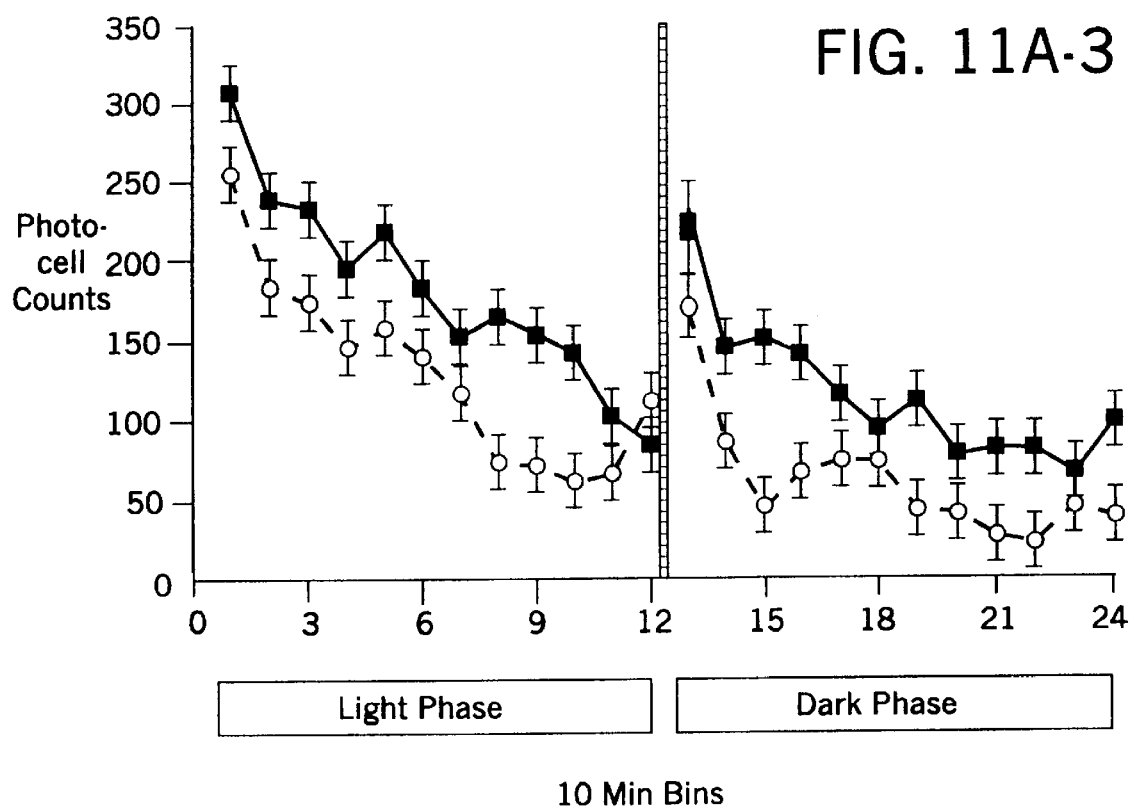

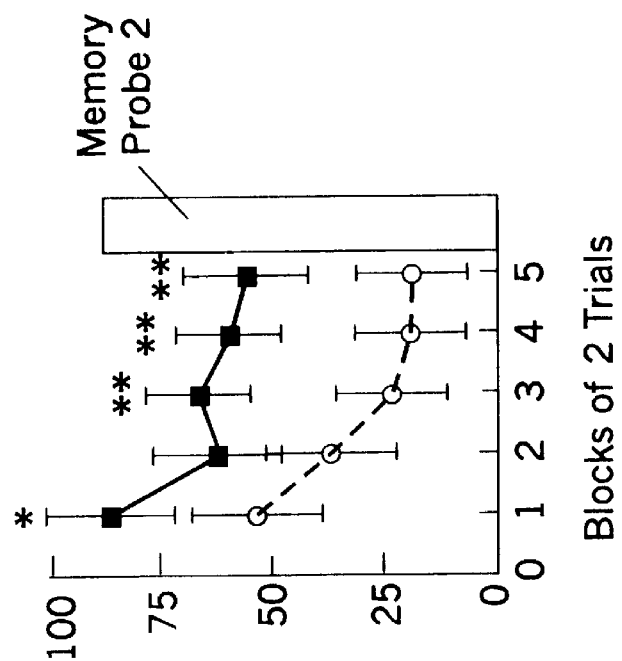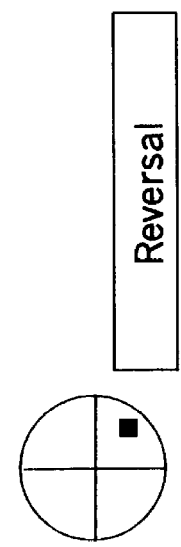
FIG. 11B-1
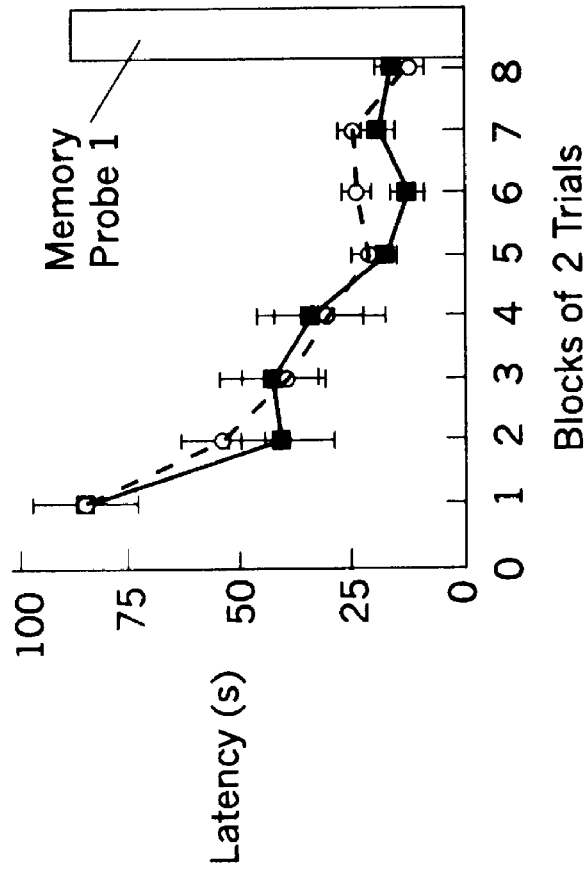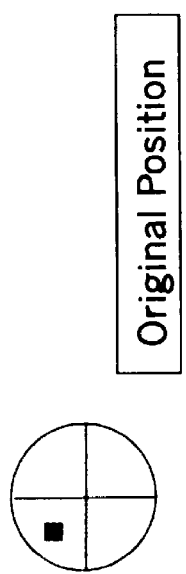
FIG. 11B-2

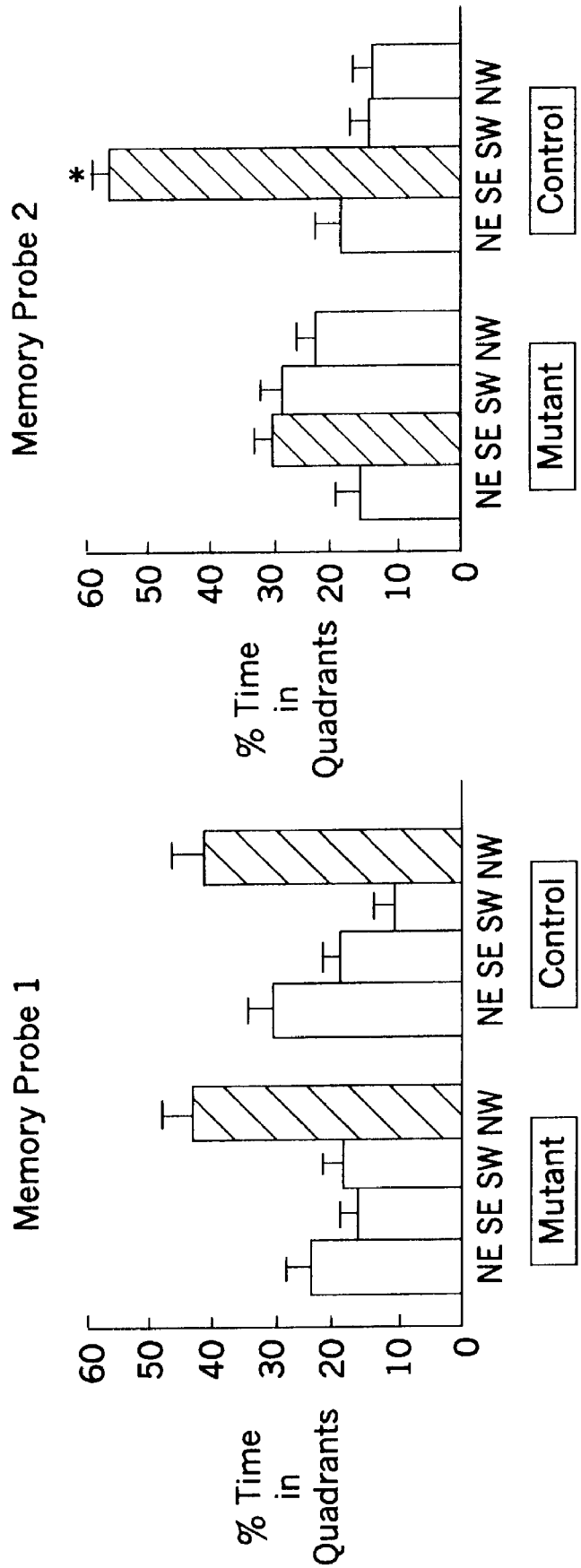

MOUSE MODEL FOR HUNTINGTON'S DISEASE AND RELATED DNA SEQUENCES

RELATED APPLICATIONS

This is a Continuation-In-Part of U.S. application Ser. No. 08/127,971 filed Sep. 27, 1993, abandoned, which is incorporated by reference herein in its entirety.

FIELD OF INVENTION

This invention relates to the Huntington's Disease gene, to the isolation, cloning and sequencing of the murine HD gene as well as its transcripts and gene products and more particularly the present invention relates to a transgenic mouse model for HD which exhibits cognitive defects similar to those of Huntington's Disease and can be used to develop therapeutic strategies to treat the disease and provide for drug screening to alleviate symptoms of the disease.

BACKGROUND OF THE INVENTION

HD (Huntington's Disease) is a devastating neurological disease which usually presents in mid adult life, affects approximately 1 in 10,000 individuals (Hayden 1981), and results in psychiatric disturbance, involuntary movement disorder, and cognitive decline associated with inexorable progression to death, typically 17 years following onset. Recently, it has been reported that HD is associated with expansion of a CAG repeat within a novel gene, Canadian application Serial No. 2,092,455 filed Mar. 25, 1993. The HD gene is ubiquitously expressed (Strong et al. 1993; Li et al., 1993) and conserved across a wide range of species (Lin et al., 1994). Structural analysis of its promoter region is consistent with it being a housekeeping gene (Lin et al., 1995). The HD gene encompasses 67 exons, spans over 200 kb (Ambrose et al., 1994) and is associated with two transcripts of 10.3 kb and 13.6 kb, differing with respect to their 3' untranslated regions (Lin et al., 1993). Both messages are predicted to encode a 348 kilodalton protein containing 3144 amino acids. In addition, the HD gene encompasses a highly polymorphic CAG repeat which varies in number from 8 to 35 in normal individuals (Kremer et al., 1994). CAG expansion beyond 36 CAG repeats is seen in persons with HD.

The increase in size of the CAG repeat in persons with HD shows a highly significant correlation with age of onset of clinical features. This association is particularly striking for persons with juvenile onset HD who have very significant expansion, usually beyond 50 repeats. The CAG repeat length in HD families does exhibit some instability that is particularly marked when children inherit the HD gene from affected fathers.

HD is one of an increasing number of disorders associated with trinucleotide repeat expansion, including myotonic dystrophy, fragile X syndrome, spinobulbar muscular atrophy (SBMA) and more recently spinocerebellar ataxia type 1 and X linked mental retardation. The common occurrence of the expanded trinucleotide repeat in each of these disorders suggests a common feature underlying their pathogenesis. There are however, still few clues as to how repeat expansion actually causes these illnesses. In HD, it is not known how this gene that is widely expressed results in selective neuronal death. Further, sequence analysis revealed no obvious homology to other known genes and no structural motifs or functional domains were identified which clearly provide insights into its function. In particular, the question of how these widely expressed genes cause selective neuronal death remains unanswered.

In order to address this issue, we have investigated whether or not an animal might carry a similar gene. We have discovered that there is a murine hd gene and that an animal model for HD can be developed which exhibits symptoms similar to those in human HD patients. The animal model allows for the study of the function of this gene and its product during growth and development and also will provide insights into the molecular pathogenesis of this disease, and assessing the efficacy of therapeutic compounds directed to treating the symptoms of the disease.

Here we present the cloning, sequencing and analysis of the murine hd cDNA. The CAG repeat is conserved, and is likely to be contained within the coding region of the gene. The adjacent CCGs are also conserved and the length of the CCG triplet is polymorphic in the mouse.

SUMMARY OF THE INVENTION

Many aspects of the invention may be used to develop information regarding HD. Identification of the mouse gene is very important in the construction of the mouse model for HD, in order to provide insights into the molecular pathogenesis of the disease and devise therapeutic strategies to control the symptoms. The sequencing of cDNA clones spanning 10,105 nucleotides, encoding the murine HD homolog (mhd), exhibits 90% peptide sequence identity, including conservation of CAG and adjacent CCG repeats. With the identification and the sequencing of the gene and the gene product, nucleic acid probes and antibodies raised to the gene product can be used in a variety of hybridization and immunological assays to screen for and detect the presence of either a normal or defective HD gene or gene product in mice.

According to an aspect of the invention, a purified DNA molecule consists essentially of a DNA sequence which corresponds to the DNA sequence depicted in SEQ ID NO:7.

According to another aspect of the invention is a transgenic mouse exhibiting symptoms similar to Huntington's Disease and having a trinucleotide CAG repeat expansion in excess of 35 in the translated coding region commencing at nucleic acid 169 of the murine nucleotide sequence.

According to another aspect of the invention a transgenic mouse whose cells contain a modified nucleotide sequence depicted by SEQ ID NO:7, said nucleotide sequence being modified by gene targeting to introduce a targeting vector within an exon.

According to another aspect of the invention is a transgenic mouse exhibiting symptoms similar to HD, as well as morphological and histological brain abnormalities also associated with HD.

According to another aspect of the invention is a recombinant targeting vector containing the neomycin resistance gene.

According to another aspect of the invention is a method for screening a drug to determine its effects on relieving symptoms of HD, the method comprising:

(i) assessing behavioral defects in heterozygous HD transgenic mice by conventional behavioral tests including motor activity testing, T-maze alteration test, radial-arm maze test, and Morris water maze task, (ii) administering a drug to these mice, (iii) reassessing behavior in said heterozygous HD mice by conventional behavioral tests including motor activity testing, T-maze alteration test, radial-arm maze test, and Morris water maze task, (iv) comparing the improvement in the behavior test to evaluate the efficacy of said drug.

According to another aspect of the invention is a method for assessing the effects of different drugs on the structure of the brain particularly the basal ganglia, the method comprising:

(i) administering a drug to heterozygous HD mice exhibiting cognitive and behavioral defects;

ii) sacrificing these mice and assessing by histological and morphological methods the effects on the brain, and particularly the basal ganglia.

BRIEF DESCRIPTION OF THE DRAWINGS

FIG. 11A depicts locomotion activity (mean±SEM) as measured by photocell beam breaks for Hdh$^{-ex5}$ knockout mice (black squares) and controls (white circles) during the light and dark phases of the 4 hour testing session.

FIG. 11B depicts the results of Morris Water Maze Testing. Latencies to find the hidden platform (mean±SEM) for Hdh$^{-ex5}$ mice (black squares) and controls (white circles) with the platform in the original position (left) and during the reversal (right) when the platform was moved to the opposite quadrant.

FIG. 11C shows the percentage of time spent in the 4 quadrants of the water maze during memory probe trial 1 (left) and 2 (right), given after the initial acquisition and reversal phases, respectively.

DETAILED DESCRIPTION OF THE PREFERRED EMBODIMENTS

Various aspects of the invention will now be described in respect of how to isolate and clone murine cDNA which has a sufficient degree of homology with the human gene encoding the Huntington Disease protein. Once cloned, various aspects of the murine gene are investigated to establish similarities with the human gene. In accordance with other aspects, various techniques and uses are described for gene products including nucleotide sequence probes, primers are described as well as vectors for use in targeting cells to contain an HD mutant gene, to provide for gene therapy and to provide for gene modification in developing transgenic mice.

A significant commercial aspect of this invention is the development of a mouse model. A variety of techniques may be employed to develop a mouse model which is very useful in clinically evaluating the disease, developing gene therapy techniques, and most importantly drug screening.

To gain insights into the physiological role of the HD gene during growth and development, we have generated both homozygous and heterozygous mice for a targeted disruption of the HD gene. We have demonstrated that homozygous mice with this disruption do not survive to term and suffer early post-implantation embryonic lethality. However, heterozygous mice with this mutation survive and through behavior testing together with histological and morphological examination, we have demonstrated that they exhibit various cognitive deficits and increased motor activity associated with neuronal loss in the subthalamic nucleus of the basal ganglia. These are similar to those symptoms exhibited by human HD patients.

Identification of the Mouse hd cDNA

Figures 2, 11D:
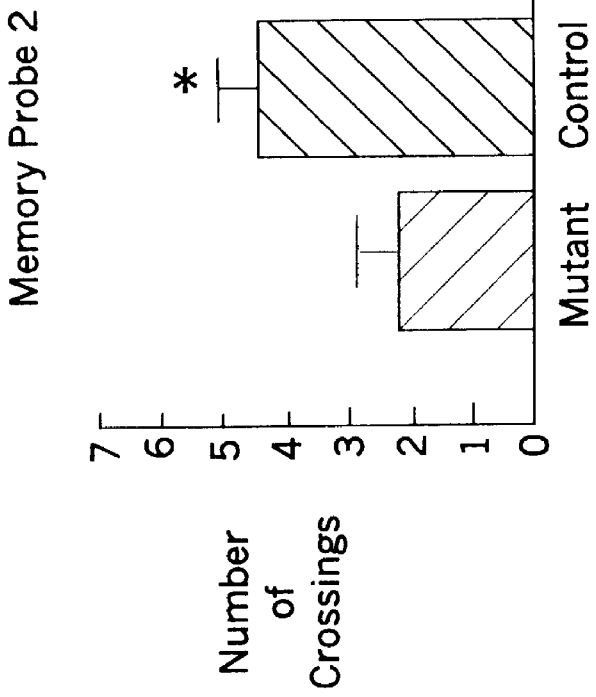
FIG. 2 shows the alignment of mouse and human nucleotide and amino acid sequences; mouse and human HD cDNA (SEQ ID NO:41) and the predicted protein sequence (SEQ ID NO:42) are shown. Non-coding regions are shown in lower case. The mouse nucleic (SEQ ID NO:7) and amino acid (SEQ ID NO:8) sequences are shown in their entirety, whereas only the differences are indicated for human sequences. Gaps are represented by hyphens. The ATG start codon is underlined. The human nucleotide sequence (SEQ ID NO:41) is numbered as in the GenBank entry for HUMTRINUC, accession number L12392. Shaded areas highlighted i) the shared 7×CAG repeat between mouse and human (nucleotide positions 529, 1714, and 4023 in mhd and iv) the putative polyadenylation signal from nucleotides 10078–10083.
FIG. 11D shows the number of crosses of the location of the platform (mean±SEM) for Hdh$^{-ex5}$ knockout mice (black bar) and controls (hatched bar) during memory probe 1 (left) and memory probe 2 (right).
Figures 1, 11D:
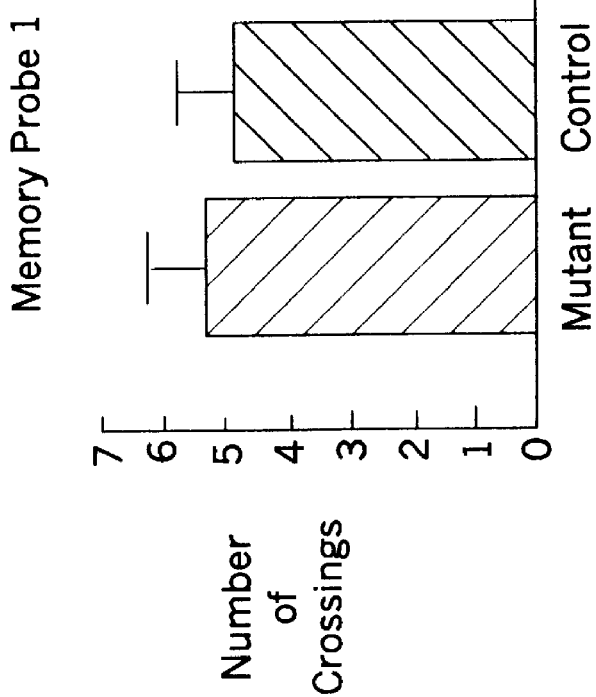

Mouse hd cDNA clones were initially identified using a human cDNA probe GT 70 by screening mouse brain and spleen cDNA libraries (FIG. 1). The GT 70 probe is described in our publication Rommens et al., (1993) Hum. Mol. Genet. 2, 901–907 and in our aforementioned Canadian patent applicaton. Additional cDNA clones were identified by repeated screening with the derived mouse cDNAs. A 1 kb PCR product corresponding to nucleotides 8000–9000 of the published human HD sequence was also used for screening. In total, 34 clones were isolated and analyzed by restriction mapping and DNA sequencing. A minimum of six overlapping clones and one PCR product encompassed 10,105 bases of the murine hd cDNA (mhd) (FIG. 1).

The 5' mouse cDNA (mhd2) (FIG. 1) spans nucleotides 1 to 2220. When the HD gene was first identified, the sequence of the human gene between nucleotides 1 and 340 was derived from genomic DNA which could be aligned with a cDNA starting 27 bp upstream of the CAG repeat. Identification and alignment of the mouse cDNA containing an additional 134 nucleotides further 5' of the human cDNA sequence suggests that this DNA segment is not likely to be interrupted by an intron in the mouse.

Nucleotide Sequence Analysis

Figure 3:
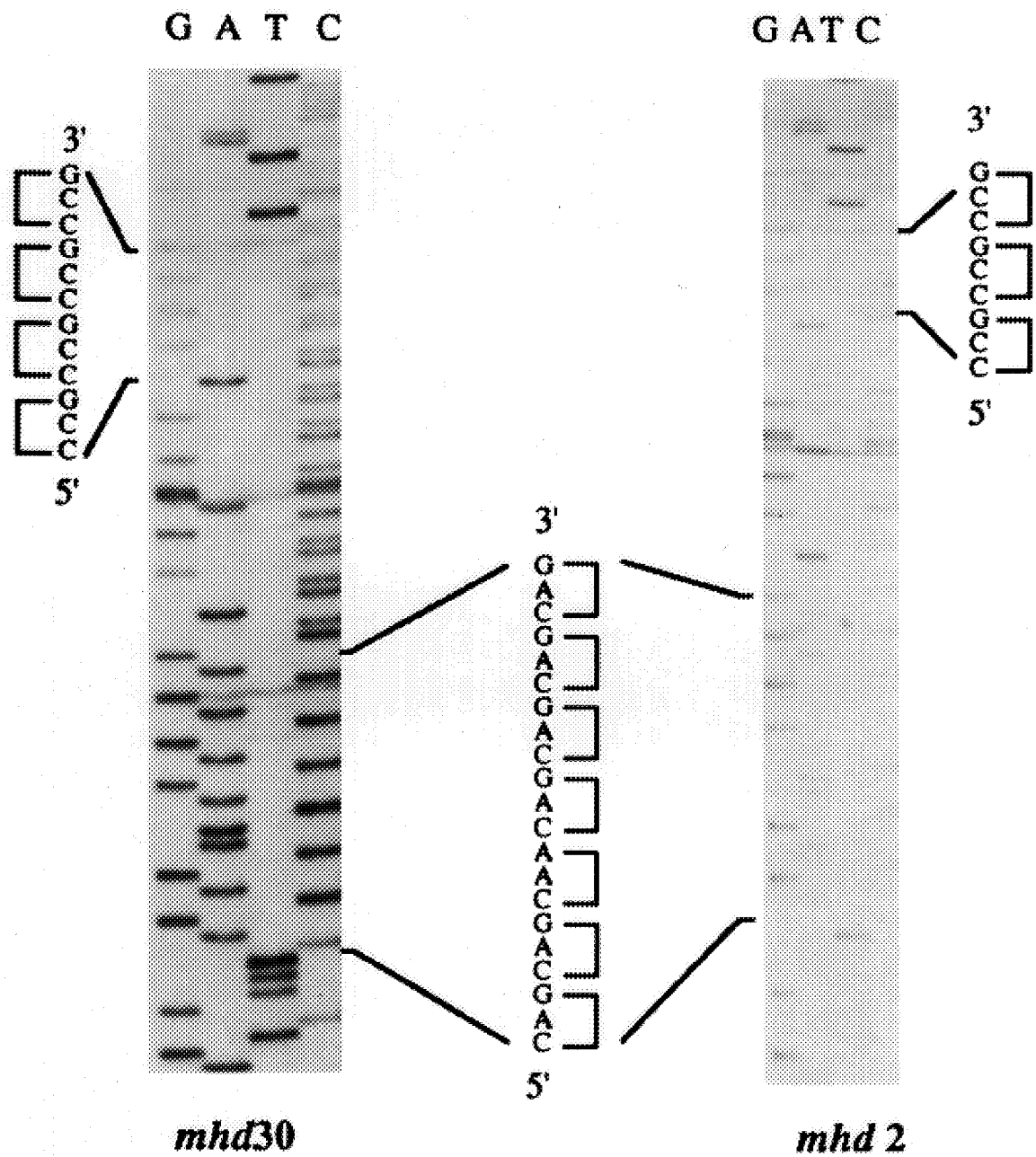
FIG. 3: The CCG repeat is polymorphic Mhd2 cDNA has 3 CCG triplets (SEQ ID NO:39) and mhd30 cDNA has 4 CCG repeats after nucleotide position 210 (SEQ ID NO:38 and SEQ ID NO:40). The CAG triplets in both mouse clones do not reveal polymorphism.

The mouse cDNA sequence is deposited in GenBank (Accession numbers L23312, L23313). The alignment of the mouse and the human cDNA sequence revealed conservation, with nucleotide sequence identity of 86.2% within the coding region (FIG. 2). In the mouse cDNA, the CAG repeat consists of seven triplets, and the CAG repeats are interrupted at the third triplet by CAA (FIG. 2 and FIG. 3). No polymorphisms for CAG length were observed in the cDNA clones identified.

In the mouse cDNA, starting at nucleotide 205, a starting sequence of CCG triplets occur but is interrupted by CCA and CCT within this repeat (FIG. 2 and 3). In two different mouse cDNA clones(mhd2 and mhd30) the CCG repeat between nucleotides 211–223 differs by one triplet suggesting polymorphism (FIG. 2 and 3). These clones are derived from two different mouse strains (C57BL6 and ICR outbred). The CCG repeat has now also been shown to be polymorphic in human DNA and varies between 7 to 12 CCG triplets.

Four deletions in the mouse sequence were seen including a 6 nucleotide deletion (GTGGCT between mhd nt 297–298), a single trinucleotide (ATA) deletion (between nt 5250–5251) and a 6 nucleotide deletion (GAGGAG) between nucleotides 7080 and 7081. In addition, there is a 24 nt deletion between nt 265–266. The latter sequence is highly GC rich containing imperfect repeats and different alignments of the deletion are possible. Each of these deletions were seen in at least two mouse cDNA clones. A single insertion of GGG trinucleotide appears in the mouse cDNA after nucleotide 1866. The reading frame of the cDNA is not altered with any of the deletions or with the insertion. It is notable that all these changes involve triplet insertions or deletions.

In addition to the CAG and CCG polymorphisms, three single nucleotide substitutions were identified between individual mouse clones. These include a A->T change at nt 529 of the mouse sequence (ATG->TTG Met->Leu), a G->C change at nt 1714 (GCC->CCC Ala->Pro) and a G->A change at nt 4023 (ACG-ACA no amino acid change) (FIG. 2).

Sequence Analysis of the Predicted Coding Sequence

The predicted length of the mouse protein is 3119 amino acids.

In the human cDNA, the predicted methionine codon at base 316 was postulated to be the initiation codon of the open reading frame. However, the presence of other downstream methionine residues indicated that translation may start at a more 3' ATG codon predicting a smaller protein. If this were the case, the $(CAG)_n$ repeat that is expanded in affected persons with HD could then be in the 5' untranslated region of the HD mRNA. A candidate ATG initiation codon was identified in the mouse cDNA at nucleotide 118 and the mouse open reading frame extends only 6 nucleotides upstream of this ATG. This is the first ATG in the open reading frame, and previous studies have shown that the first ATG in an open reading frame is the initiation point for translation in over 90% of vertebrate messenger RNAs. The mouse (CAGTAAGCCGTCATGG) (SEQ ID NO:19) sequence flanking the putative start sites match the Kozak consensus at most relevant positions. Using a score based upon discrimination energy, which calculates the relative likelihood of all nucleotides occurring in their observed positions relative to the start site for translation, we found that the above mouse and human sequence provides better matches to the consensus than most of the 130 human genes we tested. In contrast, the next downstream ATG at position 139 in the mouse provides a poor context for translation initiation.

These features argue that the translational start site for the mouse cDNAs is the first in-frame ATG codon of the open reading frame. This would also indicate that the polymorphic CAG sequence which is unstable on HD chromosomes is contained within the translated region of the predicted protein sequence.

Sequence Analysis of the 5' and 3' UTR Region mhd2 contained 117 basepairs of 5'UTR sequence (FIG. 2). The mouse 5' sequence contains an additional 7 basepairs inserted at position 268 of the human sequence (FIG. 2). The strong sequence homology in the 5' region does suggest some functional significance although no known regulatory sequences were recognized.

The mouse, sequence, contains the hexanucleotide AGTAAA 17 base 5' of the polyA tail (FIG. 2) which may be a signal for directing cleavage and polyA addition.

RNA analysis revealed the presence of two transcripts in the mouse brain (FIG. 4) but we have not yet identified any cDNAs in the mouse which differed in size or sequence at their 3' untranslated regions. Nevertheless, the presence of two distinct transcripts in mouse would suggest that differential polyadenylation may result in two mRNA species.

Animal Models

The cloning of the Huntington's Disease gene recently represents a major milestone in the study of this disease but the information gained provides new insights into the putative function of the gene. Sequence comparison to other known vertebrate genes did not identify any homologies.

The cloning of hd, the mouse homologue of the HD gene, offers the opportunity to study the pathophysiology of this disease and the function of the gene by producing a transgenic mouse. Such a mouse will eventually provide significant insights into the understanding of other complex neurological disorders. In particular, it could be important for those disorders which like HD are essentially neurodegenerative and are associated with trinucleotide repeat expansion.

In one embodiment a mouse model for Hd can be developed, by introducing additional CAG repeats to the HD gene. A mouse HD model using expanded repeats would also allow one to study trinucleotide repeat (TNR) instability in the germline. Furthermore, in order to ascertain the function of the HD gene, we can ablate the gene in all tissues and in a tissue-specific manner. A mouse model for HD allows us to monitor various therapeutic strategies (using pharmaceutical compounds and gene therapy) and allows us to study the progress of the disease by sacrificing mice at various stages of the disease. Our general scheme is outlined here, as follows:

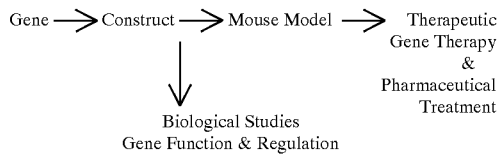

Mouse serves as an excellent model system for in vivo analysis of genes both from the point of view of determining their basic biological function and for understanding more about their regulation. Moreover, mice offer several advantages over other animal models. Firstly, they require relatively little care and attention and can be housed in a small space. For this reason they are relatively economical to maintain. Secondly, they have a short gestation period (3 weeks) with a relatively larger litter size (average litter size, 6–8) (Hogan et al. (1986) Manipulating the Mouse Embryo, Cold Spring Harbour Press). Overall, transgenic mice mimic the expected phenotype indicating they represent a good physiological model for human genetic disease. Indeed, the mouse models have now been produced for several human diseases including cystic fibrosis (Dorin et al. (1992) *Nature* 359:211–215), Lesch-Nyhan syndrome (Kuehn et al., (1987) *Nature* 326:295–298; Wu and Melton (1993) *Nature Genetics* 3:235–240) and retinoblastoma (Lee et al. (1992) *Nature* 359:288–294; Jacks et al. (1992) *Nature* 359:295–300).

Transgenic Mice

A suitable model is required in order to test novel therapeutic strategies including the administration of novel compounds and gene therapy procedures. In addition, these animal models will prove essential for investigating the genetic basis of trinucleotide repeat instability as well as the molecular basis of neurodegeneration, not just in HD but also in other neurodegenerative diseases and especially those associated with trinucleotide repeat instability. We have generated transgenic mice using both cDNA constructs and Yeast Artificial Chromosomes (YACs) spanning the HD gene.

Transgenic mice, carrying modified genes, can be generated using two different schemes. Firstly, a DNA construct carrying the desired mutation can be delivered by direct microinjection into the pronuclei of 1 cell zygotes. This is the most efficient and commonly used technique for transferring DNA into the germ line (Meisler (1992) *Trends Genet.* 8:341–345; Merlino (1991) *FASEB J.* 5:2996–3001)

but generally results in random integration of the transgene. Alternatively, "gene targeting", a more elaborate approach, can be used to introduce modifications at any given gene (Robertson (1986) *Trends Genet.* pp. 9–13; Mansour et al. (1988) *Nature* 336:348–352). This is achieved by homologous recombination of targeting vector carrying the required modification, with an embryo-derived stem cell (ES cell). ES cells are pleuripotent and when introduced into a blastocyst (by microinjection) are capable of contributing to the germ line of the resulting chimeras which are mated to generate mice homozygote for a given mutation. Using gene targeting, an individual gene can be "knocked out" by, for example, introducing a selective marker (commonly neomycin resistance gene), within an exon. Moreover, more subtle mutations, for example point mutations, can also be introduced (Rubinstein et al. (1993) *Nucleic Acids Res.* 21:2613–2617; Bradley et al. (1992) *Biotechnology* 10:534–538).

The cre-lox system, a novel approach based on the ability of transgenic mice, carrying the bacteriophage Cre gene, to promote recombination between 34 bp repeats termed loxP sites, allows ablation of a given gene in a tissue specific and a developmentally regulated manner (Orban et al. (1992) *PNAS* 89:6861–6865. LoxP sites can be placed flanking an exon of any given gene. Thus, transgenic mice carrying the Cre gene under the control of a selected promoter can be crossed with transgenic mice carrying a transgene flanked by loxP sites to generate doubly transgenic mice. The pioneering work in developing this system was carried out here at UBC (Orban et al. (1992) *PNAS* 89:6861–6865). We aim to exploit this technology to target specific tissues in mice, primarily brain, in a developmentally regulated fashion in order to produce a mouse mimicking Huntington's Disease.

For some applications, it is necessary to introduce large genomic clones into mice. This can be done by utilizing YACs which allow direct cloning into yeast of continuous large stretches of DNA. Recently, several groups have reported successful integration and germ line transmission of YAC clones into mice via ES cells or by direct microinjection (Strauss et al. (1993) *Science* 259:1904–1907; Jakobovits et al. (1993) *Nature* 362:255–258; Schedl et al. (1993) *Nature* 362:258–261. For the HD gene, which spans approximately 200 kb (The Huntington's Disease Collaborative Research Group (1993) *Cell* 72:971–983), this is particularly relevant and offers the opportunity to introduce the entire gene as a single YAC clone.

We developed YAC transgenics from YACs encompassing the entire HD gene as well as neighboring genes. Two YACs were used in these studies, YGA2 and 353G6. YGA2 extends greater than 300 kb 5' and 50 kb 3' of the HD gene whereas 353G6 contains at least 20 kb of 5' and 140 kb of 3' flanking DNA. We have created transgenic mice from these YACs as described above. These mice have been extensively characterised with respect to the integrity of the YAC transgene. Twelve markers including YAC vector sequences were deployed for this purpose. Of the 46 potential transgenic mice, at least five appear to have integrated the transgene with no obvious rearrangements. In addition, we have demonstrated by RT-PCR analysis that two of the mice are expressing the entire coding region. In addition, neuropathological and behavioural experiments can be carried out. One can exploit homologous recombination in ES cells to generate YACs with large CAG repeats in the disease range.

Designing Constructs

We can establish a mouse model for HD by introducing various constructs, carrying specific alterations in the HD gene into mice, using a combination of approaches described above. The constructs can be of several types. Firstly, we can design constructs harbouring large numbers of CAG repeats (up to 50 or more). The additional repeats will be introduced by conventional cloning, site-directed mutagenesis and by PCR based strategies (Sambrook et al. (1989) Molecular Cloning:*Cold Spring Harbour Press.* Using these strategies, additional CAG repeats will be inserted in tandem with endogenous repeats at the appropriate site. We have already isolated genomic clones encompassing the CAG repeat (unpublished data) and have generated the full cDNA restriction map from our sequence data for the murine hd gene. We can introduce specific changes throughout the gene in order to generate a variety of transgenics, some with the null phenotype.

We have generated cDNA constructs from the full length HD cDNA with a range of different CAG repeats lengths. Briefly, the constructs were derived by sequential ligations of cDNA clones from a frontal cortex cDNA library. Larger CAG repeats were derived by PCR amplification of these sequences from HD patients. Two expression vectors were chosen, pCMV and RcCMV. These constructs were linearised and injected into single cell fertilised oocytes. Transgenic mice were derived and are being assessed. In parallel, using in vitro culture assays, we have demonstrated that the constructs are expressing the protein. The transgenic mice will be assessed in detail by looking for neuropathology and by characterising their behavior in detail as described elsewhere in this application.

We can also "knock out" the endogenous gene completely in all tissues and in a tissue specific manner by introducing in-frame stop codons and deletions within individual exons using both ES-cell technology and the cre-lox system. We can also arrange for over-expression of the gene in specific tissues. So, overall, we can not only engineer mice which mimic HD but also to generate mice with changes and modifications throughout the gene to ascertain the basic function of the HD gene.

Targeted Disruption of the HD Gene

To explore the normal function of the HD gene and its role in development, we can disrupt any selected exon of the HDh gene. We chose to disrupt the murine Hdh gene in exon 5 using the pHdh Neo6 targeting construct and deleting approximately half of exon 5 (see Table 4) plus intron 4 sequences and replacing it with a PGKneobpA cassette. ES cells from each cell line containing the targeted event, the Hdh mutation, were injected into blastocysts and implanted into pseudopregnant mothers. No liveborn mice (0/225) homozygous for the $Hdh^{-ex5}$ were evident (Table 2A, $p<10^{-6}$). Because the liveborn progeny were derived from intercrosses of heterozygotes originating from three independently targeted ES cell lines, the lack of $Hdh^{-ex5}$ live offspring is not due to another mutation inadvertently generated in one ES cell line. These data clearly show that homozygosity for the $Hdh^{-ex5}$ mutation is lethal during embryonic development.

Analysis of 173 phenotypically normal embryos at different stages of gestation revealed that only 4 (2.37%) were homozygous mutants (Table 2B, $p<10^{-6}$). In contrast, genotyping of 35 resorbed embryos from 7.5–12.5 days gestation revealed that 28 (~80%) were homozygous mutants (Table 2C, $p<10^{-6}$). The high frequency of postimplantation resorptions, lack of phenotypically normal looking Hdh mutant (−/−) embryos after 8.5 days of gestation and complete absence of liveborns homozygous for this mutation, clearly shows that the murine Hdh gene is essential for early postimplantation development.

Homozygous Hdh$^{-ex5}$ mutants die at around E7.5 and display a phenotype in which gastrulation is significantly disturbed (FIG. 10). During gastrulation in mammalian development, the three germ layers, ectoderm, mesoderm and endoderm are generated. While the precise cause of embryolethality is not yet determined, our results suggest that although the three germ layers are formed, subsequent failure to neurulate leads to complete disorganization of the embryo such that it never forms somites, nodes or the notochord and does not proceed to organogenesis.

This indicates that mesoderm is formed, but that the normal Hdh protein may be critical for neurulation and development of the anterior-posterior axis. It is possible that inductive events between the chordamesoderm and surface ectoderm do not occur in the homozygous mutant embryos, leading to cessation of development. Clearly the HD gene plays a crucial role in normal gastrulation.

Numerous other naturally occurring mutations and gene targeting experiments have also been shown to result in lethality during gastrulation due to primary disturbances in the primitive ectoderm (Reviewed in Copp, 1995). These studies suggest that many of these genes, now including the HD gene, may play crucial roles as either regulatory molecules underlying gastrulation in vertebrates, or for essential cellular housekeeping functions which may be important for exchanging nutrients with the mother (Copp 1995).

Behavioral Changes in Heterozygous Mice with the Hdh$^{-ex5}$ Mutation

Hdh$^{-ex5}$ heterozygous mice differed from controls in several important ways, the most apparent being increased reactivity to handling. These mice were more active than controls when placed in a novel photocell cage. This effect was seen in both light and dark conditions, where crossings were more than 2× greater in the heterozygous mice. Taken together, the motor activity data suggest that the Hdh$^{-ex5}$ mice habituate more slowly to the stimulus features of a novel environment and therefore remain more active than controls during both phases of the motor activity test. These changes in motor activity appear to be quite specific, as the Hdh$^{-ex5}$ mice performed normally on two spatial tasks (FIG. 11).

T-maze alternation, the 8-arm maze and foraging for food assess a rodent's ability to use memory of previous responses within a trial to plan subsequent responses and spatial function. Both groups of mice performed equally well these maze tasks, indicating normal short-term memory and spatial function.

The performance of Hdh$^{-ex5}$ mice on the Morris Water Maze task was particularly revealing. The hidden platform version of this task has been used to provide an unambiguous assessment of spatial abilities in rodents (Morris, 1981). When tested for the first time with the hidden platform in a fixed location, mutant mice performed as well as controls, with both groups showing normal learning curves and intact spatial memory on a memory probe trial (FIG. 11). Therefore it seems that Hdh$^{-ex5}$ mice have normal capacity for spatial navigation, memory for location in space, and normal short-term learning ability. Furthermore they must have normal perceptual and motor capacities required to see extra maze visual stimuli located in the test room and normal swimming behaviour.

Despite normal functioning on the preceding phase of spatial learning in the Water Maze, mutant mice were severely affected during the reversal trials (FIG. 11). They failed to reach the same degree of proficiency in the latency to reach the platform and showed no memory of the correct platform location on a memory probe trial where the platform was removed from the pool. This may reflect a deficit in cognitive flexibility in which a previously successful strategy must be inhibited in order to develop a new strategy that is appropriate for a change in the demands of the task. Mutant mice appeared to be incapable of making this strategy switch. It is noteworthy that deficits in switching from one set of learned responses to another is a well documented, behavioral correlate of damage to the basal ganglia and in particular to the dorsal striatum (Robbins and Everitt, 1992). Proactive interference by the original memory of the location of the platform may provide an alternative explanation of these data. Behavioral differences seen in Hdh$^{-ex5}$ mice relative to controls are similar to those seen in rodents with lesions to the basal ganglia. Kainic acid lesions of the dorsal striatum which in part reproduce the neurochemical profile of HD, can cause an increase in spontaneous locomotor activity (Dunnet and Iverson, 1981). Rats with similar lesions performed normally in the initial acquisition of a water maze task, but when the platform was moved to another quadrant, lesioned animals were impaired relative to controls (MacDonald and White, 1994), findings similar to those seen in Hdh$^{-ex5}$ mice.

Figure 12A:
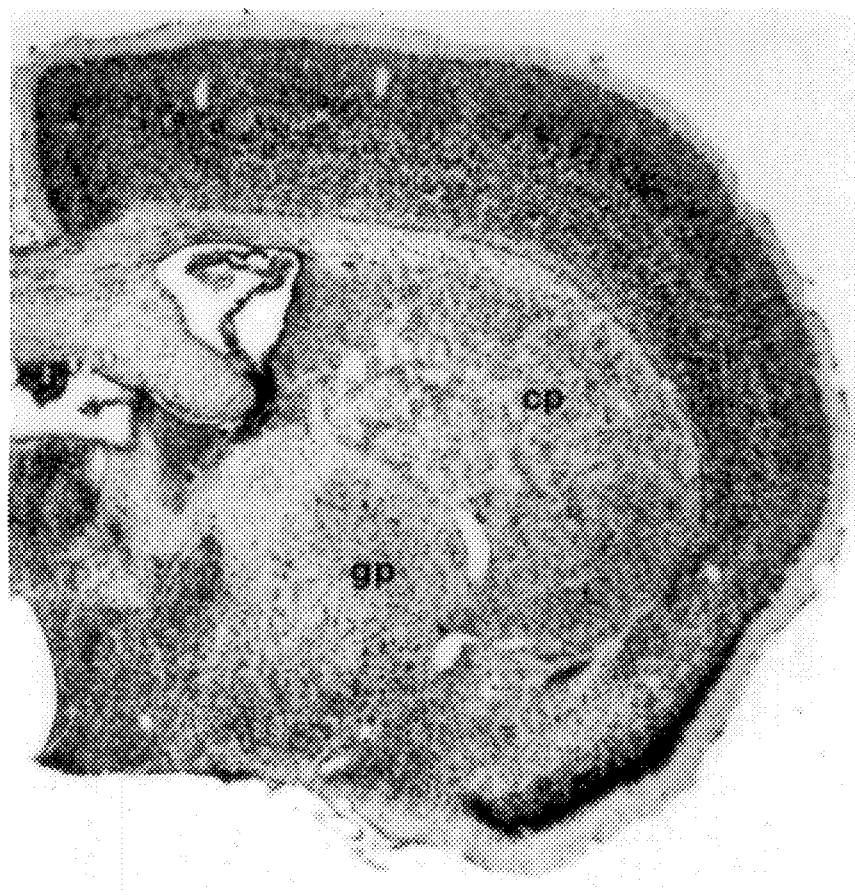
FIG. 12A shows the subthalamic nucleus in wild type control mice. The subthalamic nucleus was easily recognized as a small elongated nucleus containing densely packed, darkly stained neurons, located between the zona incerta dorsally and the cerebral peduncle ventrally. The nucleus is ovoid medially (left) with a tail extending laterally (right). Calibration bar=300 μm.
Figure 12B:
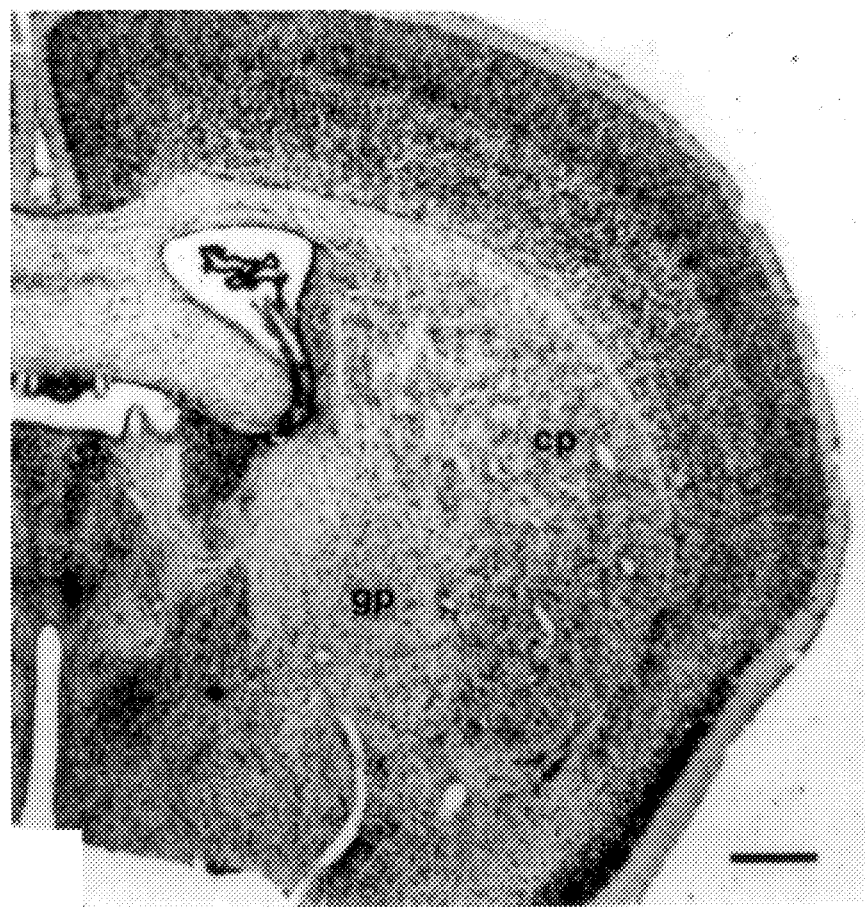
FIG. 12B shows the subthalamic nucleus in heterozygous mice. The subthalamic nucleus was easily recognized as in FIG. 12A. Note the decreased size of the nucleus in FIG. 12B compared to FIG. 12A, which is most evident in the middle third. Calibration bar=300 μm.
Figure 13A:
FIG. 13A is a frontal section through the caudate-putamen (cp) and global pallidus (gp) of wild type control mouse. Calibration bar=500 μm.
Figure 13B:
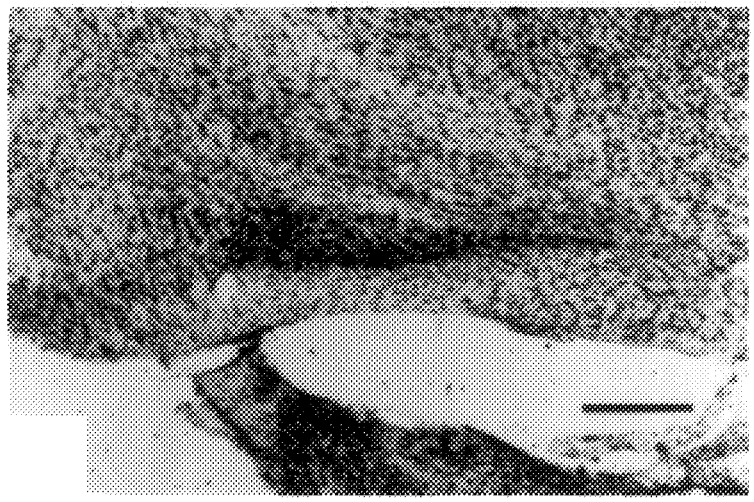
FIG. 13B is a frontal section through the caudate-putamen (cp) and global pallidus (gp) of a heterozygote. Calibration bar=500 μm.

Morphological Changes in the Brains of Mice Heterozygous for the Hdh$^{-ex5}$ Mutation We have demonstrated significant decreases in both the volume of the subthalamic nucleus and the total number of subthalamic neurons in the two heterozygous mice compared to two littermate controls (FIGS. 12 and FIG. 13, Table 3). The total number of neurons in the globus pallidus appeared to be reduced, although morphometric analyses would be required on a larger subject sample to verify this observation. In contrast, no differences at all were seen in the caudate-putamen, substantia nigra, hippocampus or the thickness of the cerebral cortex. The 45% reduction in the number of subthalamic neurons in heterozygous mice could result from decreased neurogenesis during prenatal development or from increased apoptosis during late prenatal or early postnatal development. A third possibility is that subthalamic neuron loss is due to necrosis during early development with rapid dissolution of necrotic tissue and no residual gliosis at four months of age. Alternatively, the influence of two genetic backgrounds on the growth of the subthalamic nucleus between heterozygotes and littermates has not been excluded.

The subthalamic nucleus, which is one of the five nuclei comprising the basal ganglia, functions in the extrapyramidal control of movement and has previously been implicated in the pathophysiology of HD (Folstein, 1989; Harper, 1991; Parent & Hazrati, 1995). Although neuronal loss from the subthalamic nucleus has been reported in HD (Lange et al., 1976), characteristic lesions involve a substantial loss of GABAergic medium-spiny neurons in the neostriatum (1976; Lange et al., 1976; Graveland et al., 1985). In the early years of symptomatic HD, pathology in the neostriatum is minimal (Vonsattel et al., 1985), indicating that the pathophysiology of chorea precedes obvious necrosis in the basal ganglia. One question that arises is whether changes in the subthalamic nucleus might in some way be related to the striatal pathology and clinical phenotype of HD. It has previously been suggested that striatal lesions in HD alter the physiology of subthalamic neurons to produce chorea (Albin et al., 1989). Interestingly, acute lesions of the subthalamic nucleus due to stroke (Whittier, 1947) or induced experimentally in primates (Capenter et al., 1950) manifest with ballismus which is exaggerated, high amplitude chorea. In contrast, little is known concerning the effect of chronic, continued damage to the subthalamic nucleus.

Implications for the Pathogenesis of HD

The Hdh$^{-ex5}$ mutation in the murine HD gene results in embryolethality before E8.5, indicating that this gene is expressed very early in development and that there is no functional redundancy for this gene. In contrast, humans homozygous for the CAG mutation, survive and have a phenotype (Wexler et al., 1987) and neuropathology (Kremer et al., 1994) similar to heterozygotes for this mutation. Furthermore, there is no report of increased miscarriage rate in offspring of parents both heterozygous for the HD mutation. Taken together, these data provide compelling evidence that CAG expansion in the HD gene does not result in complete loss of normal function of this gene. Furthermore, our data showing lethality of the mutant allele, also argues against a complete, dominant negative mechanism for the pathogenesis of HD where the mutant gene results in complete loss of its own function and also inactivates the normal product. In contrast, the findings of embryolethality for mice homozygous for the mutation and equivalence of the homozygote and heterozygote phenotype of HD in humans is more compatible with CAG expansion, conferring a novel gain of function independent of the protein's normal physiological role. Recent evidence clearly shows that the CAG repeat in the HD gene is indeed translated into a polyglutamine stretch (Jou and Myers, 1995).

Mice heterozygous for the Hdh$^{-ex5}$ mutation have behavioural deficits similar to that seen in rodents with lesions in the striatum, and two of these same mice analysed, have significant reductions of neurons in the subthalamic nucleus. Intriguingly, this nucleus also shows obvious neuronal loss (~25%) in patients with HD (Lange et al., 1976), which raises the question whether partial loss of normal function of this gene results in neuronal loss in the basal ganglia. An alternative possibility is that expression of the truncated HD protein in the heterozygous mice, results in a phenotype with some similarity to HD not due to partial loss of function, but due to the truncated protein acting as a toxic product.

Interestingly, CAG expansion in the androgen receptor gene is associated with X-linked spinal and bulbar muscular atrophy (SBMA) (La Spada et al., 1991), but affected males also have signs of partial loss of normal androgen receptor function, manifest with gynecomastia, and reduced fertility (Arbizu et al., 1983). While CAG amplification in the androgen receptor gene confers new functional properties (Mahtre et al., 1993), at the same time, this is associated with partial loss of normal function. Pathological involvement of the basal ganglia in mice heterozygous for the Hdh$^{-ex5}$ mutation, suggests that partial loss of normal function of the HD gene might also contribute to the phenotype of HD.

Data presented here suggests that the HD gene plays an essential function during gastrulation in early embryogenesis and may also have an important physiological role in the basal ganglia. Similar to the androgen receptor gene, it is possible that CAG expansion in the HD gene also results in partial loss of physiological function of this gene, with subsequent mild deficits in this region of the brain. Partial loss of normal function however, may be insufficient to result in a clinical phenotype. For example, one patient with a balanced translocation which disrupted the HD gene between exons 41 and 42, was still asymptomatic at age 46. In this patient however, the protein contains nearly two-thirds of the normal product which may be sufficient to exert its normal physiological role (Ambrose et al., 1994).

We therefore propose a model for the pathogenesis of HD which involves a gain of novel properties, in addition to a partial loss of its normal physiological role. Selective neuronal death caused by dysfunction of this widely expressed gene could reflect restricted expression of a protein which has altered interaction with an HD gene product with an expanded polyglutamine stretch. In addition, partial loss of the physiological role of this gene in the basal ganglia could also contribute to the HD phenotype.

This model has important implications for the design of therapeutic strategies as well as new research directions. One approach to treatment of HD is to decrease the expression of the HD gene which might be expected to mitigate the phenotype. A more successful approach may be to determine which cellular proteins specifically interact with the HD gene product and to direct attention to interfere with this interaction. This approach could also be insufficient to cure HD as additional strategies to replace the partial loss of normal function of the HD gene may be necessary to reach that goal.

Drug Screening

Compounds could be screened in both heterozygous and homozygous mice. In heterozygous mice drugs could be developed to offset or delay neurodegeneration as well as alleviate the cognitive defects and behavioral defects including hyperactivity associated with the disease. Heterozygous transgenic mice could be first behaviorally assessed using testing procedures which include motor activity testing, T-maze alteration, radial-arm maze, and Morris water maze testing. After administration of said drug the same mice would be tested again with respect to these same parameters. In this manner, improvements in cognitive function could be evaluated for a given drug. Follow up histological and morphometrical examination of brains from these mice also provides for the evaluation of a drug's effectiveness to reverse or delay neurodegeneration.

Homozygous HD mice serve as models to study embryogenesis and development. HD homozygous mutant embryos die during early post-implantation. These embryos could be recovered and portions cultured in vitro in the presence of novel drugs designed to compensate for the lack of HD gene product in these embryos. Drug testing in these mice could lead to the development of drugs which could rescue early embryos normally aborted.

Gene Therapy

One approach to the therapy of HD is to insert an antisense version of the HD gene into brain tissue specifically affected and susceptible to the neurodegenerative effects of HD. Gene transfer can be carried out by using physical methods of electroporation, bead transfection, microencapsulation, and protoplast fusion. These methods are currently available although some are of low efficiency. We can also carry out gene therapy by delivering appropriate transgenes directly into specific regions of the brain using viral vectors. This technology is already established and replication defective adenovirus vectors and herpes simplex virus based vectors are already being used for gene therapy for other diseases (Breakefield (1993) *Nature Genetics* 3:187–189). Retroviral vectors are particularly useful for somatic gene therapy because of a high efficiency of infection and stable integration and expression. The cDNA of the HD gene could be cloned into a retroviral vector and driven from its endogenous promoter or the retroviral long terminal repeat. Expression of normal levels of normal protein may be beneficial to protein deficient or protein-mutants. Other viral vectors could also be employed including adeno-associated virus, vaccinia virus, bovine papilloma virus, or a herpes virus such as Epstein-Barr virus. Transplantation of neuronal cells expressing normal HD can also be achieved by delivering such cultured cells directly by injection to affected areas of the brain. This type of therapy would be particularly useful to study in the transgenic heterozygous mice.

Eventually, we can direct delivery of therapeutic agents such as antisense RNA to specific regions of the brain to prevent the transcription of a mutant HD gene or to alter its transcription.

METHODS FOR USE IN THE FOLLOWING EXAMPLES

1. Screening of DNA Libraries

Approximately 1 million plaque-forming units of mouse spleen of the C57 Blue strain and brain of the ICR outbred strain from Strategene Inc., San Diego, Calif., were plated onto six 24×25 cm² BIBCO petri plates. Two sets of replica filters were made using Amersham Hybond N+ nylon filters through the use of standard methods. Radio-labelled probes were prepared by random hexamer priming. Filter prehybridization and hybridization were performed in a 0.5 molar sodium phosphate buffer at pH 7.2 with 7% sodium docecyl sulfate and 1 nM of EDTA at 65° C. Autoradiography was then performed for 24–72 hours. Following a second and tertiary screening, the positive plaques underwent in vivo excision from Lanbda Zap vectors according to Strategene's protocol to release the Bluescript phagemid.

2. DNA Sequencing

Plasmid DNA was prepared using a Qiagen plasmid DNA preparation column. Automated sequencing of the bases of the DNA was performed using an ABI 373A sequencer. Manual dideoxy sequencing was performed using a US Biochemicals sequenase kit. Direct PCR sequencing as performed as described in Goldberg, Y. P. et al., [*Human Molecular Genetics*, 1:669–675 (1993)]. Sequencing PCR primers were synthesized using a PCR Marte 391 DNA synthesizer of Applied Biosystems, Inc.

3. RNA Preparation

Mouse tissues were disrupted by a Polytron homogenizer in guanidinium isothiocyanate. Total RNA was then isolated by centrifugation through a CsCl cushion, as in MacDonald, R. J. et al., [*Meth. Enzymol.* 152:219–234 (1987)]. For hybridization analysis, RNA was fractionated on agarose gels (1%) containing 0.6M formaldehyde and transferred to Hybond membrane (Amersham) according to standard procedures in Sambrooke, J. et al., [Molecular Cloning: A Laboratory Manual, 2nd Ed., *Cold Harbour Laboratory Press,* Cold Spring Harbour, N.Y. (1989)].

4. Hybridization Analysis

DNAs were digested with BRL restriction enzymes according to the manufacturer's recommendations and after electrophoresis, transferred to Hybond N+ membranes (Amersham). Following cross-linking with UV radiation, blots were hybridized with cDNA fragments, (mhd 896, a 3' mouse cDNA) radio-labelled by random priming. Hybridizations were carried out in 50% formamide hybridization buffer containing SSPE, Denhardts solution, salmon sperm DNA, and dextran sulphate (10%) at 42° C. Final conditions for washing included 0.2XSSC with 0.1% SDS at 60° C. Blots were exposed to X-Omat AR (Kodak) film for 3 days with single intensifying screens at −70° C.

5. RT-PCR Analysis

Reverse transcription was carried out using Superscript Preamplification System (BRL). First strand synthesis was performed using the mg2 oligonucleotide primer (SEQ ID NO:17) (ATCTTCAGCAGGGATACGGTTGAC) for mouse total brain mRNA and hd10103 oligonucleotide primer (SEQ ID NO:18) (TGAGAAGAAAGAGAGAAGGGAG) for human brain mRNA (FIG. 5). 3 ug of mRNA was used for first strand synthesis. PCR reactions were carried out using a reaction with 1.5 mM $MgCl_2$ and Taq polymerase (Promega). Amplifications were performed for 35 cycles for primer sets MG4 (SEQ ID NO:2) and MG5 (FIG. 1) with conditions of 30 seconds at 94° C., 30 seconds at 64° C. and 45 seconds at 72° C.; 35 cycles for primer sets MG7 (SEQ ID NO:7) and MG8 (SEQ ID NO:4) (FIG. 5) with conditions of 30 seconds at 94° C., 30 seconds at 60° C. and 90 seconds at 72° C.; 35 cycles for primer sets HG7 (SEQ ID NO:5) and HG8 (SEQ ID NO:6) (FIG. 5) with conditions of 30 seconds at 94° C., 30 seconds at 62° C. and 90 seconds at 72° C.

6. Sequence Analysis

Sequence data were entered into a Sun IPX Workstation, and analyzed with the Staden sequence analysis package [Staden, R. *Nucl. Acids. Res.* 10(9) 2951–1961 (1982)]. The nucleotide and amino acid alignments used to treat FIG. 2 utilized algorithm of Myers and Miller [Myers, E. W. and Miller, W., *Comput. Applic. Biosc.* 4:11–17 (1988)]. A search for protein motifs was made using the PROSITE database [Bairoch, A., *Nucleic Acids Res.* 19 Suppl., 2241–2245 (1991)].

7. Constructing the pHdhNeo6 Targeting Vector

A phage genomic library from the 129/Sv mouse strain (Stratagene) was screened using a probe encompassing exon 5 of the murine Hdh cDNA (Lin et al.,1994). A 5.4 kb genomic fragment including murine exons 4 and 5 was subcloned into pBluescriptlIKS+ (Stratagene). A 3.5 kb EcoRl-Xbal clone was derived by digesting with Espl to remove a 600 bp fragment encompassing intron 4 and approximately half of exon 5 (see FIG. 1A). The Espl site was end-filled with klenow (Sambrook et al., 1989) and a blunt ended EcoRl-Xhol fragment from PGKneobpA (Soriano et al., 1991) was introduced.

8. Detecting Homologous Recombination in ES Cells

PCR was used to screen for homologous recombination using primers P6 (GGAGGCTAGAATGCTTGCAG) (SEQ ID NO:9) and P7 (TCTATGGCTTCTGAGGCGGA) (SEQ ID NO:10). Following an initial denaturation step (96° for 1 min.) forty cycles of PCR were performed (1 min @94°, 90 secs @60°, 120 secs @72°) with a final step of 72° for 10 min., using the 9600 Perkin Elmer machine.

9. Generation of Germline Chimeras

Blastocysts were collected from pregnant C57BL/6J females at 3.5 days post-coitum. Approximately 8–10 ES cells were microinjected and implanted into pseudopregnant ICR foster mothers. Chimeras identified by the presence of an agouti coat colour were test mated with C57BL/6J females. Agouti offspring were tested for the targeted Hdh gene by southern blotting.

10. RT-PCR and Sequencing

Total mRNA was extracted from freshly isolated tissue using the guanidium isothiocynanate method (Chomczynski and Sacchi, 1987). Poly A+ RNA was extracted using the Micro-Fast Track mRNA isolation kit (Invitrogen Corporation). Reverse transcription was performed using the SUPERSCRIPT Preamplification System (GIBCO BRL) with both a gene specific primer P16 (AATTTCATTGTCATTTGCGA) (SEQ ID NO:14) and random hexamers in separate reactions. 5 ml of the RT product was used for PCR amplification using primers P11 (CGATGCGGAGTCAGATGTCA) (SEQ ID NO:15) and P14 (GGTCTTTTGCTTGTTCGGGT) (SEQ ID NO:16). The shorter 167 bp PCR product was subcloned using the TA cloning kit (Invitrogen Corporation) and sequenced using an ABI automated sequencer.

11. Genotype Analysis

For PCR analysis, embryos were incubated overnight in a lysis buffer containing 20 mM Tris, 50 mM KCl, 0.45%

NP-40, 0.45% Tween-20, 0.01% Gelatin and 100 ug/ml Proteinase K and overlaid with mineral oil. The samples were then incubated at 94° C. for 10 min. and 5 ml was used for a 25 ml PCR reaction in the 9600 Perkin-Elmer machine. Genotyping was carried out using p8 (SEQ ID NO:11) (TGGCAAGACAATAGCAGGCA), a Neo specific primer, p586 (SEQ ID NO:13) (AGTTTGCGTGCTGCCCTGTG), a primer derived from exon 5 of mouse and p9 (SEQ ID NO:12) (CCAGACAGGACATAGCTAGG), a primer from intron 5 (FIG. 7). All 3 primers (p8, p9 and p586) were used together in a single PCR reaction.

12. Histology

Embryos and whole decidua were fixed in Bouin's solution and embedded in paraffin wax. Serial sections of 5 mm were prepared and stained with hematoxylin and eosin.

Behavior Studies

13. Locomotion Test

Spontaneous locomotion was assessed using 3 clear Plexiglas photocell cages (25×25×26 cm) placed individually inside large dark chambers (45×45×100 cm). Individual photocell cages were illuminated by a 70 mW light bulb and had 4 parallel infrared photocell beams (2 on each axis) located 2 cm above the floor and 8 cm from each corner of the cage. Interruptions of any beam were registered incrementally by a microcomputer and were summed in 10 min bins during the locomotion test. Mice were placed individually in the apparatus and spontaneous locomotion assessed for a 4 hour trial. For the first 2 hours, the house lights were left on (Light Phase) and for the final 2 hours the lights were off (Dark Phase). Mice were tested in the middle of their light cycles, between 1–5 pm.

14. T-Maze Alternation Test

Following the locomotion test, mice were housed individually and were food-deprived over 7 days to 85–90% of their free-feeding weight. Mice were then tested for reinforced alternation responses on a T-Maze. The T-Maze was made of clear Plexiglass and consisted of a 2 goal arms (20 cm×10 cm×12 cm) each with a small plastic food cup (3 cm diameter, 0.5 cm deep) at the distal end and a start arm (36 cm×10 cm×12 cm) each of which could be blocked off by a wooden barrier (10 cm×18 cm). On the first 2 days each animal was habituated to the T-Maze for a 10 min period, where pieces of Kellogg's Froot Loop cereal were distributed on the T-Maze. Animals were subsequently tested on a standard alternation paradigm for 3 days. The first trial was a forced choice, in which mice could enter only one baited goal arm chosen at random. After entering the open arm, the mouse was confined there until food was consumed, following which it was placed back in the start arm and confined for 15 s. Twelve subsequent trials/day required the animals to choose the opposite arm from the one visited on the previous trial in order to receive food reinforcement. Following a correct choice, the mouse was again confined to the goal arm until it had eaten the food. An incorrect choice resulted in confinement in that arm for 30 s, after which it was placed in the start arm to await the next trial. The number of correct choices and the latency to reach the food cup of the chosen arm were recorded.

15. Radial-Arm Maze Test

One week after the completion of the T-Maze alternation tests, mice were given 7 days of testing on a radial-arm maze task. The maze was constructed from plywood and consisted of a central octagonal platform (35 cm diameter) with 8 arms radiating from the platform (35 cm×9 cm) with a plastic food cup at the distal end of each arm. On the first day of training, food was distributed around the center of the platform and in the food cups of 4 randomly selected arms. Individual mice were placed in the center of the maze and permitted to forage until all 4 pieces of food had been eaten from the food cups, all 8 arms had been visited, or until 10 min had elapsed. For all subsequent daily trials, pellets were placed in the food cups of 4 arms selected at random. A novel set of 4 arms was chosen each day and optimal foraging behaviour required animals to minimize re-entries into arms visited previously within a daily trial. Errors were scored as revisits to any arm entered previously. The experimenter recorded arm-choices and latencies to reach the food cup in the first arm chose and total time required to complete the daily trial.

16. Morris Water Maze Task

After completion of the radial-arm maze test, mice were provided with food ad libitum and 1 week later tested on the standard Morris Water Maze (Morris, 1981) paradigm. The water maze was a large white plastic tank 180 cm in diameter and 54 cm in height. The pool was filled with 20 cm of water at room temperature (22° C.), rendered opaque by adding one can of white powder paint. The submerged invisible escape platform was 19 cm in diameter. On top of the platform was a piece of metal mesh measuring 15×15 cm. The testing room had ample spatial cues taped to the walls. Swimming behaviour was recorded by a video camera mounted on the ceiling across the pool, that measured the path length and the time taken by each to find the hidden platform for each trial.

Spatial abilities were assessed in 4 distinct phases. Mice were given 4–6 trials/day (16 trials in total), with an inter-trial interval of 4–5 min. At the start of each trial, the mouse was placed in the pool at one of the 4 release points (N, S, E, or W) and swam until it found the hidden platform located in the centre of the NW quadrant, or until 120 s had elapsed. Failure to locate the submerged platform in the allotted time, resulted in the mouse being placed on the platform for 15 s, after which it was returned to its home cage. The release point order was randomized. When the mice demonstrated symtotic performance during the 4 trials on Day 3, they were given a 60 s memory probe trial with the platform removed from the pool. The amount of time spent in each quadrant of the pool was calculated along with the number of crossings over the platform site. The third phase (Days 4 and 5, consisting of 6 and 4 trials respectively) tested mutant mice to reverse spatial strategy by finding swimming directly to the platform, repositioned in the SE location. A second memory probe trial in which the platform was again removed from the pool and the percentage of time spent in each quadrant measured, along with the number of crossings over the platform site.

17. Data Analysis

Statistical analyses employed two-factor between/within design analysis of variance (ANOVA), one-factor ANOVA for simple main effects. For the probe trials of the water maze experiment Tukey's post-hoc tests were used to determine which quadrants of the pool animals spent significantly more time in. All values in text and figures are expressed as mean±SEM.

18. Histology and Morphometry of Brains of Mice Heterozygous for the Hdh$^{-ex5}$ Mutation Brains from 2 heterozygous mice and 2 wild-type controls were examined at 4 months of age. Mice were anesthetized by an intraperitoneal injection of sodium pentobarbital (80 mg/kg) and perfused through the ascending aorta with a fixative solution containing 4% paraformaldehyde and 1% glutaraldehyde in 0.1M phosphate buffer (pH 7.4) at a perfusion pressure of 120 mm Hg for 60 minutes. The brains were removed, weighed and placed in additional fixative solution for 24 hours. The brains were bisected in the midline and serial frozen sections were cut at 30 μm in the transverse plane throughout the entire length of the right half of each brain. Every second section in this series was mounted on chrome alum gelatin-coated slides and stained for Nissl substance using 0.1% thionin in 0.1M acetate buffer (pH 3.7).

All histological sections were coded to prevent experimenter bias during the morphometric analyses. The individual volumes of the caudate-putamen, globus pallidus, subthalamic nucleus, substantia nigra (i.e. both the pars compacta, PC, and the pars reticulata, PR) and hippocampus were measured in mm$^3$ on the serial Nissl sections. Individual sections were visualized at a final magnification of ×48 and the area of each nucleus was measured in mm$^2$ using an image analysis system (Bioquant System IV, R&M Biometrics, Nashville, Tenn.). The volume was calculated from:

$$V = \Sigma A \times T \times 2$$

where $\Sigma A$ is the sum of area measurements, T is section thickness, and 2 is the periodicity of the section sample.

Measurements of the numerical density of neurons ($N_V$, neurons per mm$^3$) were made in the caudate-putamen, globus pallidus, subthalamic nucleus and substantia nigra (PR) using the method of Abercrombie (1946). Briefly, sections were examined at a final magnification of ×1025. Neurons were counted when their nuclear profiles contained a distinct nucleolus. The $N_V$ was calculated from:

$$N_V = N_A/(D+T)$$

where $N_A$ is the number of neurons per unit area of section, D is the mean diameter of the nucleolus and T is section thickness. The total number of neurons for each nucleus was calculated using estimates of $N_V$ and volume. For individual neurons the profile areas of the cell body were measured in the plane of focus which contained the nucleolus from 100 randomly selected neurons in each nucleus. The statistical significance of direct comparisons between heterozygous mice and wild type controls was determined using Student's t-test.

EXAMPLE 1

Alternate Splicing of mhd

Figure 5:
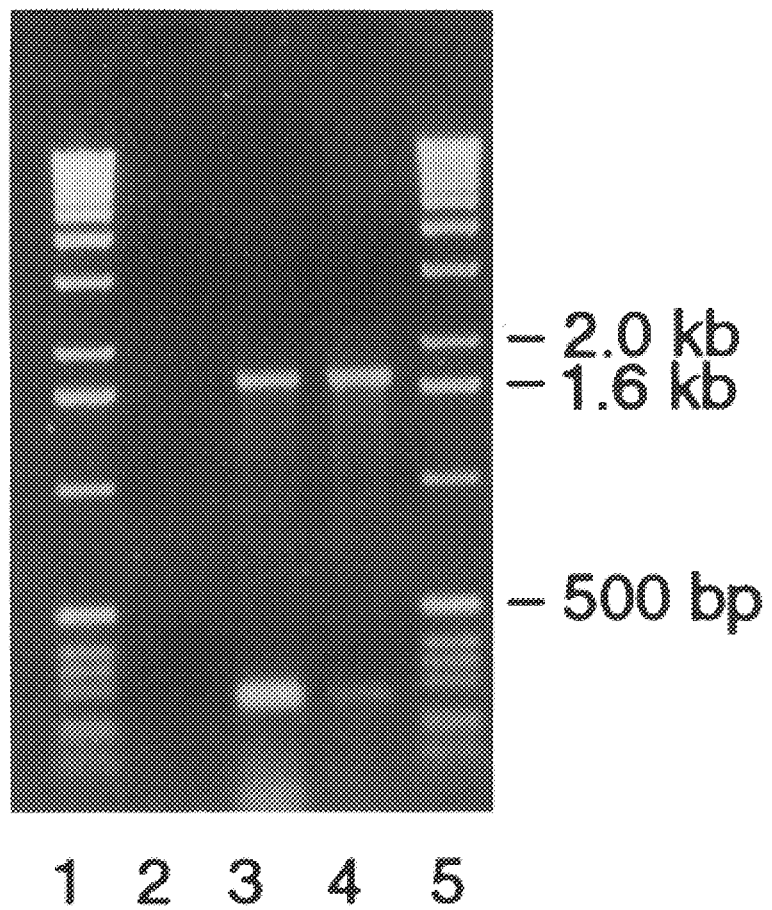
FIG. 5 shows an ethidium bromide stained agarose gel showing the two altered sized PCR products (1.7 kb and 0.3 kb) from human and mouse RNA. RT-PCR was performed using mouse primers MG7 and MG8 and homologous human primers HG7 and HG8 respectively. Lane 2: negative control; Lane 3: RT-PCR of human frontal cortex total mRNA; Lane 4: RT-PCR of mouse total brain mRNA; Lane 1 and 5: DNA size marker (1 kb ladder).

In order to bridge a gap of about 2.7 kb (between nt 2700 and 6400), RT-PCR of mouse brain mRNA was performed and identified the appropriately sized band which spanned this gap. In addition, a second fragment 1.4 kb smaller than the expected band size was also generated (FIG. 5). Both PCR products in the mouse were cloned and sequenced revealing that the larger fragment spanned the gap and aligned correctly with ends of the cDNAs adjacent to the missing region. The sequence of the second shorter product could also be precisely aligned but was missing the sequence between 4678 and 6117. The exon intron boundaries of the HD gene have not been defined but this could indicate exon skipping that resulted from alternate splicing of this particular region of the mouse mRNA (FIG. 1).

To confirm this finding, both mouse and human brain mRNA was analyzed by RTPCR using the flanking primer pairs as indicated (HG7, HG8) (FIG. 5). At the same time, several cDNAs were identified which extended into the gap of 2.7 kb. Amplification revealed two major products of 1.7 and 0.3 kb in sizes apparently representing messages with and without the 1.4 kb portion in both species (FIG. 5). Both mouse and human HD proteins would then be predicted to have at least two isoforms based on the presence (isoform A) or absence (isoform B) of this sequence. Isoform A (mhdproA) is predicted to be 480 amino acids larger than B (mhdproB) with an estimated size difference of approximately 54 kilodaltons and predicted protein size of approximately 294 kilodaltons.

Patterns of Expression of mhd

Figures 4A, 4B:
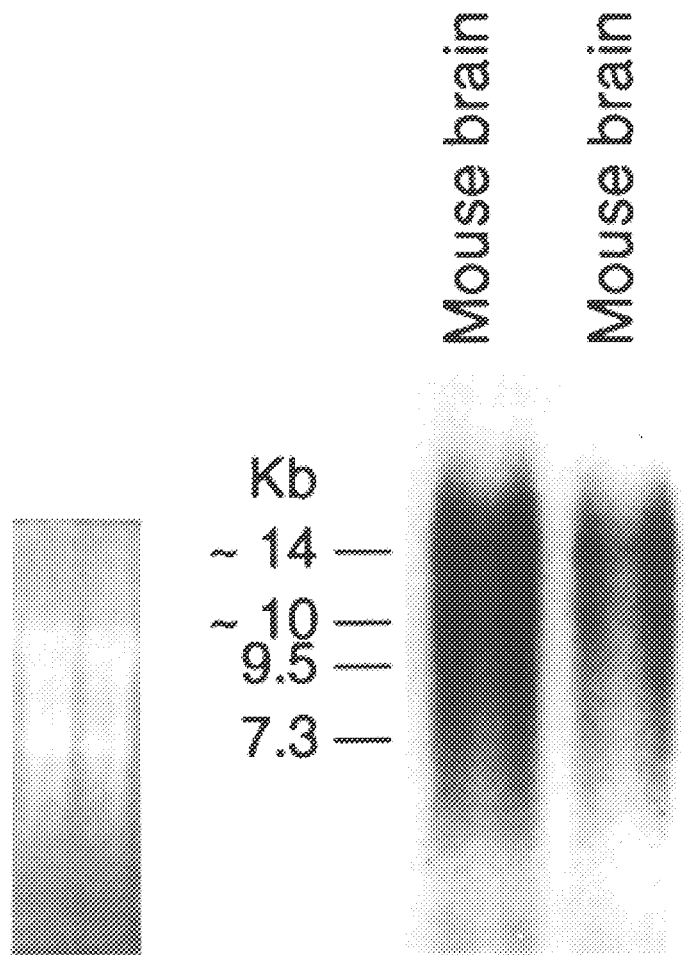
FIGS. 4A–4B show northern blot analysis of mouse brain mRNA. Lane A shows an ethidium stained gel; in Lane B hybridization with mhd 896 reveals two bands of about 10 and 14 kb in mouse brain mRNA.

RT-PCR using primers mG3 and mG4 generated a product seen in different mouse tissues including stomach, heart, testis, adipose tissue, muscle, spleen and brain. RNA analysis revealed that there are two different sized transcripts in mouse brain (FIG. 4).

Between Species Conservation

Figure 6:
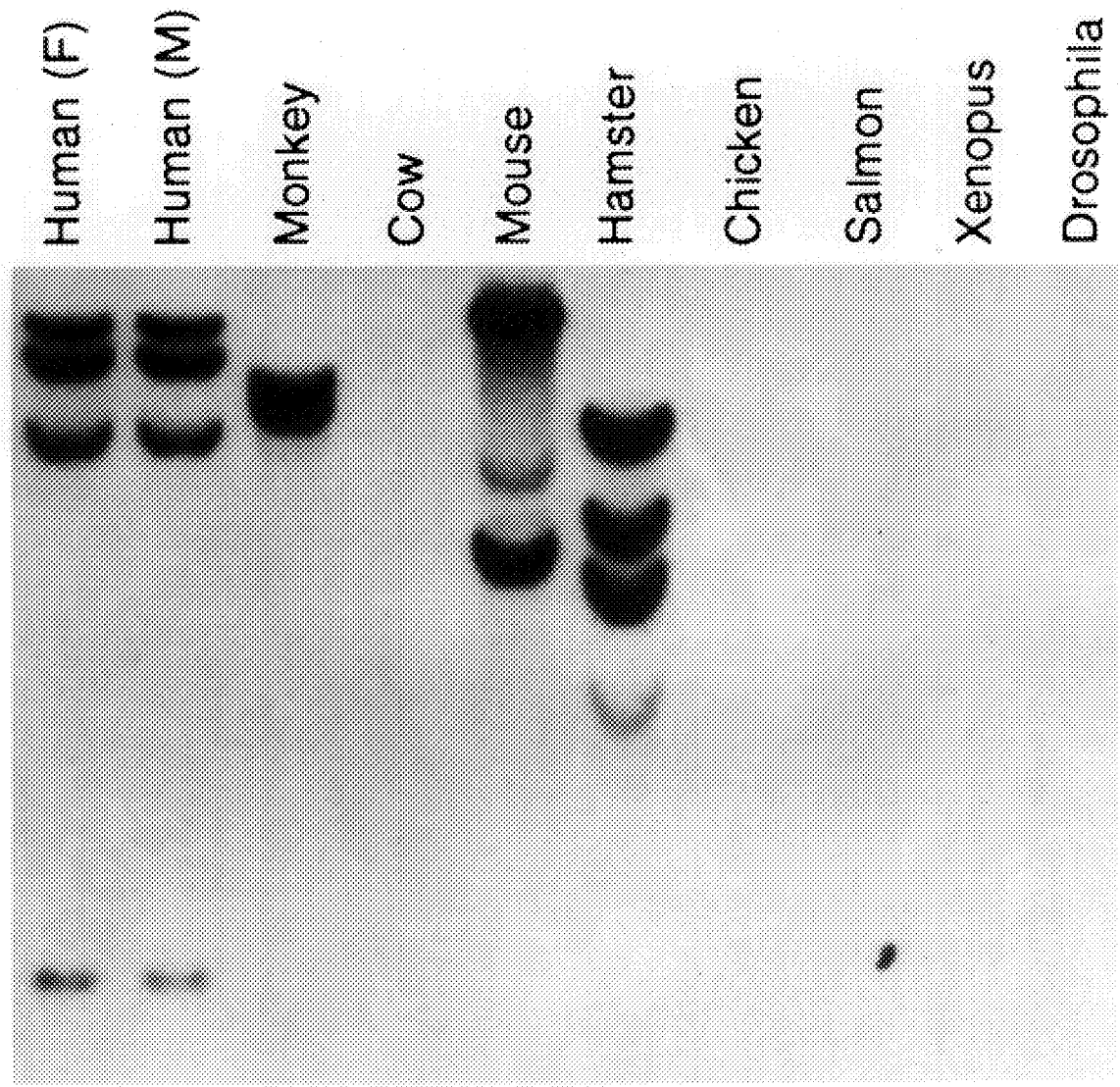
FIG. 6 shows Southern blot analysis of DNA from different species hybridized to mhd 896, a 3' mouse cDNA which reveals strong conservation between mouse, human, monkey and hamster. The concentration of DNA in all lanes was equivalent.

Hybridization with mhd 896 (FIG. 6), revealed strong conservation for this gene between human, mouse, monkey, and hamster but appeared less conserved in lower organisms including chicken, salmon, xenopus, and Drosophila DNA (FIG. 6). This experiment cloned and analyzed the coding regions and the 5' and 3'UTR of the murine HD gene. The murine HD open reading frame show marked conservation at both the nucleotide sequence (identity—86%) and amino acid sequence level (identity—90%). Southern blot analysis revealed that this gene is likely to be highly conserved in related species including monkey and hamster. Both the CAG and CCG trinucleotide repeats are also conserved in the mouse. Further, we have demonstrated that the CCG trinucleotides are also polymorphic in murine DNA. To our knowledge, this is the first observation of a trinucleotide repeat of variable length in a protein-encoding portion of a murine gene.

While the number of CCG repeats in mhd cDNA is a similar size to that seen in the human, the CAG length is notably shorter. The difference in number of triplets and therefore predicted amino acids is surprising given the overall high conservation observed. The CAG trinucleotide represents a perfect repeat of a CAG trinucleotide. The stretch of 7 CAG repeats is interrupted at the third triplet by CAA. When the CAG repeat length is interrupted as in the mouse, this sequence may be less susceptible to expansion than an allele with the perfect repeat.

The median CAG repeat length on normal human chromosomes is 19 with a range between 10 and 35 repeats, whilst the median seen in affected persons with HD is 42 with a range from 37 to 121 repeats. On average a doubling of the CAG repeat length on human chromosomes is therefore sufficient to be associated with selective neuronal death. Doubling the repeat size of the CAG in the mouse from the usual 7 triplets to approximately 14 results in consequences of repeat expansion in terms of the neuronal injury and cell death.

The CGG triplet (associated with fragile X syndrome—1) is conserved in the 5' UTR of the murine homologue of the gene (fmr—1) but also consists of fewer triplet repeats (8 repeats) than found (mean—30) on normal human chromosomes. Similarly, the CTG repeat seen in the 3' end of the human gene associated with myotonic dystrophy (between 5–30 repeats on normal human chromosomes) is seen in the mouse homologue, but in 2 of 5 triplets the CTG is replaced by CAG. Polymorphisms have not been described in either mouse homologues of these two genes.

Detailed sequence analysis of the mouse cDNA has provided evidence that the CAG repeat is contained within the coding sequence of the HD protein. This is different from fragile X syndrome and myotonic dystrophy, where the trinucleotide repeat is contained in the 5' and 3' untranslated regions, respectively. HD appears similar to SBMA where the CAG expanding triplet is also contained within the coding region of the androgen receptor gene close to the start site of the protein. Deletions with loss of function in the androgen receptor gene lead to androgen insensitivity. In contrast CAG repeat expansion in this same gene leads to SBMA. It is likely therefore that the CAG expansion in some way results in either overexpression or a gain of function of the androgen receptor gene. Similarly, demonstration that the CAG repeat is contained within the coding region of the HD gene which results in additional glutamine residues in this protein of affected persons would suggest that altered function of a gene product as opposed to decreased expression is likely to result in the HD phenotype.

We have previously demonstrated that the human HD gene is represented by two transcripts in most tissues. Both transcripts are also surprizingly observed in mouse brain. In humans, a major contribution to the altered transcript size is differential polyadenylation which accounts for 3.5 kb of difference. We have identified alternate splicing as another factor contributing to different sized transcripts in the HD gene. It is likely that alternate splicing results in exon skipping leading to production of transcripts differing by 1.4 kb. Both alternative splicing as well as differential polyadenylation are factors resulting in different sized transcripts of the HD gene in different tissues and related species.

We have cloned and analyzed the mouse hd cDNA in the development of a mouse model for HD to aid in the elucidation of the molecular pathogenesis of HD. We have shown that the mouse gene is highly conserved and contains a shorter CAG repeat compared to the human HD gene. By appropriate genetic manipulation, the CAG repeat in the mouse HD gene may be expanded in excess of 14 to provide a transgenic mouse exhibiting Huntington Disease. Furthermore, identification of different sized mRNAs likely due to alternate splicing predicts more than one isoform for the HD protein. The analysis of mhd cDNA allows the development of specific antibodies and cDNA probes to assess the cellular and subcellular distribution and developmental expression of this gene in the mouse.

EXAMPLE 2

General Methods

The general techniques used in extracting the genome, preparing and probing a cDNA library, sequencing clones, constructing expression vectors, transforming cells, and performing immunological assays and the like, are known in the art and laboratory manuals are available describing those techniques. However, as a general guide, the following sets forth specific information with respect to the above.

1. Host & Control Sequences

Both prokaryotic and eukaryotic systems and their viruses may be used to express the HD encoding sequences; for example, prokaryotes may be represented by various strains of *E. coli,* Bacillus or Pseudomonas. Eukaryotic hosts include yeast and mammalian cells in culture systems. Yeast compatible vectors employing, for example, the 3$\mu$ origin of replication of Brach, J. R. *Meth. Enz.* (1983) 101:307, or other yeast compatible origins of replications (see, for example, Stinchcomb, et al. *Nature* (1979) 282:39, and Clarke, L., et al. *Meth. Enz.* (1983) 101:300) may be used which will result in incorporation of an appropriate fragment into the host cell genome. Control sequences for yeast promoters for the synthesis of glycolytic enzymes including the promoter for 3 phosphoglycerate kinase (Hintzeman et al., *J. Biol. Chem.* (1980) 255:2073) may be employed.

It is also, of course, possible to express genes encoding polypeptides in eukaryotic host cell cultures derived from multicellular organisms. Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral (1978), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitope into the host genome.

2. Transformations

Transformation may be by any known method for introducing polynucleotides into a host cell, including, for example, packaging the polynucleotide in a virus and transducing a host cell with the virus, and by direct uptake of the polynucleotide. The transformation procedure depends upon the host to be transformed.

3. Vector Construction

Vector construction employs standard ligation and restriction techniques which are known in the art. Isolated plasmids, DNA sequences, or synthesized oligonucleotides are cleaved, tailored and religated in the form desired.

Site-specific DNA cleavage is performed by treating with suitable restriction enzyme under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hrs at 37° C. After incubation with the restriction enzyme, protein is removed by phenol/chloroform extraction and the DNA recovered by precipitation using polyacrylamide or agarose gel electrophoresis techniques, according to the general procedures found in Methods in Enzymology (1980) 65:499–560.

Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of the ligation mixture, the vector fragment is often treated with bacterial alkaline phosphates (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as *E. coli,* and successful transformants selected by, for example, antibiotic resistance, and screened for the correct construction.

4. Construction of Desired DNA Sequences

Synthetic oligonucleotides may be prepared using an automated oligonucleotide synthesizer as described by Warner (1984). If desired the synthetic strands may be labelled with $^{32}$P-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into a phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions which permit hybridization with the correct strand, but not with the unmodified sequence. The sequences which have been identified by hybridization are recovered and cloned.

5. Hybridization with Probe

There are simple procedures well known in the art in which probes may be synthesized. The usual technique is to use a highly labelled radioactive probe of RNA or DNA, whose hybridization with the gene is assayed by autoradiography (Levin et al., Genes III, 1987 John Wiley & Sons, 359).

EXAMPLE 3

Protocol for Protein Purification

As discussed with respect to the DNA sequence of FIG. 1, analysis of the sequence of the overlapping cDNA clones predicted an unprocessed polypeptide of at least two isoforms, Isoform A mhdproA and Isoform B mhdproB. Isoform A is predicted to be 480 amino acids larger than B with an estimated size difference of 54 kilodaltons and predicted protein size of approximately 294 kilodaltons. As later described, due to polymorphisms in the protein, the molecular weight of the protein can vary due to possible substitutions or deletion of certain amino acids. It is also understood that the functional protein in the cell will be similar to the unprocessed polypeptide, but may be modified due to cell metabolism.

Protein Purification

The HD protein can be purified by methods selected on the basis of properties as revealed by its sequence. It is first isolated using established methods. Any peripheral proteins may be removed by extraction with high salt concentrations, high pH or chaotropic agents, such as lithium, diidosalicyate. All of the integral proteins remaining, including the HD protein are then solubilized using a detergent such as octylgilucoside, or other compounds of similar action. Making use of the nucleotide binding domains of HD, sibacron-blue affinity chromatography is then used to bind the HD protein and remove it from other integral proteins of the detergent stabilized mixture. If HD is a glycoprotein differential electrochromatography can bring about further purification. Final purification to homogeneity is then achieved using other standard protein purification procedures, such as ion exchange chromatography, cell permeation chromatography, adsorption chromatography or isoelectric focusing as necessary. Alternatively, use is made of single step purification procedures, such as immunoaffinity chromatography using immobilized antibodies to the HD protein or fragments thereof, or preparative polyacrylamide gel electrophoresis using advanced instrumentation such as the Applied Biosystems "230A HPEC System".

In addition to purification from tissues and cells in which the HID tissue is highly expressed, similar procedures are used to purify HD from cells transfected with vectors containing the HD gene (cDNA), as described above. Protein products resulting from expression of modified versions of the cDNA sequence are purified in a similar manner. Criteria of the homogeneity of protein so provided include those standard to the field of protein chemistry including one and two-dimensional gel electrophoresis and N-terminal amino acid determination. The purified protein is used in further physical biochemical analysis to determine features of its secondary and tertiary structure, to aid in the design of drugs to promote the proper functioning of the mutant HD forms. In preparation for use in protein therapy, the absence of potentially toxic contaminating substances is considered.

EXAMPLE 4

Antibodies to Detect HD in Accordance with Standard Procedures

Antibodies within the IID protein will provide extensive information on the characteristics of the protein and other valuable information which includes:

1) To enable visualization of the protein in cells and tissues in which it is expressed by immunoblotting ("Western Blots") following polyacrylamide gel electrophoresis. This allows estimation of the molecular size of the mature protein including the contribution from the cells of post translationally added moieties including oligosaccharide chains and phosphate groups, for example. The antibodies can also be used to provide another technique in detecting any of the other HD mutations which result in a synthesis of a protein with an altered size.

2) The structure function relationships of portions of the protein can be examined using specific antibodies. For example, it is possible to introduce into cells antibodies recognizing each of the charged cytoplasmic loops which join the transmembrane sequences as well as portions of the nucleotide binding folds and the R-domain. The influence of these antibodies on functional parameters of the protein provide insight into cell regulatory mechanisms and potentially suggest means of modulating the activity of the defective protein in a HD patient.

3) Antibodies with the appropriate avidity also enable immunoprecipitation and immuno-affinity purification of the protein. Immunoprecipitation will facilitate characterization synthesis and post translational modification including ATP binding and phosphorylation. Purification will be required to study protein structure and for reconstitution of its function as well as protein based therapy.

In order to prepare the antibodies, fusion proteins containing defined portions of HD polypeptides can be synthesized in bacteria by expressing corresponding DNA sequences in a suitable cloning vehicle whereas smaller peptides may be synthesized chemically. The fusion proteins can be purified, for example, by affinity chromatography on glutathione-agarose, and the peptide coupled to a carrier protein, mixed with Freund's adjuvant and injected into rabbits.

Thus, it is possible to raise monoclonal antibodies specific for both fusion proteins containing portions of the HD protein and peptide corresponding to short segments of its sequence. Monoclonal antibodies can be similarly raised to other domains of the HD protein.

As for the generation of polyclonal antibodies, immunogens for the raising of monoclonal antibodies (mABs) to the HD protein are bacterial fusion proteins containing portions of the HD polypeptide or synthetic peptides corresponding to short (12–25 amino acids in length) segments of the sequence. The essential methodology is that of Kohler and Milstein.

Balb/C mice are immunized by intraperitoneal injection on several occasions with 500 μg of pure fusion protein of synthetic peptide incomplete Freund's adjuvant, followed at 14 days, 21 days and a fourth after 28 days. Individual animals so immunized are sacrificed one, two and four weeks later following the final injection. Spleens are removed, their cells disassociated, collected and fused with Cp2/O-Ag14 myeloma cells according to Gefter et al. The fusion mixture is distributed in cultural medium selective for the propagation of fuse cells which are grown until they are about 25% confluent. At this time, culture supernatants are tested for the presence of antibodies reacting with a particular HD antigen. An alkaline phosphatase labelled anti-mouse second antibody is then used for detection of positives. Cells from positive culture wells are then expanded in culture, their supernatants collected for further detesting and the cells stored deep frozen in cyroprotectant-containing medium. To obtain large quantities of mAB, producer cells are injected into the peritoneum at $5 \times 10^6$ cells per animal, and ascites fluid is obtained. Purification is by chromatography on protein G- or protein A-agarose. Reactivity of these mABs with the HD protein is confirmed by HD get electrophoresis of tissues isolated from cells in which it is expressed and immunoblotting.

In addition to the use of monoclonal antibodies specific for each of the different domains of the HD protein to probe their individual functions, other mABs can be developed, which can distinguish between the normal and mutant forms of HD protein.

Antibodies capable of this distinction are obtained by differentially screening hybridomas from paired sets of mice immunized with peptide containing the normal CAG repeat section or the peptide containing the expanded CAG repeat section. mABs capable of recognizing the other mutant forms of HD protein are obtained using similar monoclonal antibody production strategies. Antibodies to normal and other versions of HD protein and of any segment thereof can be used in diagnostical immunocytochemical and immunfluoresence light microscopy and immunoelectron microscopy to demonstrate a tissue, cellular and subcellular distribution of IID within the organs of HD patients, carriers and non-HD individuals.

Antibodies can be used to therapeutically modulate by promoting the activity of the HD protein in HD models and in cells of HD models. Possible modes of such modulation might involve stimulation due to cross-linking of HD protein molecules within multivalent antibodies.

Antibodies can be used to direct the delivery of therapeutic agents to the cells which express defective HD protein in HD. For this purpose, the antibodies may be incorporated into a vehicle, such as a liposome, with the therapeutic agent such as a drug or the normal gene.

The transgenic mouse HD model is useful in various antibody test programs.

EXAMPLE 5

Targeted Disruption of the Hdh Gene to Develop a Mouse Model

A genomic library from the 129/Sv mouse strain was screened with murine cDNA clone encompassing exon 5 (Lin et al., 1994). Several clones were recovered and restriction mapped in detail and exon intron boundaries were sequenced (Lin et al., 1995).

To create a disruption in exon 5 of the Hdh gene (Hdh⁻ex5), we generated the targeting construct pHdhNeo6 (FIG. 7A) by deleting a 600 bp EspI fragment encompassing approximately half of exon 5 plus intron 4 sequences and replacing it with a PGKneobpA cassette. Disruption of murine exon 5 results in stop codons in all reading frames. The locations of the PCR primers (P6 and P7) used to screen for homologous recombination and the genomic probe used to confirm this are also given. Note that the insertion of the Neo cassette at exon 5, leads to an increase in the size of the HindIII and EcoRI fragments encompassing this genomic region (R=EcoRI, H-HindIII, X=XbaI, E=EspI).

Screening for Homologous Recombination

Figure 1A:
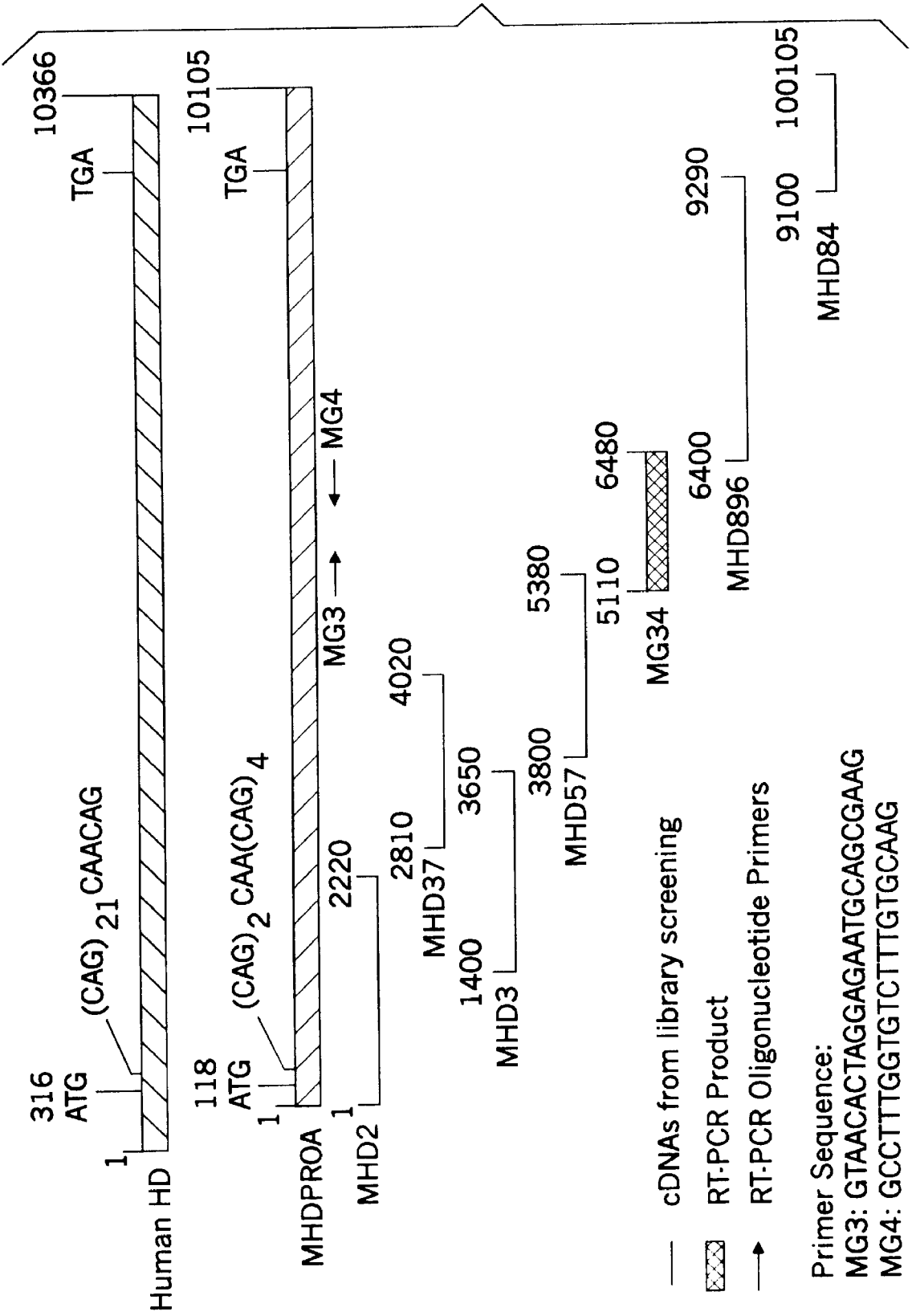
FIG. 1A is the murine HD homologue schematic map showing 6 overlapping mouse cDNA clones.
Figure 1B:
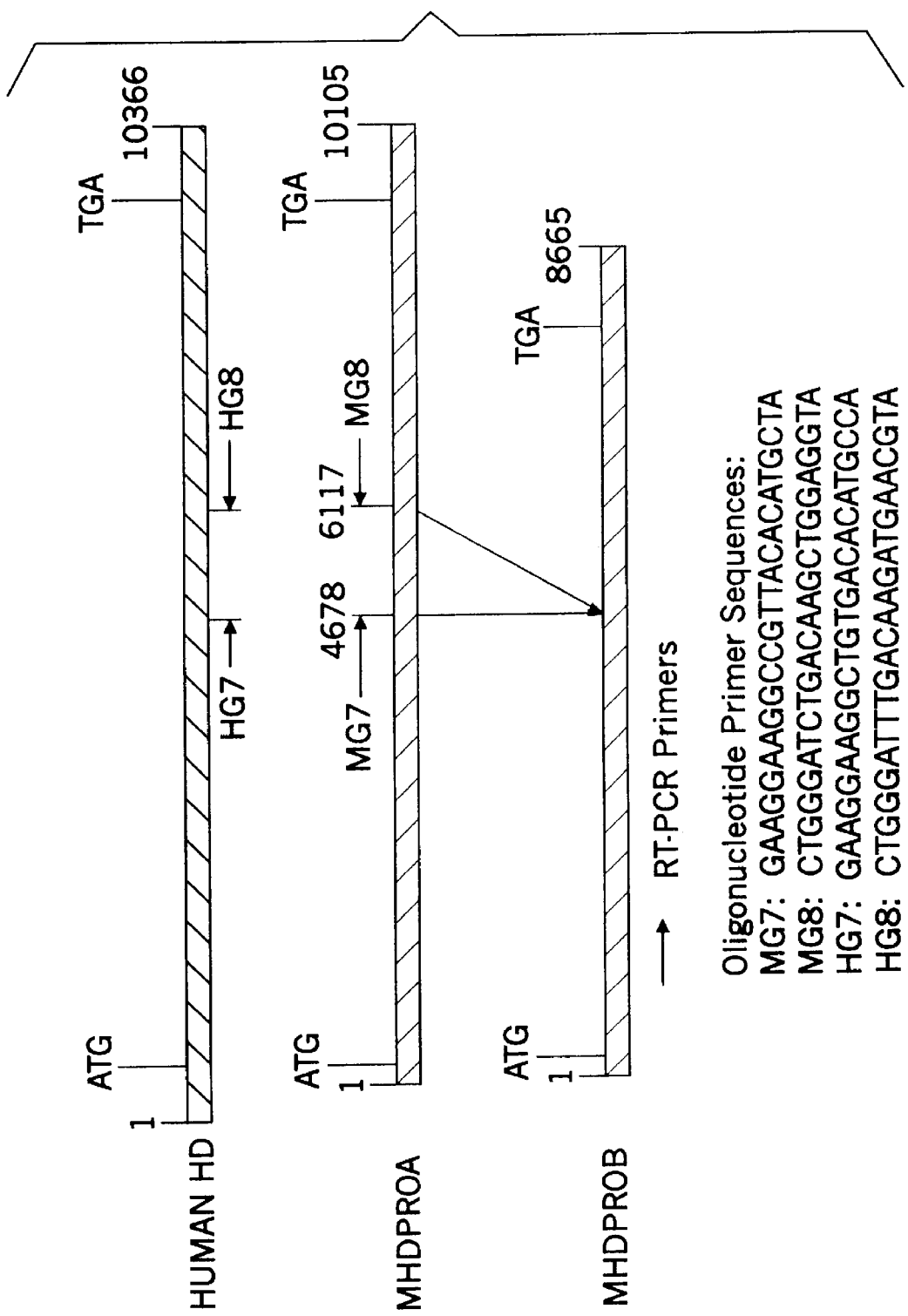
FIG. 1B shows the murine HD homologue RT-PCR product encompassing 10105 bases.

A total of 360 G418 resistant colonies were picked and screened by PCR using a Neo specific primer (P6) and a primer (P7) flanking the integration site (FIG. 1A). The expected size fragment (1.3 kb) was detected in 5 pools corresponding to ES clones 4.4 (lane 1), 35.3 (lane 5), and 35.8 (lane 6). This product was detected in the positive control (lane 9) but not in the two negative controls containing mouse genomic DNA (lane 8) and no DNA (lane 10) (FIG. 1B). Individual clones corresponding to each positive pool were separately screened by PCR. Six clones were identified indicating a targeting frequency of 1 in 60 G418 resistant clones (6/360).

Figure 7A:
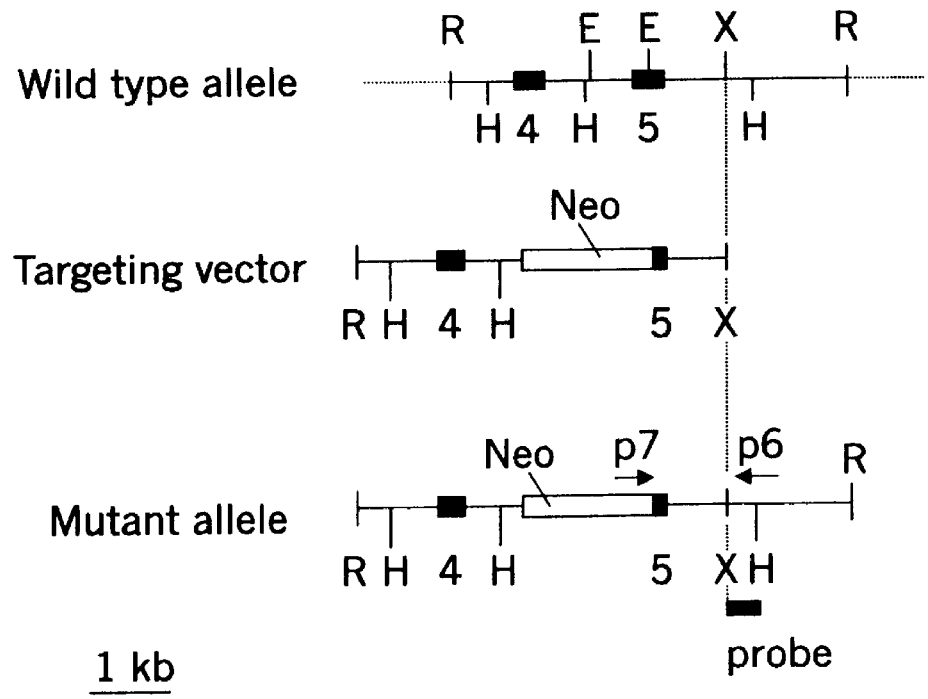
FIG. 7A depicts the targeted disruption of the murine HD homologue gene, and shows the targeting vector and its relationship to the wild type allele. The relative positions of exons 4 and 5 are as indicated. The targeting vector was generated by replacing a 600 bp EspI fragment encompassing a portion of exon 5 plus part of intron 4 with a PGKneobpa cassette. The locations of the PCR primers (P6 and P7) used to screen for homologous recombination and the genomic probe used to confirm this are also given.
Figure 7B:
FIG. 7B: DNAs derived from clonal ES cell lines were screened by PCR using primers P6 and P7. The expected 1.3 kb PCR product was detected in lanes corresponding to ES clones 4.4 (lane 1), 35.3 (lane 5), and 35.8 (lane 6).
Figure 7C:
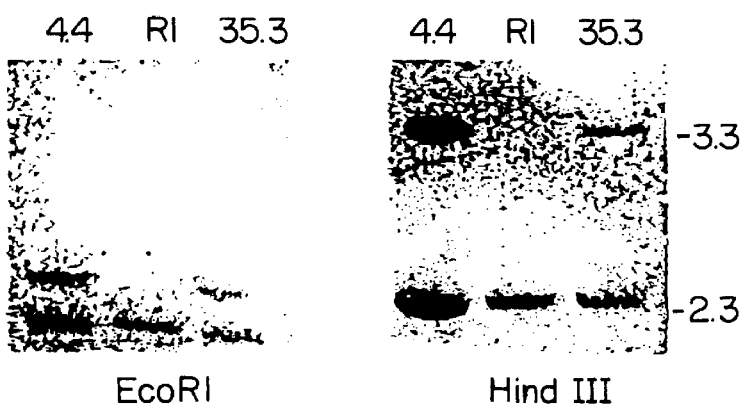
FIG. 7C depicts EcoRI and HindIII digests of clones 4.4 and 35.3 hybridized with a genomic probe (as in FIG. 7A).

Three independently targeted ES cell lines were established and the targeting event was confirmed in each by southern analysis. For each cell line EcoRI and HindIII digests were performed followed by hybrid isation using a 600 bp genomic probe derived from sequences outside the region of homologous recombination (FIG. 7A). The predicted size for the digested fragments associated with the wild type allele are 5.4 kb and 2.3 kb, respectively. The insertion in exon 5 results in a corresponding increase in fragment lengths from 5.4 kb to 6.4 kb for EcoRI and from 2.3 kb to 3.3 kb for HindIII (see FIG. 7C). In the non-transfected control, R1, only the wild type allele was detected. In the targeted cell lines 4.4, 35.3 and 35.8 (data not shown) both wild type and mutant fragments were observed at equivalent intensities (FIG. 7C).

Generation of Chimeric Mice

Figure 7D:
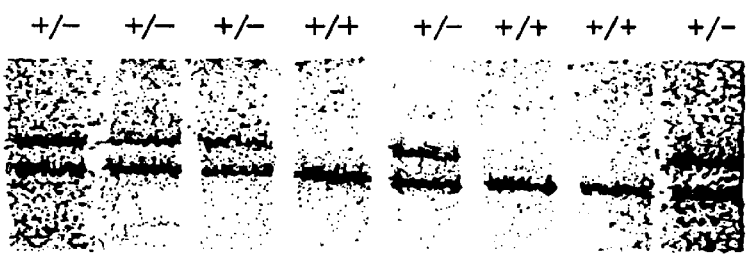
FIG. 7D: Agouti offspring of chimeric mice were assessed for germ line transmission by digesting their DNAs with EcoRI, followed by hybridization with a genomic probe (as in FIG. 7A). Thus, wild type (+/+) and heterozygous mice were identified.

ES cells from each cell line (4.4, 35.3, 35.8) carrying the targeted Hdh mutation were injected into C57BL/6J blastocysts and implanted into pseudopregnant foster mothers. Male chimeras were bred to either C57BL/6J or chimeric females. All three clones generated high levels of chimerism (typically at least 70%) and germ line transmission was achieved for each clone (see Table 1). Approximately half the agouti pups were heterozygous for the mutation (+/−) and half were wild type (+/+) (FIG. 7D).

RT PCR Analysis of Heterozygous Mice

In order to confirm that the targeted mutation in exon 5 results in a null allele, an RT-PCR reaction was performed on RNA from brains of heterozygous mice and a wildtype mouse. RNA from two female heterozygous mice originating from different ES cell lines (4.4 and 35.3) was reverse transcribed using a gene specific primer (p16) and random hexamers. Briefly, RNA was extracted from two adult heterozygous (+/−) mice derived from ES cell lines 4.4. (lanes 2 and 5) and 35.3 (lanes 3 and 6 (FIG. 8). As a control, RNA from a wild type mouse (+/+) (lanes 1 and 4) was used. The reverse transcription reaction was carried out using a gene-specific primer (lanes 1–3) and random hexamers (lanes 4–6). The RT product was amplified using primers derived from exons 4 and 6 (see Experimental Procedures). The expected 248 bp product is seen in all lanes except the no DNA negative control (lane 8). However, in lanes 2, 3, 5 and 6 corresponding to RT products derived from the heterozygous mice, a short PCR product (167 bp) is seen.

Figure 8C:
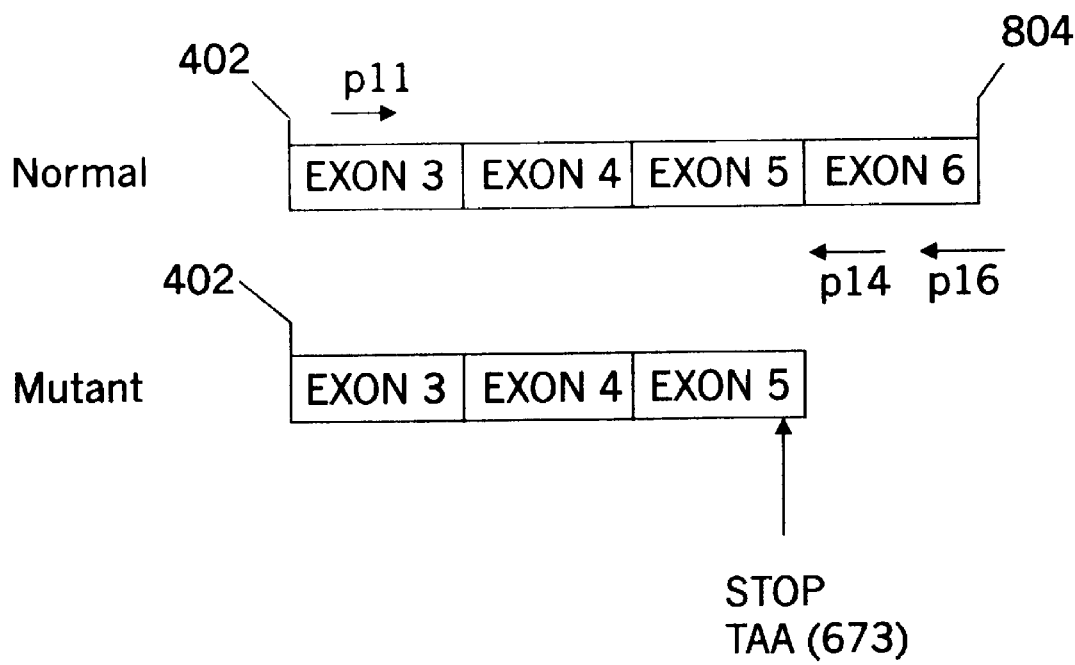
FIG. 8C illustrates that in the wild type allele all exons are correctly spliced whereas in the mutant allele exon 5 is skipped, leading to a premature termination of the translated protein in exon 6. The RNA was reverse transcribed with primer P16 and PCR amplified with primers P11 and P 14.
Figure 8A:
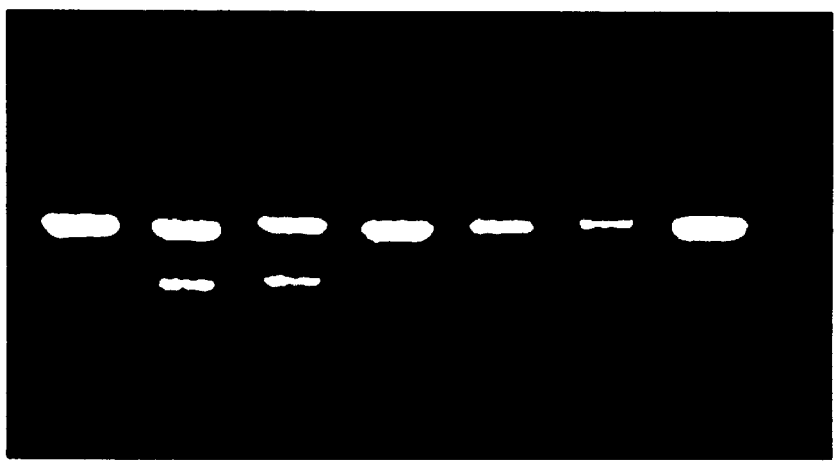
FIG. 8A depicts RT PCR analysis of heterozygous mice. RNA was extracted from two adult heterozygous (+/–) mice derived from ES cell lines 4.4. (lanes 2 and 5) and 35.3 (lanes 3 and 6). As a control, RNA from a wild type mouse (+/+) (lanes 1 and 4) was used.
Figure 8B:
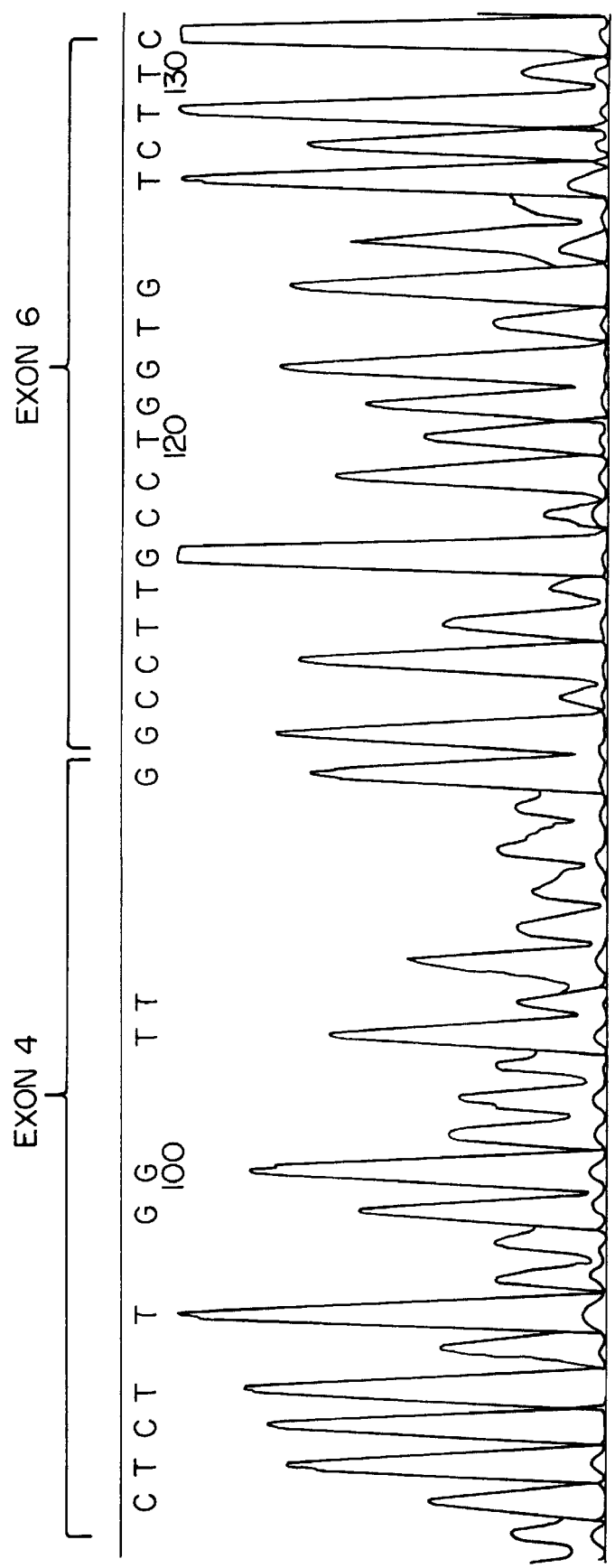
FIG. 8B: sequencing of the shorter (167 bp) RT-PCR product in heterozygous mice confirms that exon 5 is skipped in the mutant allele.

The RT product was used as a template for PCR amplification using primers from exon 3 (p11)and exon 6 (p14). The expected 248 bp product was generated from RNA of both the heterozygous mice and the control mouse (FIG. 8A). In the heterozygous mice a shorter product (167 bp) was generated as predicted, presumably due to skipping of exon 5 (see FIG. 8). In order to confirm this, this product was subcloned and sequenced (FIG. 8B) revealing that the mutation leads to skipping of exon 5 and a frame shift resulting in a stop codon immediately downstream of the targeting event at nucleotide 673 which results in a severely truncated protein of approximately 20 kD (FIG. 8C).

Western blot analysis of brains from heterozygous mice using an antibody (AP78) directed against the N terminus of the protein (Sharp et al., in press), revealed a ~340 kD band indicative of the product from the normal allele, and a smaller protein of approximately 20 kD which could represent the truncated gene product.

Disruption of Hdh Mutation Results in Early Embryonic Lethality

Mice heterozygous for the targeted mutation were intercrossed but no live homozygous Hdh-$^{ex5}$ mice were produced among 225 newborns ($p<10^{-6}$) (Table 2A), derived from all three independently targeted ES cell clones. The number of heterozygotes to wildtype mice were present in the ratio of approximately 2:1, which allowed us to conclude that the Hdh-$^{ex5}$ homozygotes die in utero.

Figure 9A:
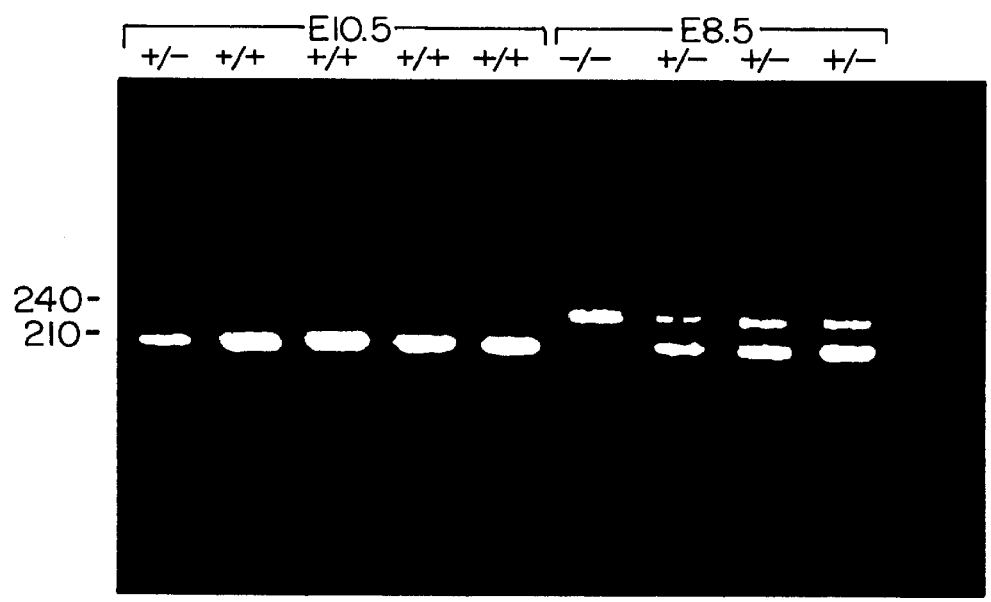
FIG. 9A depicts the genotype analysis of embryos at different stages of gestation. Embryos were were incubated overnight in a lysis buffer including proteinase K and analysed by PCR with primers P8, P9 and P586. The PCR products were run on 2% agarose gels to resolve the wild type (210 bp) and mutant alleles (240 bp).
Figure 9B:
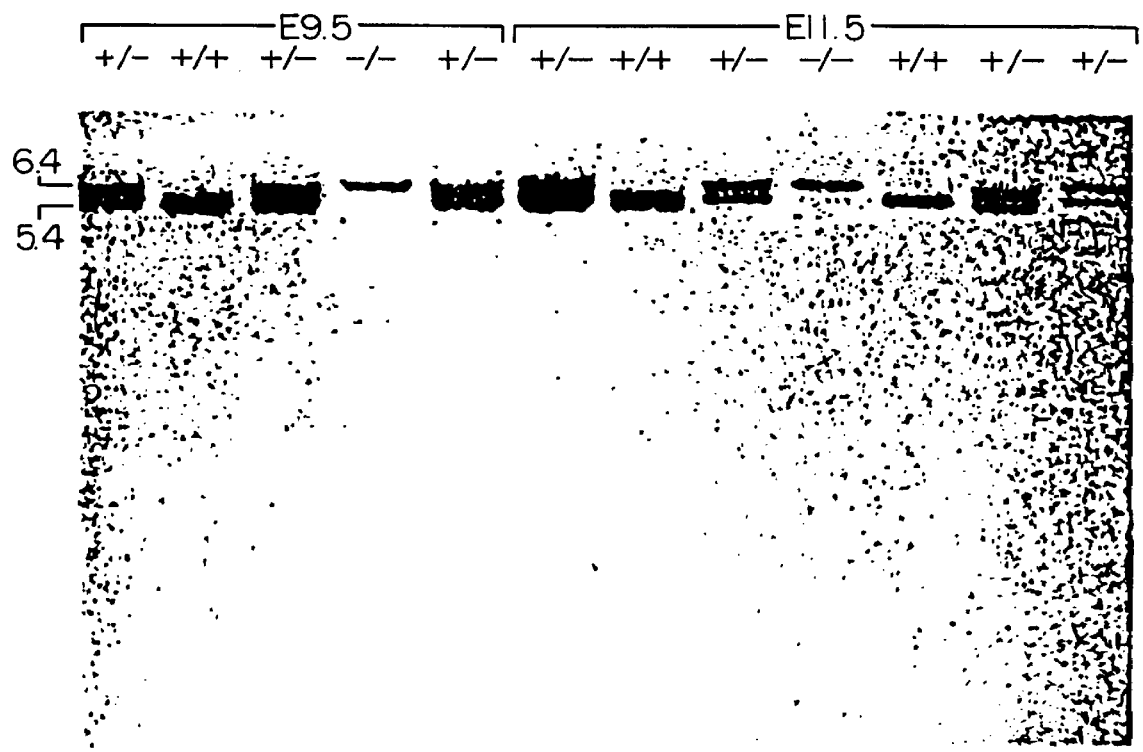
FIG. 9B depicts Southern analysis of DNA from embryos isolated as described elsewhere (Hogan et al. 1986). The DNA was digested with EcoRI, blotted and hybridized with a genomic probe (as in FIG. 7A). The wild type and mutant alleles are associated with fragment sizes of 5.4 kb and 6.4 kb respectively.

To determine the timing of the Hdh-$^{ex5}$ lethality, embryos were analysed at different stages during gestation. From E7.5 to E12.5, 173 decidua analysed contained morphologically normal embryos, whereas the remaining 51 contained nearly or completely resorbed embryos, 35 of which were recovered for genotyping. The embryos were genotyped by Southern blot or PCR analysis (FIG. 9A and 9B).

Embryos were incubated overnight in a lysis buffer including proteinase K and analysed by PCR with primers P8, P9 and P586 (see Experimental Procedures). The PCR products were run on 2% agarose gels to resolve the wild type (210 bp) and mutant alleles (240 bp). For Southern analysis, DNA was isolated as described elsewhere (Hogan et al. 1986). The DNA was digested with EcoRI, blotted and hybridized with a genomic probe (FIG. 7A).

Normal embryos were in the expected ratios for the genotype, +/+ or +/-, but only 4 (2%) phenotypically normal embryos (2 at E7.5) had the -/- genotype. The majority (80%) of resorbed embryos were homozygous for the Hdh-$^{ex5}$ mutation. These data indicate that loss of function of the endogenous Hdh gene results in embryonic lethality during early postimplantation development.

Histological Analysis of Embryos

From E7.5 to E9.5 a high frequency of resorption in the litters of heterozygote crosses was observed (40/187 or 21.3%). At E8.5, the ratio of -/- versus +/+ or +/- resorbed embryos increased indicating that more Hdh-$^{ex5}$ homozygotes were dying.

Figure 10A:
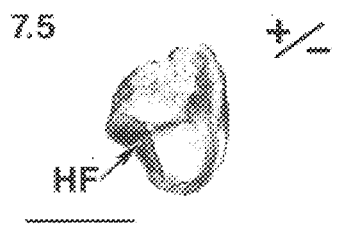
FIG. 10A depicts a heterozygous embryo dissected out of the decidua and genotyped using PCR. Headfolds have begun to form at the anterior end of the embryo. Scale bar is 500 μm. A—allantois; E—embryonic ectoderm; EPC—ectoplacental cone; EN—embryonic endoderm; HF—headfold; H—heart; M—mesoderm, NG—neural groove, RE—resorbing embryo, S—somite.
Figure 10B:
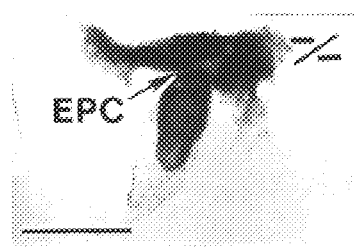
FIG. 10B shows the homozygous littermate of the embryo in panel A. The embryo, which was genotyped using PCR, is very small and underdeveloped. Scale bar is 500 μm.
Figure 10C:
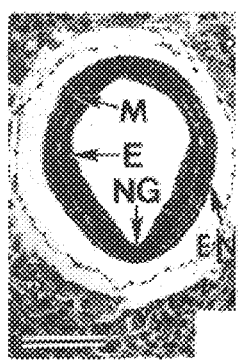
FIG. 10C is a transverse section of a 7.5 day normal embryo. The neural groove has begun to form in this early neurula-stage embryo. Scale bar is 250 μm.
Figure 10D:
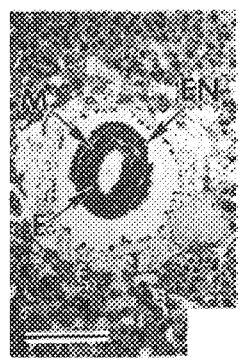
FIG. 10D is a transverse section of an abnormal (E7.5) embryo. Mesoderm has formed around the embryonic ectoderm. The size of the embryo is considerably smaller than the normal embryo shown in FIG. 10C. Scale bar is 250 μm.

Sections from 67 embryos produced by heterozygous intercrosses were examined. Litters ranged in age from 7 to 8.5 days gestation during which time the major events of gastrulation have occurred: elongation of the primitive streak, formation of mesoderm, formation of headfolds and the formation of somites and branchial arches. The abnormal embryos (19/67=28.36%) could be distinguished by their immaturity compared to normal litter mates (compare FIG. 10A and 10B; FIG. 10C and 10D). The disparity in development was most evident in the older litters collected at 7.75 and 8.5 days gestation.

Figure 10E:
FIG. 10E is a parasagittal section of an abnormal (E7.5) embryo, and shows that a small amount of mesoderm has formed in the embryo. However, extraembryonic membranes are fragmented and the process of resorption may be beginning. Scale bar is 250 μm.
Figure 10F:
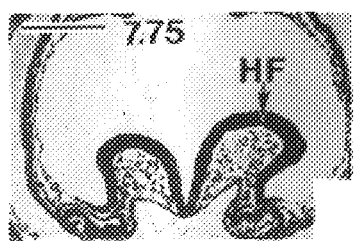
FIG. 10F is a transverse section through the headfold region of a 7.75 day normal embryo. Scale bar is 250 μm.
Figure 10G:
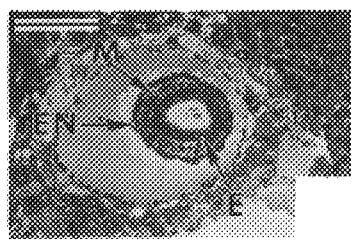
FIG. 10G is a transverse section through an abnormal (E7.75) embryo and shows that mesoderm has formed. However, the ectoderm is not thickened as occurs at the onset of neurulation. Scale bar is 250 μm.
Figure 10H:
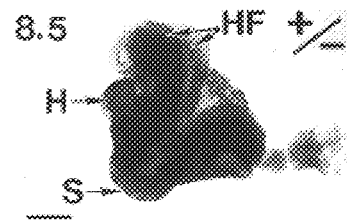
FIG. 10H is a heterozygous embryo (E8.5) dissected out of decidua and genotyped using PCR. Prominent headfolds, heart and somites are visible. Scale bar is 500 μm.
Figure 10I:
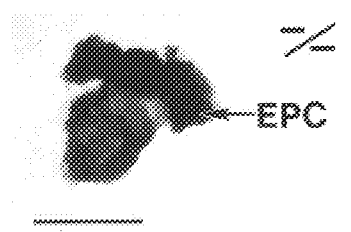
FIG. 10I is a homozygous littermate to the embryo of FIG. 10H, and was genotyped using PCR. The size of the embryo is considerably smaller than its normal littermate. Scale bar is 500 μm.
Figure 10J:
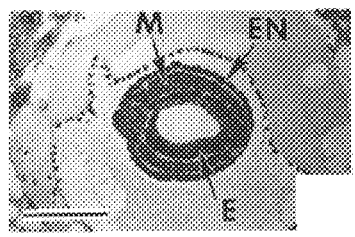
FIG. 10J is a transverse section of an 8.5 day embryo in which development is similar to that of the embryo in FIG. 10I. The embryo is very small and looks similar to abnormal embryos observed at 7.5 and 7.75 days gestation. Mesoderm has formed but neurulation has not begun. Scale bar is 250 μm.
Figure 10K:
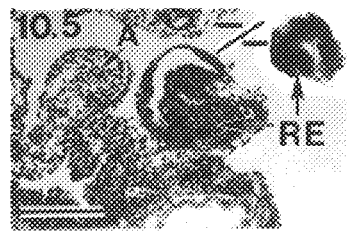
FIG. 10K is a section through a 10.5 day −/− resorbing embryo genotyped using PCR. Inset shows appearance of whole embryo and membranes dissected free from the decidua. Scale bar is 250 μm.

The normal embryos exhibited well developed headfolds and epithelial-stage somites (FIG. 10F, 10H and data not shown) whereas the abnormal littermates had only reached late primitive streak stage (FIG. 10G, 10I). In the developmentally delayed embryos there was no indication that a neural plate had formed (compare FIG. 10C and 10D), although mesoderm had accumulated between the ectoderm and endoderm. The extraembryonic membranes were present in the abnormal embryos in the same arrangement as in normal embryos (FIG. 10E and data not shown). However, the size of the membranes was reduced and a connection between the allantois and the placenta was not achieved. The phenotype of abnormal embryos closely matches that of the dissected, genotyped embryos (compare FIG. 10B and D, FIG. 10I and J). Null mutants deteriorated rapidly after 8.5 days and little structure remained by 10.5 days gestation (FIG. 10K)

Behavioural Assessment

Seven mice heterozygous for the Hdh-$^{ex5}$ mutation and 7 wild type mice from related litters (+/+) were assessed. All mice were male aged 4 months. Mutant mice ate and drank normally and were indistinguishable from controls with respect to body weight, posture, locomotion, rearing, grooming and did not display any signs of ataxia. Mutant mice were distinctly more reactive to handling. For all tests, the experimenter was blind to the genetic status of the animals.

Motor Activity Test

This test assessed spontaneous motor activity in a horizontal plane, as measured by overall level of activity and the habituation to a novel stimulus during each separate 2 hour phase of the test. The mutant mice were significantly more active than controls ($p<0.01$) throughout both phases with no overlap between the groups (in the light phase mutant= 2162±163: control=1557±163: $p<0.05$; dark phase mutant= 1383±133: control=714±133: $p<0.005$) (FIG. 5A). Activity scores of both groups declined significantly across successive 10 minute time bins ($p<0.01$).

T-Maze Alternation Test

This test allows general assessment of simple discrimination learning and short-term memory. Both groups learned this task at the same ($F (2,20)=12.349$, $p<0.001$) rate and reached asymptotic performance of 80% or greater correct responses by the third training day. They also did not differ in mean latency to reach the food cup after release (Hdh-$^{ex5}$ mice=35.6±2.9 s: control mice=39.1±7.1 s), which provides confirmation that mutant mice did not have impairments in locomotion, and that motivation was normal. One animal in both the mutant and control groups did not eat fruit-loops on any trial on the T-Maze, and therefore, their data were not analyzed.

Radial-Arm Maze Test

This provides a direct test of working memory. Control animals quickly learn not to re-visit arms explored previously within a trial and thus acquire the 4 pieces of food with minimum effort. Data from the same two mice which again did not eat in this test, were excluded. Although the performance of the mutant mice, as measured by re-entry errors, was highly variable, the mutant group did not differ from controls and both groups made fewer errors as the experiment proceeded ($F (16,60)=2.757$, $p<0.05$). Hdh-$^{ex5}$ mice made 2.0±0.05 revisit errors on Day 7 compared to 1.0±0.47 errors by the control group.

Morris Water Maze Task

The Morris Water Maze task (Morris, 1981) has been used routinely to study the ability of rodents to acquire spatial information. Measures of path length (cms) and latency (s) to reach a submerged platform were grouped across acquisition and reversal phases. Both groups of mice showed improvement over 6 trials. Analyses of the latency data confirmed that Hdh$^{-ex5}$ mice had acquired the necessary spatial information to locate the hidden platform efficiently (see FIG. 5B). A separate analysis of the path length measurements showed no effect of genotype and a significant effect of trial (F(12,144=17.31, p=0.001) with no significant interaction. Two mutant mice remained motionless for 20–30 s periods during several of the reversal trials, which may have enhanced the latency scores, without increasing path length.

Data from the memory probe trial demonstrated appropriate memory for the location of the platform site by both Hdh$^{-ex5}$ and control mice, reflected by the greater percentage of time spent by both groups in the NW quadrant of the pool (p<0.001) (see FIG. 11C) where the platform had previously been located. Both Hdh$^{-ex5}$ and control mice made a comparable number of crosses over the platform site (FIG. 11D).

Deficits were however, observed when mutants were required to reverse their spatial response by swimming to the hidden platform in a new location (FIG. 11B). Latency data from the Hdh$^{-ex5}$ group were significantly greater than control values on the first, third, fourth and fifth blocks of trials (p<0.01). A second memory probe trial conducted immediately after the 10th reversal trial confirmed the impairment (FIG. 11C). Control mice again spent a significantly greater percentage of the trial swimming in the quadrant in which the platform had been relocated (p<0.01). By contrast, Hdh$^{-ex5}$ mice distributed their swimming time equally across all four quadrants. This difference was highlighted by the finding that control mice crossed the new platform site in the SE quadrant more than twice as frequently as the mutant mice (p<0.05). Normal acquisition and memory of spatial information coupled with the marked impairment seen in the reversal trials, suggests that Hdh$^{-ex5}$ mice have cognitive deficits associated with acquiring or using new information in the face of existing information.

Histology and Morphometry of Brains of Heterozygotes

Two heterozygous mice with the most severe performance deficits were sacrificed for neuropathological examination. The morphology of the central nervous system in the heterozygous mice appeared relatively normal with no signs of gross malformations or obvious developmental abnormalities. Examining the serial Nissl sections revealed no signs of neuronal necrosis, gliosis or inflammation. In the heterozygous mice, there appeared to be a decrease in the size of the subthalamic nucleus (FIG. 12). There were no obvious differences in the morphology of the caudate or putamen (FIG. 13), although there appeared to be a decrease in the number of neurons in the globus pallidus (Table 3).

There were no differences in mean brain weight and the volumes of the caudate putamen, globus pallidus, substantia nigra, hippocampus, corpus callosum and thickness of motor cortex (Table 3). However, the volume of the subthalamic nucleus was found to be significantly reduced in heterozygous mice (t=7.256, df=2, P=0.018). The $N_V$ of neurons did not differ significantly in any of the regions examined. When the total number of neurons in a region was calculated from estimates of neuronal $N_V$ and regional volume, there were significantly fewer neurons (~45%) in the subthalamic nucleus of heterozygous mice (t=6.849, df=2, P=0.021). In the globus pallidus the mean value for total neuron number was 43% less in heterozygous mice compared to controls, but this difference was only of borderline significance (t=4.243, df=2, P=0.051). The mean neuronal profile area did not differ significantly between the two groups in any of the regions examined.

TABLE 1

Generation of chimeric mice and germline transmission of mutant allele
Three independently derived correctly targeted ES clones were injected into blastocyst stage embryos (see Experimental Procedures) to generate chimeric animals. The majority of the chimeric animals had a very high BS cell contribution as determined by the extent of agouti in their coat colour. Generally, only males were selected for further breeding to identify the germ line transmitting animals.

| Clone | Chimera | % Agouti | Sex | Agouti Offspring | Germline Transmission |
|---|---|---|---|---|---|
| 4.4 | 88 | 70% | M | 23/32 | Yes |
|  | 93 | 50% | F | — | — |
|  | 97-1 | 95% | M | 23/23 | Yes |
|  | 97-2 | 90% | M | 24/24 | Yes |
| 35.3 | 94-1 | >95% | M | 23/23 | Yes |
|  | 94-2 | >95% | M | 22/22 | Yes |
|  | 94-3 | >95% | M} | 14/14 | Yes |
|  | 94-4 | 80% | F} | — | — |
|  | 94-5 | 40% | M | 0/18 | No |
|  | 100 | 70% | F | 0/10 | No |
| 35.8 | 109-1 | 90% | M | — | — |
|  | 109-2 | 80% | M | 3/3 | Yes |
|  | 109-3 | 60% | M | 0/21 | No |
|  | 109-4 | 10% | F | — | — |

Table 2: Genotyping of liveborn offspring, normal and resorbed embryos

Heterozygous mice for each of three ES cell lines (4.4, 35.3 and 35.8) were intercrossed and the resulting liveborn offspring were genotyped (Table 2A). In addition, timed matings were set up between heterozygous animals for each clone and both normal and resorbed embryos were collected at different stages of gestation (E7.5 to E12.5) (Table 2B and 2C).

TABLE 2A

| 9/24 Genotyping of Liveborn Offspring | | | |
|---|---|---|---|
| Source (Cell line) | +/+ | +/− | −/− |
| 4.4 | 46 | 80 | 0 |
| 35.3 | 31 | 59 | 0 |
| 35.8 | 4 | 5 | 0 |
| Total | 81 | 144 | 0 |

$X^2 = 73.125$;
df = 2;
$p < 10^{-6}$

TABLE 2B

| Genotyping of Phenotypically Normal Embryos at Different Stages of Gestation | | | |
|---|---|---|---|
| Day of Gestation | +/+ | +/− | −/− |
| 7.5 | 23 | 24 | 2 |
| 8.5 | 16 | 46 | 2 |
| 9.5 | 9 | 16 | 0 |
| 10.5 | 8 | 12 | 0 |
| 11.5 | 2 | 6 | 0 |
| 12.5 | 1 | 6 | 0 |
| Total | 59 | 110 | 4 |

$X^2 = 47.5818$;
df = 2;
$p < 10^{-6}$

TABLE 2C

Genotyping of Resorbed Embryos at Different Stages of Gestation

| Day of Gestation | +/+ | +/− | −/− |
|---|---|---|---|
| 7.5 | 2 | 1 | 2 |
| 8.5 | 1 | 1 | 12 |
| 9.5 | — | 1 | 9 |
| 10.5 | 1 | — | 2 |
| 11.5 | — | — | 2 |
| 12.5 | — | — | 1 |
| Total | 4 | 3 | 28 |

$X^2 = 70.7321$;
df = 2;
$p < 10^{-6}$

TABLE 3

Morphometric Variables[a] of Brains of Heterozygotes for the Hdh$^{-exS}$ mutation and littermates

| | Control (n = 2) | Heterozygotes (n = 2) | p value |
|---|---|---|---|
| Brain Weight (mg) | 400 ± 10 | 430 ± 10 | ns |
| Caudate-Putamen | | | |
| Volume (mm$^3$) | 9.849 ± 0.333 | 8.988 ± 1.188 | ns |
| N$_v$ neurons | 128,748 ± 11,703 | 140,555 ± 21,347 | ns |
| Total neurons | 1,217,788 ± 68,172 | 1,237954 ± 24,882 | ns |
| Neuron profiles ($\mu m^2$) | 108 ± 1 | 100 ± 13 | ns |
| Globus Pallidus | | | |
| Volume (mm$^3$) | 1.075152 ± 0.019443 | 0.817519 ± 0.127867 | ns |
| N$_v$ neurons | 34,831 ± 2,845 | 26994 ± 4986 | ns |
| Total neurons | 37,504 ± 3,736 | 21430 ± 625 | ns |
| Neuron profiles ($\mu m^2$) | 225 ± 1 | 178 ± 13 | ns |
| Subthalamic Nucleus | | | |
| Volume (mm$^3$) | 0.132678 ± 0.005970 | 0.089158 ± 0.000573 | 0.01 |
| N$_v$ neurons | 201,313 ± 2,532 | 170,719 ± 13,906 | ns |
| Total neurons | 26,725 ± 1,538 | 14,729 ± 838 | 0.02 |
| Neuron profiles ($\mu m^2$) | 118 ± 4 | 114 ± 19 | ns |
| Substantia Nigra | | | |
| Volume (mm$^3$), PC | 0.156043 ± 0.004276 | 0.136227 ± 0.015522 | ns |
| Volume (mm$^3$), PR | 0.414868 ± 0.030772 | 0.351587 ± 0.062205 | ns |
| N$_v$ neurons, PC | 21,925 ± 2,635 | 21,272 ± 707 | ns |
| Total neurons, PR | 9,015 ± 419 | 7435 ± 1075 | ns |
| Neuron profiles (mm$^2$) | 209 ± 12 | 195 ± 11 | ns |
| Hippocampus | | | |
| Volume (mm$^3$) | 9.459 ± 0.489 | 10.005 ± 0.957 | ns |
| Motor Cortex | | | |
| Thickness ($\mu m^2$) | 1088 ± 51 | 1083 ± 118 | ns |

[a]Values are given as the mean ± standard error of the mean

TABLE 4

Comparison of the Exon and Intron Size and Splice Site Sequences of the First Five Exons of the Mouse and Human HD Genes*

| Exon | Gene | Exon Size (bp) | 5' Donor Site | Intron | Intron Size (kb) | 3' acceptor site |
|---|---|---|---|---|---|---|
| 1 | Hdh | | GTGAGTCCGGGCGCCGCAGCTC | 1 | ~15 | TTTTCCTCTTGTTTTTTGTAG |
| 1 | HD | | GTGAGTTTGGGCCCGCTGCAGC | 1 | ~10 | TCCTTCTTTTTTTATTTTAG |
| 2 | Hdh | 84 | GTAATTGGCTTTTTAAAAAAAA | 2 | ~7 | TCTCTCTCTCTTTTTTACTTAG |
| 2 | HD | 84 | GTAATTGCACTTTGAACTGTCT | 2 | ~15 | TTTCTCTTCTTTTTTTGCTTAG |
| 3 | Hdh | 121 | GTAAGCGCCCCATAATGATGAT | 3 | ~5 | AGTCTCTTCTATTTCTTTGCAG |
| 3 | HD | 121 | GTAAGAACCGTGTGGATGATGT | 3 | ~7 | AATCTCTTGTGATTTGTTGTAG |
| 4 | Hdh | 60 | GTGGGTGTTTGCTCTGCATTAT | 4 | ~0.5 | ATCACTTGTTAACTCCACTTAG |
| 4 | HD | 60 | GTGGGCCTTGCTTTTCTTTTTT | 4 | ~0.5 | AACCCTCATTGCACCCCCTCAG |

TABLE 4-continued

Comparison of the Exon and Intron Size and Splice Site Sequences of the
First Five Exons of the Mouse and Human HD Genes*

| Exon | Gene | Exon Size (bp) | 5' Donor Site | Intron | Intron Size (kb) | 3' acceptor site |
|---|---|---|---|---|---|---|
| 5 | Hdh | 80 | GTAAGTTGTACCTCTGTATTATTTTTAAGA | | | |
| 5 | HD | 80 | GTAAGTTGTACACTCTGGATGTTGGTTTTT | | | |

*Donor and Acceptor splice sites are from Ambrose et al. (1994).

Although preferred embodiments of the invention are described herein in detail, it will be understood by those skilled in the art that variations may be made thereto without departing from the spirit of the invention or the scope of the appended claims.

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GTAACACTAG GAGAATGCAG CGAAG                            2 5

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCCTTTGGTG TCTTTGTGCA AG                              2 2

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GAAGGAAGGC CGTTACACAT GCTA                           2 4

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:4:

CTGGGATCTG ACAAGCTGGA GGTA 24

(2) INFORMATION FOR SEQ ID NO:5:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

GAAGGAAGGC TGTGACACAT GCCA 24

(2) INFORMATION FOR SEQ ID NO:6:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

CTGGGATTTG ACAAGATGAA CGTA 24

(2) INFORMATION FOR SEQ ID NO:7:

(i) SEQUENCE CHARACTERISTICS:
(A) LENGTH: 10103 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

| | | | | | |
|---|---|---|---|---|---|
| GGTTCCGCTT | CTGCCTGCCG | CGCAGAGCCC | CATTCATTGC | CTTGCTGCTA | AGTGGCGCCG | 60 |
| CGTAGTGCCA | GTAGGCTCCA | AGTCTTCAGG | GTCTGTCCCA | TCGGGCAGTA | AGCCGTCATG | 120 |
| GGAACCCTGG | AAAAGCTGAT | GAAGGCTTTC | GAGTCGCTCA | AGTCGTTTCA | GCAGCAACAG | 180 |
| CAGCAGCAGC | CACCGCCGCA | GGCGCCGCCA | CCGCCGCCGC | CGCCTCCGCC | TCAACCCCCT | 240 |
| CAGCCGCCGC | CTCAGGGGCA | GCCGCCGCCG | CCACCACCGC | CGCTGCCAGG | TCCGGCAGAG | 300 |
| GAACCGCTGC | ACCGACCAAA | GAAGGAACTC | TCAGCCACCA | AGAAAGACCG | TGTGAATCAT | 360 |
| TGTCTAACAA | TATGTGAAAA | CATTGTGGCA | CAGTCTCTCA | GAAATTCTCC | AGAATTTCAG | 420 |
| AAACTCTTGG | GCATCGCTAT | GGAACTGTTT | CTGCTGTGCA | GTAACGATGC | GGAGTCAGAT | 480 |
| GTCAGAATGG | TGGCTGATGA | GTGCCTCAAC | AAAGTCATCA | AGCTTGTT | GGATTCTAAT | 540 |
| CTTCCAAGGC | TACAGTTAGA | ACTCTATAAG | GAAATTAAAA | AGAATGGCGC | TCCTCGAAGT | 600 |
| TTGCGTGCTG | CCCTGTGGAG | GTTTGCTGAG | CTGGCTCACC | TGGTTCGACC | TCAGAAGTGC | 660 |
| AGGCCTTACC | TGGTGAATCT | TCTTCCATGC | CTGACCCGAA | CAAGCAAAAG | ACCGGAGGAA | 720 |
| TCAGTTCAGG | AGACCTTGGC | TGCAGCTGTT | CCTAAAATTA | TGGCTTCTTT | TGGCAATTTC | 780 |
| GCAAATGACA | ATGAAATTAA | GGTTCTGTTG | AAAGCTTTCA | TAGCAAATCT | GAAGTCAAGC | 840 |
| TCTCCCACCG | TGCGGCGGAC | AGCAGCCGGC | TCAGCCGTGA | GCATCTGCCA | ACATTCTAGG | 900 |

```
AGGACACAGT ACTTCTACAA CTGGCTCCTT AATGTCCTCC TAGGTCTGCT GGTTCCCATG    960
GAAGAAGAGC ACTCCACTCT CCTGATCCTC GGTGTGTTGC TCACATTGAG GTGTCTAGTG   1020
CCCTTGCTCC AGCAGCAGGT CAAGGACACA AGTCTAAAAG GCAGCTTTGG GGTGACACGG   1080
AAAGAAATGG AAGTCTCTCC TTCTACAGAG CAGCTTGTCC AGGTTTATGA ACTGACTTTG   1140
CATCATACTC AGCACCAAGA CCACAATGTG GTGACAGGGG CACTGGAGCT CCTGCAGCAG   1200
CTCTTCCGTA CCCCTCCACC TGAACTCCTG CAAGCACTGA CCACACCAGG AGGGCTTGGG   1260
CAGCTCACTC TGGTTCAAGA AGAGGCCCGG GGCCGAGGCC GCAGCGGGAG CATCGTGGAG   1320
CTTTTAGCTG GAGGGGGTTC CTCGTGCAGC CCTGTCCTCT CAAGAAAGCA GAAAGGCAAA   1380
GTGCTCTTAG GAGAGGAAGA AGCCTTGGAA GATGACTCGG AGTCCAGGTC AGATGTCAGC   1440
AGCTCAGCCT TTGCAGCCTC TGTGAAGAGT GAGATTGGTG GAGAGCTCGC TGCTTCTTCA   1500
GGTGTTTCCA CTCCTGGTTC TGTTGGTCAC GACATCATCA CTGAGCAGCC TAGATCCCAG   1560
CACACACTTC AAGCAGACTC TGTGGATTTG TCCGGCTGTG ACCTGACCAG TGCTGCTACT   1620
GATGGGGATG AGGAGGACAT CTTGAGCCAC AGCTCCAGCC AGTTCAGTGC TGTCCCACCC   1680
GACCCTCCCA TGGACCTGAA TGATGGGACC CAGCCCTCCT CACCCATCAG TGACAGTTCT   1740
CAGACCACCA CTGAAGGACC TGATTCAGCT GTGACTCCTT CGGACAGTTC TGAAATTGTG   1800
TTAGATGGTG CCGATAGCCA GTATTTAGGC ATGCAGATAG GACAGCCACA GGAGGACGAT   1860
GAGGAGGGAG CTGCAGGTGT TCTTTCTGGT GAAGTCTCAG ATGTTTTCAG AAACTCTTCT   1920
CTGGCCCTTC AACAGACACA CTTGTTGGAA AGAATGGGCC ATAGCAGGCA GCCTTCCGAC   1980
AGCAGTATAG ATAAGTATGT AACAAGAGAT GAGGTTGCTG AAGCCAGTGA TCCAGAAAGC   2040
AAGCCTTGCC GAATCAAAGG TGACATAGGA CAGCCTAATG ATGATGATTC TGCTCCTCTG   2100
GTACATTGTG TCCGTCTTTT ATCTGCTTCC TTTTTGTTAA CTGGTGAAAA GAAAGCACTG   2160
GTTCCAGACA GAGACGTGAG AGTCAGTGTG AAGGCCCTGG CCCTCAGCTG CATTGGTGCG   2220
GCTGTGGCCC TTCATCCAGA GTCGTTCTTC AGCAGACTGT ACAAAGTACC TCTTAATACC   2280
ACGGAAAGTA CTGAGGAACA GTATGTTTCT GACATCTTGA ACTACATCGA TCATGGAGAC   2340
CCACAGGTCC GAGGAGCTAC TGCCATTCTC TGTGGGACCC TTGTCTACTC CATCCTCAGT   2400
AGGTCCCGTC TCCGTGTTGG TGACTGGCTG GGCAACATCA GAACCCTGAC AGGAAATACA   2460
TTTTCTCTGG TGGACTGCAT TCCTTTACTG CAGAAAACGT TGAAGGATGA ATCTTCTGTT   2520
ACTTGCAAGT TGGCTTGTAC AGCTGTGAGG CACTGTGTCC TGAGTCTTTG CAGCAGCAGC   2580
TACAGTGACT TGGGATTACA ACTGCTTATT GATATGCTGC CTCTGAAGAA CAGCTCCTAC   2640
TGGCTGGTGA GGACCGAACT GCTGGACACT CTGGCAGAGA TTGACTTCAG GCTCGTGAGT   2700
TTTTTGGAGG CAAAAGCAGA AAGTTTACAC CGAGGGCTC ATCATTATAC AGGGTTTCTA   2760
AAACTACAAG AACGAGTACT CAATAATGTG GTCATTTATT TGCTTGGAGA TGAAGACCCC   2820
AGGGTTCGAC ATGTTGCTGC AACATCATTA ACAAGGCTTG TCCCAAAGCT GTTTTACAAG   2880
TGTGACCAAG GACAAGCTGA TCCAGTTGTG GCTGTAGCGA GGGATCAGAG CAGTGTCTAC   2940
CTGAAGCTCC TCATGCATGA GACCCAGCCA CCATCACACT TTTCTGTCAG CACCATCACC   3000
AGAATCTATA GAGGCTATAG CTTACTGCCA AGAATAACAG ATGTCACCAT GGAAAACAAT   3060
CTCTCAAGAG TTGTTGCCGC AGTTTCTCAT GAACTCATTA CGCAACAACA CGGGCACTCA   3120
CATTTGGATG CTGTGAAGCC TTGTGTCTTC TCTCAGCAGC CTTTCCAGTT TGCACTTGGA   3180
GTTTAGGATG GCACTGTGGA GTGCCCCAC TGAGTGCCTC TGATGAGTCC AGGAAGAGCT   3240
GCACTGTTGG GATGGCCTCC ATGATTCTCA CCTTGCTTTC ATCAGCTTGG TTCCCACTGG   3300
```

```
ATCTCTCAGC  CCATCAGGAT  GCCTTGATTT  TGGCTGGAAA  CTTGCTAGCA  GCGAGTGCCC    3360
CCAAGTCTCT  GAGAAGTTCA  TGGACCTCTG  AAGAAGAAGC  CAACTCAGCA  GCCACCAGAC    3420
AGGAGGAAAT  CTGCCCTGCT  CTGGGGGATC  GGACTCTAGT  GCCCTTGGTG  GAGCAGCTTT    3480
TCTCCCACCT  GCTGAAGGTG  ATCAATATCT  GTGCTCATGT  CTTGGACGAT  GTGACTCCTG    3540
GACCAGCAAT  CAAGGCAGCC  TTGCCTTCTC  TAACAAACCC  CCCTTCTCTA  AGTCCTATTC    3600
GACGGAAAGG  GAAGGAGAAA  GAACCTGGAG  AACAAGCTTC  TACTCCAATG  AGTCCCAAGA    3660
AAGTTGGTGA  GGCCAGTGCA  GCCTCTCGAC  AATCAGACAC  CTCAGGACCT  GTCACAGCAA    3720
GTAAATCATC  CTCACTGGGG  AGTTTCTACC  ATCTCCCTC   CTACCTCAAA  CTGCATGATG    3780
TCCTGAAAGC  CACTCACGCC  AACTATAAGG  TCACCTTAGA  TCTTCAGAAC  AGCAATGAAA    3840
AGTTTGGGGG  GTTCCTGCGC  TCTGCCTTGG  ACGTCCTTTC  TCAGATTCTA  GAGCTGGCGA    3900
CACTGCAGGA  CATTGGAAAG  TGTGTTGAAG  AGGTCCTTGG  ATACCTGAAA  TCCTGCTTTA    3960
GTCGAGAACC  AATGATGGCA  ACTGTCTGTG  TGCAGCAGCT  ATTGAAGACT  CTCTTTGGGA    4020
CGAACTTAGC  CTCACAGTTT  GATGGCTTAT  CTTCCAACCC  CAGCAAGTCT  CAGTGCCGAG    4080
CTCAGCGCCT  TGGCTCTTCA  AGTGTGAGGC  CCGGCTTATA  TCACTACTGC  TTCATGGCAC    4140
CATACACGCA  CTTCACACAG  GCCTTGGCTG  ACGCAAGCCT  GAGGAACATG  GTGCAGGCGG    4200
AGCAGGAGCG  TGATGCCTCG  GGGTGGTTTG  ATGTACTCCA  GAAAGTGTCT  GCCCAATTGA    4260
AGACGACCCT  AACAAGCGTC  ACAAAGAACC  GTGCAGATAA  GAATGCTATT  CATAATCACA    4320
TTAGGTTATT  TGAGCCTCTT  GTTATAAAAG  CATTGAAGCA  GTACACCACG  ACAACATCTG    4380
TACAATTGCA  GAAGCAGGTT  TTGGATTTGC  TGGCACAGCT  GGTTCAGCTA  CGGGTCAATT    4440
ACTGTCTACT  GGATTCAGAC  CAGGTGTTCA  TCGGGTTTGT  GCTGAAGCAG  TTTGAGTACA    4500
TTGAAGTGGG  CCAGTTCAGG  GAATCAGAGG  CAATTATTCC  AAATATATTT  TTCTTCCTGG    4560
TATTACTGTC  TTATGAGCGC  TACCATTCAA  AACAGATCAT  TGGAATTCCT  AAAATCATCC    4620
AGCTGTGTGA  TGGCATCATG  GCCAGTGGAA  GGAAGGCCGT  TACACATGCT  ATACCTGCTC    4680
TGCAGCCCAT  TGTCCATGAC  CTCTTTGTGT  TACGAGGAAC  AAATAAAGCT  GATGCAGGGA    4740
AAGAGCTTGA  GACACAGAAG  GAGGTGGTGG  TCTCCATGCT  GTTACGACTC  ATCCAGTACC    4800
ACAGGTGCTG  GAGATGTTCA  TCCTTGTCCT  GCAGCAGTGC  CACAAGGAGA  ATGAGGACAA    4860
GTGGAAACGG  CTCTCTCGGC  AGGTCGCAGA  CATCATCCTG  CCCATGTTGG  CCAAGCAGCA    4920
GATGCATATT  GACTCTCATG  AAGCCCTTGG  AGTGTTAAAT  ACCTTGTTTG  AGATTTTGGC    4980
TCCTTCCTCC  CTACGTCCCG  TGGACATGCT  TTTGCGGAGT  ATGTTCATCA  CTCCAAGCAC    5040
AATGGCATCT  GTAAGCACTG  TGCAGCTGTG  GATATCTGGA  ATCCTCGCCA  TTCTGAGGGT    5100
TCTCATTTCC  CAGTCAACCG  AGGACATTGT  TCTTTGTCGT  ATTCAGGAGC  TCTCCTTCTC    5160
TCCACACTTG  CTCTCCTGTC  CAGTGATTAA  CAGGTTAAGG  GGTGGAGGCG  GTAATGTAAC    5220
ACTAGGAGAA  TGCAGCGAAG  GGAAACAAAA  GAGTTTGCCA  GAAGATACAT  TCTCAAGGTT    5280
TCTTTTACAG  CTGGTTGGTA  TTCTTCTAGA  AGACATCGTT  ACAAAACAGC  TCAAAGTGGA    5340
CATGAGTGAA  CAGCAGCATA  CGTTCTACTG  CCAAGAGCTA  GGCACACTGC  TCATGTGTCT    5400
GATCCACATA  TTCAAATCTG  GAATGTTCCG  GAGAATCACA  GCAGCTGCCA  CTAGACTCTT    5460
CACCAGTGAT  GGCTGTGAAG  GCAGCTTCTA  TACTCTAGAG  AGCCTGAATG  CACGGGTCCG    5520
ATCCATGGTG  CCCACGCACC  CAGCCCTGGT  ACTGCTCTGG  TGTCAGATCC  TACTTCTCAT    5580
CAACCACACT  GACTACCGGT  GGTGGGCAGA  GGTGCAGCAG  ACACCCAAGA  GACACAGTCT    5640
GTCCTGCACG  AAGTCACTTA  ACCCCCAGAA  GTCTGGCGAA  GAGGAGGATT  CTGGCTCGGC    5700
```

```
AGCTCAGCTG  GGAATGTGCA  ATAGAGAAAT  AGTGCGGAGA  GGGGCCCTTA  TTCTCTTCTG    5760
TGATTATGTC  TGTCAGAATC  TCCATGACTC  AGAACACTTA  ACATGGCTCA  TTGTGAATCA    5820
CATTCAAGAT  CTGATCAGCT  TGTCTCATGA  GCCTCCAGTA  CAAGACTTTA  TTAGTGCCAT    5880
TCATCGTAAT  TCTGCAGCTA  GTGGTCTTTT  TATCCAGGCA  ATTCAGTCTC  GCTGTGAAAA    5940
TCTTTCAACG  CCAACCACTC  TGAAGAAAAC  ACTTCAGTGC  TTGGAAGGCA  TCCATCTCAG    6000
CCAGTCTGGC  GCTGTGCTCA  CACTATATGT  GGACAGGCTC  CTGGGCACCT  CCTCCCGTGC    6060
GCTGGCTCGC  ATGGTCGACA  CCCTGGCCTG  TCGCCGGGTA  GAAATGCTTT  TGGCTGCAAA    6120
TTTACAGAGC  AGCATGGCCC  AGTTGCCAGA  GGAGGAACTA  AACAGAATCC  AAGAACACCT    6180
CCAGAACAGT  GGGCTTGCAC  AAAGACACCA  AAGGCTCTAT  TCACTGCTGG  ACAGATTCCG    6240
ACTCTCTACT  GTGCAGGACT  CACTTAGCCC  CTTGCCCCCA  GTCACTTCCC  ACCCACTGGG    6300
TGGGGATGGG  CACACATCTC  TGGAAACAGT  GAGTCCAGAC  AAAGACTGGT  ACCTCCAGCT    6360
TGTCAGATCC  CAGTGTTGGA  CCAGATCAGA  TTCTGCACTG  CTGGAAGGTG  CAGAGCTGGT    6420
CAACCGTATC  CCTGCTGAAG  ATATGAATGA  CTTCATGATG  AGCTCGGAGT  TCAACCTAAG    6480
CCTTTTGGCT  CCCTGTTTAA  GCCTTGGCAT  GAGCGAGATT  GCTAATGGCC  AAAAGAGTCC    6540
CCTCTTTGAA  GCAGCCCGTG  GGGTGATTCT  GAACCGGGTG  ACCAGTGTTG  TTCAGCAGCT    6600
TCCTGCTGTC  CATCAAGTCT  TCCAGCCCTT  CCTGCCTATA  GAGCCCACGG  CCTACTGGAA    6660
CAAGTTGAAT  GATCTGCTTG  GTGATACCAC  ATCATACCAG  TCTCTGACCA  TACTTGCCCG    6720
TGCCCTGGCA  CAGTACCTGG  TGGTGCTCTC  CAAAGTGCCT  GCTCATTTGC  ACCTTCCTCC    6780
TGAGAAGGAG  GGGGACACGG  TGAAGTTTGT  GGTAATGACA  GTTGAGGCCC  TGTCATGGCA    6840
TTTGATCCAT  GAGCAGATCC  CACTGAGTCT  GGACCTCCAA  GCCGGGCTAG  ACTGCTGCTG    6900
CCTGGCACTA  CAGGTGCCTG  GCCTCTGGGG  GGTGCTGTCC  TCCCCAGAGT  ACGTGACTCA    6960
TGCCTGCTCC  CTCATCCATT  GTGTGCGATT  CATCCTGGAA  GCCATTGCAG  TACAACCTGG    7020
AGACCAGCTT  CTCGGTCCTG  AAAGCAGGTC  ACATACTCCA  AGAGCTGTCA  GAAAGGAGGA    7080
AGTAGACTCA  GATATACAAA  ACCTCAGTCA  TGTCACTTCG  GCCTGCGAGA  TGGTGGCAGA    7140
CATGGTGGAA  TCCCTGCAGT  CAGTGCTGGC  CTTGGGCCAC  AAGAGGAACA  GCACCCTGCC    7200
TTCATTTCTC  ACAGCTGTGC  TGAAGAACAT  TGTTATCAGT  CTGGCCCGAC  TCCCCCTAGT    7260
TAACAGCTAT  ACTCGTGTGC  CTCCTCTGGT  ATGGAAACTC  GGGTGGTCAC  CCAAGCCTGG    7320
AGGGGATTTT  GGGACAGTGT  TTCCTGAGAT  CCCTGTAGAG  TTCCTCCAGG  AGAAGGAGAT    7380
CCTCAAGGAG  TTCATCTACC  GCATCAACAC  CCTAGGGTGG  ACCAATCGTA  CCCAGTTCGA    7440
AGAAACTTGG  GCCACCCTCC  TTGGTGTCCT  GGTGACTCAG  CCCCTGGTGA  TGGAACAGGA    7500
AGAGAGCCCA  CCAGAGGAAG  ACACAGAAAG  AACCCAGATC  CATGTCCTGG  CTGTGCAGGC    7560
CATCACCTCT  CTAGTGCTCA  GTGCAATGAC  CGTGCCTGTG  GCTGGCAATC  CAGCTGTAAG    7620
CTGCTTGGAG  CAACAGCCCC  GGAACAAGCC  ACTGAAGGCT  CTCGATACCA  GATTTGGAAG    7680
AAAGCTGAGC  ATGATCAGAG  GGATTGTAGA  ACAAGAAATC  CAAGAGATGG  TTTCCCAGAG    7740
AGAGAATACT  GCCACTCACC  ATTCTCACCA  GGCGTGGGAT  CCTGTCCCTT  CTCTGTTACC    7800
AGCTACTACA  GGTGCTCTTA  TCAACCATGA  CAAGCTGCTG  CTGCAGATCA  ACCCAGAGCG    7860
GGAGCCAGGC  AACATGAGCT  ACAAGCTGGG  CCAGGTGTCC  ATACACTCCG  TGTGGCTGGG    7920
AAATAACATC  ACACCCCTGA  GAGAGGAGGA  ATGGGATGAG  GAAGAAGAGG  AAGAAAGTGA    7980
TGTCCCTGCA  CCAACGTCAC  CACCTGTGTC  TCCAGTCAAT  TCCAGAAAAC  ACCGTGCCGG    8040
GGTTGATATT  CACTCCTGTT  CGCAGTTTCT  GCTTGAATTG  TACAGCCGAT  GGATCCTGCC    8100
```

```
ATCCAGTGCA  GCCAGAAGGA  CCCCCGTCAT  CCTGATCAGT  GAAGTGGTTC  GATCTCTTCT     8160
TGTAGTGTCA  GACTTATTCA  CCGAACGTAC  CCAGTTTGAA  ATGATGTATC  TGACGCTGAC     8220
AGAACTACGG  AGAGTGCACC  CTTCAGAAGA  TGAGATCCTC  ATTCAGTACC  TGGTGCCTGC     8280
CACCTGTAAG  GCAGCTGCTG  TCCTTGGAAT  GGACAAAACT  GTGGCAGAGC  CAGTCAGCCG     8340
CCTACTGGAG  AGCACACTGA  GGAGCAGCCA  CCTGCCCAGC  CAGATCGGAG  CCCTGCACGG     8400
CATCCTCTAT  GTGTTGGAGT  GTGACCTCTT  GGATGACACT  GCAAAGCAGC  TCATTCCAGT     8460
TGTTAGTGAC  TATCTGCTGT  CCAACCTCAA  AGGAATAGCC  CACTGCGTGA  ACATTCACAG     8520
CCAGCAGCAT  GTGCTGGTAA  TGTGTGCCAC  TGCTTTCTAC  CTGATGGAAA  ACTACCCTCT     8580
GGATGTGGGA  CCAGAATTTT  CAGCATCTGT  GATACAGATG  TGTGGAGTAA  TGCTGTCTGG     8640
AAGTGAGGAG  TCCACCCCCT  CCATCATTTA  CCACTGTGCC  CTCCGGGGTC  TGGAGCGGCT     8700
CCTGCTGTCT  GTGCAGCTAT  CTCGTCTAGA  CACAGAGTCC  CTGGGCAAGC  TAAGTGTGGG     8760
CAGAGTGAAT  GTACACAGCC  CACACAGGGC  CATGGCAGCC  CTAGGCCTGA  TGCTCACCTG     8820
CATGTACACA  GGAAAGGAGA  AAGCCAGTCC  AGGCAGAACT  TCTGACCCCA  GCCCTGCTAC     8880
ACCTGACAGC  GAGTCTGTGA  TTGTAGCTAT  GGAGCGAGTG  TCTGTTCTCT  TTGATAGGAT     8940
CCGCAAGGGA  TTTCCCTGTG  AAGCCAGGGT  TGTGGCAAGG  ATCCTGCCTC  AGTTCCTAGA     9000
TGACTTCTTT  CCACCTCAAG  ATGTCATGAA  CAAAGTCATT  GGAGAGTTCC  TGTCCAATCA     9060
GCAGCCATAC  CCACAGTTCA  TGGCCACTGT  AGTTTACAAG  GTTTTTCAGA  CTCTGCACAG     9120
TGCTGGGCAG  TCATCCATGG  TCCGGGACTG  GGTCATGCTG  TCCCTGTCCA  ACTTCACACA     9180
AAGAACTCCA  GTTGCCATGG  CCATGTGGAG  CCTCTCCTGC  TTCCTTGTTA  GCGCATCTAC     9240
CAGCCCATGG  GTTTCTGCGA  TCCTTCCACA  TGTCATCAGC  AGGATGGGCA  AGCTGGAACT     9300
AATGGATGTG  AACCTTTTCT  GCCTGGTTGC  CACAGACTTC  TACAGACACC  AGATAGAGGA     9360
GGAATTCGAC  CGCAGGGCTT  TCCAGTCTGT  GTTTGAGGAG  GAGGCGGCAC  CAGGAAGTCC     9420
ATACCACAGG  CTGCTTGCTT  GTTTGCAAAA  TGTTCACAAG  GTCACCACCT  GCTGAGACCG     9480
CAGGGCTTTC  CAGTCTGTGT  TTGAGGAGGA  GGCGGCACCA  GGAAGTCCAT  ACCACAGGCT     9540
GCTTGCTTGT  TTGCAAAATG  TTCACAAGGT  CACCACCTGC  TGAGTAGTGC  CTGTGGGACA     9600
AAAGGCTGAA  AGAAGGCAGC  TGCTGGGGCC  TGAGCTCCAG  GAGCCTGCTC  AAGCTTCTGC     9660
TGGGGCTGCC  TTGGCCGTGC  AGGCTTCCAC  TTGTGTCAAG  TGGACAGCCA  GGCAATGGCA     9720
GGAGTGCTTT  GCAATGAGGG  CTATGCAGGG  AACATGCACT  ATGTTGGGGT  TGAGCCTAGT     9780
GCTAGGTTGA  CCAGGTGTTT  GTCTTTTTCC  TAGTGTTCCC  CTGGCCATAG  TCGCCAGGTT     9840
GCAGCTGCCC  TGGTATGTGG  ATCAGAAGTC  CTAGCTCTTG  CCAGATGGTT  CTGAGCCCGC     9900
CTGCTCCACT  GGGCTGGAGA  GCTCCCTCCC  ACATTTACCC  AGTAGGCATA  CCTGCCACAC     9960
CAGTGTCTGG  ACACAAAATG  AATGGTGTGT  GGGGGCTGGG  AACTGGGGCT  GCCAGGTGTC    10020
CAGCACCATT  TTCCTTTCTG  TGTTTTCTTC  TCAGGAGTTA  AAATTTAATT  ATATCAGTAA    10080
AGAGATTAAT  TTTAATGTAA  AAA                                               10103
```

( 2 ) INFORMATION FOR SEQ ID NO:8:

( i ) SEQUENCE CHARACTERISTICS:
        ( A ) LENGTH: 3118 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met Gly Thr Leu Glu Lys Leu Met Lys Ala Phe Glu Ser Leu Lys Ser
 1               5                  10                  15

Phe Gln Gln Gln Gln Gln Gln Pro Pro Pro Gln Ala Pro Pro Pro Pro
              20                  25                  30

Pro Pro Pro Pro Pro Pro Gln Pro Gln Pro Pro Gln Gly Gln
              35                  40                  45

Pro Pro Pro Pro Pro Pro Leu Pro Gly Pro Ala Glu Glu Pro Leu
     50                  55                  60

His Arg Pro Lys Lys Glu Leu Ser Ala Thr Lys Lys Asp Arg Val Asn
 65                  70                  75                  80

His Cys Leu Thr Ile Cys Glu Asn Ile Val Ala Gln Ser Leu Arg Asn
                  85                  90                  95

Ser Pro Glu Phe Gln Lys Leu Leu Gly Ile Ala Met Glu Leu Phe Leu
                 100                 105                 110

Leu Cys Ser Asn Asp Ala Glu Ser Asp Val Arg Met Val Ala Asp Glu
             115                 120                 125

Cys Leu Asn Lys Val Ile Lys Ala Leu Leu Asp Ser Asn Leu Pro Arg
    130                 135                 140

Leu Gln Leu Glu Leu Tyr Lys Glu Ile Lys Lys Asn Gly Ala Pro Arg
145                 150                 155                 160

Ser Leu Arg Ala Ala Leu Trp Arg Phe Ala Glu Leu Ala His Leu Val
                 165                 170                 175

Arg Pro Gln Lys Cys Arg Pro Tyr Leu Val Asn Leu Leu Pro Cys Leu
             180                 185                 190

Thr Arg Thr Ser Lys Arg Pro Glu Glu Ser Val Gln Glu Thr Leu Ala
            195                 200                 205

Ala Ala Val Pro Lys Ile Met Ala Ser Phe Gly Asn Phe Ala Asn Asp
    210                 215                 220

Asn Glu Ile Lys Val Leu Leu Lys Ala Phe Ile Ala Asn Leu Lys Ser
225                 230                 235                 240

Ser Ser Pro Thr Val Arg Arg Thr Ala Ala Gly Ser Ala Val Ser Ile
                 245                 250                 255

Cys Gln His Ser Arg Arg Thr Gln Tyr Phe Tyr Asn Trp Leu Leu Asn
             260                 265                 270

Val Leu Leu Gly Leu Leu Val Pro Met Glu Glu Glu His Ser Thr Leu
        275                 280                 285

Leu Ile Leu Gly Val Leu Leu Thr Leu Arg Cys Leu Val Pro Leu Leu
    290                 295                 300

Gln Gln Gln Val Lys Asp Thr Ser Leu Lys Gly Ser Phe Gly Val Thr
305                 310                 315                 320

Arg Lys Glu Met Glu Val Ser Pro Ser Thr Glu Gln Leu Val Gln Val
                325                 330                 335

Tyr Glu Leu Thr Leu His His Thr Gln His Gln Asp His Asn Val Val
            340                 345                 350

Thr Gly Ala Leu Glu Leu Leu Gln Gln Leu Phe Arg Thr Pro Pro Pro
        355                 360                 365

Glu Leu Leu Gln Ala Leu Thr Thr Pro Gly Gly Leu Gly Gln Leu Thr
    370                 375                 380

Leu Val Gln Glu Glu Ala Arg Gly Arg Gly Arg Ser Gly Ser Ile Val
385                 390                 395                 400

Glu Leu Leu Ala Gly Gly Gly Ser Ser Cys Ser Pro Val Leu Ser Arg
                405                 410                 415
```

```
Lys  Gln  Lys  Gly  Lys  Val  Leu  Leu  Gly  Glu  Glu  Ala  Leu  Glu  Asp
          420                     425                     430

Asp  Ser  Glu  Ser  Arg  Ser  Asp  Val  Ser  Ser  Ser  Ala  Phe  Ala  Ala  Ser
          435                     440                     445

Val  Lys  Ser  Glu  Ile  Gly  Gly  Glu  Leu  Ala  Ala  Ser  Gly  Val  Ser
     450                     455                     460

Thr  Pro  Gly  Ser  Val  Gly  His  Asp  Ile  Ile  Thr  Glu  Pro  Arg  Ser  Gln
465                      470                     475                     480

His  Thr  Leu  Gln  Ala  Asp  Ser  Val  Asp  Leu  Ser  Gly  Cys  Asp  Leu  Thr
               485                     490                          495

Ser  Ala  Ala  Thr  Asp  Gly  Asp  Glu  Glu  Asp  Ile  Leu  Ser  His  Ser  Ser
               500                     505                     510

Ser  Gln  Phe  Ser  Ala  Val  Pro  Pro  Asp  Pro  Met  Asp  Leu  Asn  Asp
          515                     520                     525

Gly  Thr  Gln  Pro  Ser  Ser  Pro  Ile  Ser  Asp  Ser  Ser  Gln  Thr  Thr  Thr
     530                     535                     540

Glu  Gly  Pro  Asp  Ser  Ala  Val  Thr  Pro  Ser  Asp  Ser  Ser  Glu  Ile  Val
545                      550                     555                     560

Leu  Asp  Gly  Ala  Asp  Ser  Gln  Tyr  Leu  Gly  Met  Gln  Ile  Gly  Gln  Pro
               565                     570                     575

Gln  Glu  Asp  Asp  Glu  Glu  Gly  Ala  Ala  Gly  Val  Leu  Ser  Gly  Glu  Val
               580                     585                     590

Ser  Asp  Val  Phe  Arg  Asn  Ser  Ser  Leu  Ala  Leu  Gln  Gln  Thr  His  Leu
          595                     600                     605

Leu  Glu  Arg  Met  Gly  His  Ser  Arg  Gln  Pro  Ser  Asp  Ser  Ser  Ile  Asp
     610                     615                     620

Lys  Tyr  Val  Thr  Arg  Asp  Glu  Val  Ala  Glu  Ala  Ser  Asp  Pro  Glu  Ser
625                      630                     635                          640

Lys  Pro  Cys  Arg  Ile  Lys  Gly  Asp  Ile  Gly  Gln  Pro  Asn  Asp  Asp  Asp
                    645                     650                          655

Ser  Ala  Pro  Leu  Val  His  Cys  Val  Arg  Leu  Leu  Ser  Ala  Ser  Phe  Leu
               660                     665                     670

Leu  Thr  Gly  Glu  Lys  Lys  Ala  Leu  Val  Pro  Asp  Arg  Asp  Val  Arg  Val
          675                     680                     685

Ser  Val  Lys  Ala  Leu  Ala  Leu  Ser  Cys  Ile  Gly  Ala  Ala  Val  Ala  Leu
     690                     695                     700

His  Pro  Glu  Ser  Phe  Phe  Ser  Arg  Leu  Tyr  Lys  Val  Pro  Leu  Asn  Thr
705                      710                     715                          720

Thr  Glu  Ser  Thr  Glu  Glu  Gln  Tyr  Val  Ser  Asp  Ile  Leu  Asn  Tyr  Ile
                    725                     730                     735

Asp  His  Gly  Asp  Pro  Gln  Val  Arg  Gly  Ala  Thr  Ala  Ile  Leu  Cys  Gly
               740                     745                     750

Thr  Leu  Val  Tyr  Ser  Ile  Leu  Ser  Arg  Ser  Arg  Leu  Arg  Val  Gly  Asp
          755                     760                     765

Trp  Leu  Gly  Asn  Ile  Arg  Thr  Leu  Thr  Gly  Asn  Thr  Phe  Ser  Leu  Val
     770                     775                     780

Asp  Cys  Ile  Pro  Leu  Leu  Gln  Lys  Thr  Leu  Lys  Asp  Glu  Ser  Ser  Val
785                      790                     795                          800

Thr  Cys  Lys  Leu  Ala  Cys  Thr  Ala  Val  Arg  His  Cys  Val  Leu  Ser  Leu
                    805                     810                     815

Cys  Ser  Ser  Ser  Tyr  Ser  Asp  Leu  Gly  Leu  Gln  Leu  Leu  Ile  Asp  Met
               820                     825                     830

Leu  Pro  Leu  Lys  Asn  Ser  Ser  Tyr  Trp  Leu  Val  Arg  Thr  Glu  Leu  Leu
          835                     840                     845
```

```
Asp  Thr  Leu  Ala  Glu  Ile  Asp  Phe  Arg  Leu  Val  Ser  Phe  Leu  Glu  Ala
     850                 855                      860

Lys  Ala  Glu  Ser  Leu  His  Arg  Gly  Ala  His  His  Tyr  Thr  Gly  Phe  Leu
865                      870                 875                           880

Lys  Leu  Gln  Glu  Arg  Val  Leu  Asn  Asn  Val  Ile  Tyr  Leu  Leu  Gly
                    885                 890                           895

Asp  Glu  Asp  Pro  Arg  Val  Arg  His  Val  Ala  Ala  Thr  Ser  Leu  Thr  Arg
               900                      905                      910

Leu  Val  Pro  Lys  Leu  Phe  Tyr  Lys  Cys  Asp  Gln  Gly  Gln  Ala  Asp  Pro
               915                 920                      925

Val  Val  Ala  Val  Ala  Arg  Asp  Gln  Ser  Ser  Val  Tyr  Leu  Lys  Leu  Leu
930                      935                           940

Met  His  Glu  Thr  Gln  Pro  Ser  His  Phe  Ser  Val  Ser  Thr  Ile  Thr
945                      950                 955                           960

Arg  Ile  Tyr  Arg  Gly  Tyr  Ser  Leu  Leu  Pro  Arg  Ile  Thr  Asp  Val  Thr
                    965                      970                      975

Met  Glu  Asn  Asn  Leu  Ser  Arg  Val  Val  Ala  Ala  Val  Ser  His  Glu  Leu
               980                      985                           990

Ile  Thr  Ser  Thr  Thr  Arg  Ala  Leu  Thr  Phe  Gly  Cys  Cys  Glu  Ala  Leu
          995                      1000                      1005

Cys  Leu  Leu  Ser  Ala  Ala  Phe  Pro  Val  Cys  Thr  Trp  Ser  Leu  Gly  Trp
          1010                     1015                     1020

His  Cys  Gly  Val  Pro  Pro  Leu  Ser  Ala  Ser  Asp  Glu  Ser  Arg  Lys  Ser
1025                     1030                     1035                     1040

Cys  Thr  Val  Gly  Met  Ala  Ser  Met  Ile  Leu  Thr  Leu  Leu  Ser  Ser  Ala
                    1045                     1050                     1055

Trp  Phe  Pro  Leu  Asp  Leu  Ser  Ala  His  Gln  Asp  Ala  Leu  Ile  Leu  Ala
               1060                     1065                     1070

Gly  Asn  Leu  Leu  Ala  Ala  Ser  Ala  Pro  Lys  Ser  Leu  Arg  Ser  Ser  Trp
               1075                     1080                     1085

Thr  Ser  Glu  Glu  Glu  Ala  Asn  Ser  Ala  Ala  Thr  Arg  Gln  Glu  Glu  Ile
     1090                     1095                     1100

Gly  Pro  Ala  Leu  Cys  Asp  Arg  Thr  Leu  Val  Pro  Leu  Val  Glu  Gln  Leu
1105                     1110                     1115                     1120

Phe  Ser  His  Leu  Leu  Lys  Val  Ile  Asn  Ile  Cys  Ala  His  Val  Leu  Asp
                    1125                     1130                     1135

Asp  Val  Thr  Pro  Gly  Pro  Ala  Ile  Lys  Ala  Ala  Leu  Pro  Ser  Leu  Thr
               1140                     1145                     1150

Asn  Pro  Pro  Ser  Leu  Ser  Pro  Ile  Arg  Arg  Lys  Gly  Lys  Glu  Lys  Glu
               1155                     1160                     1165

Pro  Gly  Glu  Gln  Ala  Ser  Thr  Pro  Met  Ser  Pro  Lys  Lys  Val  Gly  Glu
     1170                     1175                     1180

Ala  Ser  Ala  Ala  Ser  Arg  Gln  Ser  Asp  Thr  Ser  Gly  Pro  Val  Thr  Ala
1185                     1190                     1195                     1200

Ser  Lys  Ser  Ser  Ser  Leu  Gly  Ser  Phe  Tyr  His  Leu  Pro  Ser  Tyr  Leu
                    1205                     1210                     1215

Lys  Leu  His  Asp  Val  Leu  Lys  Ala  Thr  His  Ala  Asn  Tyr  Lys  Val  Thr
               1220                     1225                     1230

Leu  Asp  Leu  Gln  Asn  Ser  Asn  Glu  Lys  Phe  Gly  Gly  Phe  Leu  Arg  Ser
          1235                     1240                     1245

Ala  Leu  Asp  Val  Leu  Ser  Gln  Ile  Leu  Glu  Leu  Ala  Thr  Leu  Gln  Asp
     1250                     1255                     1260

Ile  Gly  Lys  Cys  Val  Glu  Glu  Val  Leu  Gly  Tyr  Leu  Lys  Ser  Cys  Phe
```

```
               1265                    1270                     1275                     1280

Ser  Arg  Glu  Pro  Met  Met  Ala  Thr  Val  Cys  Val  Gln  Gln  Leu  Leu  Lys
                              1285                     1290                     1295

Thr  Leu  Phe  Gly  Thr  Asn  Leu  Ala  Ser  Gln  Phe  Asp  Gly  Leu  Ser  Ser
                         1300                    1305                     1310

Asn  Pro  Ser  Lys  Ser  Gln  Cys  Arg  Ala  Gln  Arg  Leu  Gly  Ser  Ser  Ser
                         1315                    1320                     1325

Val  Arg  Pro  Gly  Leu  Tyr  His  Tyr  Cys  Phe  Met  Ala  Pro  Tyr  Thr  His
                         1330                    1335                     1340

Phe  Thr  Gln  Ala  Leu  Ala  Asp  Ala  Ser  Leu  Arg  Asn  Met  Val  Gln  Ala
          1345                     1350                    1355                     1360

Glu  Gln  Glu  Arg  Asp  Ala  Ser  Gly  Trp  Phe  Asp  Val  Leu  Gln  Lys  Val
                              1365                    1370                     1375

Ser  Ala  Gln  Leu  Lys  Thr  Thr  Leu  Thr  Ser  Val  Thr  Lys  Asn  Arg  Ala
                         1380                    1385                     1390

Asp  Lys  Asn  Ala  Ile  His  Asn  His  Ile  Arg  Leu  Phe  Glu  Pro  Leu  Val
                         1395                    1400                     1405

Ile  Lys  Ala  Leu  Lys  Gln  Tyr  Thr  Thr  Thr  Thr  Ser  Val  Gln  Leu  Gln
                         1410                    1415                     1420

Lys  Gln  Val  Leu  Asp  Leu  Leu  Ala  Gln  Leu  Val  Gln  Leu  Arg  Val  Asn
          1425                     1430                    1435                     1440

Tyr  Cys  Leu  Leu  Asp  Ser  Asp  Gln  Val  Phe  Ile  Gly  Phe  Val  Leu  Lys
                              1445                    1450                     1455

Gln  Phe  Glu  Tyr  Ile  Glu  Val  Gly  Gln  Phe  Arg  Glu  Ser  Glu  Ala  Ile
                         1460                    1465                     1470

Ile  Pro  Asn  Ile  Phe  Phe  Phe  Leu  Val  Leu  Leu  Ser  Tyr  Glu  Arg  Tyr
                         1475                    1480                     1485

His  Ser  Lys  Gln  Ile  Ile  Gly  Ile  Pro  Lys  Ile  Ile  Gln  Leu  Cys  Asp
                         1490                    1495                     1500

Gly  Ile  Met  Ala  Ser  Gly  Arg  Lys  Ala  Val  Thr  His  Ala  Ile  Pro  Ala
          1505                     1510                    1515                     1520

Leu  Gln  Pro  Ile  Val  His  Asp  Leu  Phe  Val  Leu  Arg  Gly  Thr  Asn  Lys
                              1525                    1530                     1535

Ala  Asp  Ala  Gly  Lys  Glu  Leu  Glu  Thr  Gln  Lys  Glu  Val  Val  Val  Ser
                              1540                    1545                     1550

Met  Leu  Leu  Arg  Leu  Ile  Gln  Tyr  His  Gln  Val  Leu  Glu  Met  Phe  Ile
                         1555                    1560                     1565

Leu  Val  Leu  Gln  Gln  Cys  His  Lys  Glu  Asn  Glu  Asp  Lys  Trp  Lys  Arg
                         1570                    1575                     1580

Leu  Ser  Arg  Gln  Val  Ala  Asp  Ile  Ile  Leu  Pro  Met  Leu  Ala  Lys  Gln
          1585                     1590                    1595                     1600

Gln  Met  His  Ile  Asp  Ser  His  Glu  Ala  Leu  Gly  Val  Leu  Asn  Thr  Leu
                              1605                    1610                     1615

Phe  Glu  Ile  Leu  Ala  Pro  Ser  Ser  Leu  Arg  Pro  Val  Asp  Met  Leu  Leu
                         1620                    1625                     1630

Arg  Ser  Met  Phe  Ile  Thr  Pro  Ser  Thr  Met  Ala  Ser  Val  Ser  Thr  Val
                              1635                    1640                     1645

Gln  Leu  Trp  Ile  Ser  Gly  Ile  Leu  Ala  Ile  Leu  Arg  Val  Leu  Ile  Ser
                         1650                    1655                     1660

Gln  Ser  Thr  Glu  Asp  Ile  Val  Leu  Cys  Arg  Ile  Gln  Glu  Leu  Ser  Phe
          1665                     1670                    1675                     1680

Ser  Pro  His  Leu  Leu  Ser  Cys  Pro  Val  Ile  Asn  Arg  Leu  Arg  Gly  Gly
                              1685                    1690                     1695
```

-continued

```
Gly Gly Asn Val Thr Leu Gly Glu Cys Ser Glu Gly Lys Gln Lys Ser
              1700                1705                1710

Leu Pro Glu Asp Thr Phe Ser Arg Phe Leu Leu Gln Leu Val Gly Ile
         1715                1720                1725

Leu Leu Glu Asp Ile Val Thr Lys Gln Leu Lys Val Asp Met Ser Glu
         1730                1735                1740

Gln Gln His Thr Phe Tyr Cys Gln Glu Leu Gly Thr Leu Leu Met Cys
1745                1750                1755                1760

Leu Ile His Ile Phe Lys Ser Gly Met Phe Arg Arg Ile Thr Ala Ala
              1765                1770                1775

Ala Thr Arg Leu Phe Thr Ser Asp Gly Cys Glu Gly Ser Phe Tyr Thr
              1780                1785                1790

Leu Glu Ser Leu Asn Ala Arg Val Arg Ser Met Val Pro Thr His Pro
         1795                1800                1805

Ala Leu Val Leu Leu Trp Cys Gln Ile Leu Leu Leu Ile Asn His Thr
         1810                1815                1820

Asp Tyr Arg Trp Trp Ala Glu Val Gln Gln Thr Pro Lys Arg His Ser
1825                1830                1835                1840

Leu Ser Cys Thr Lys Ser Leu Asn Pro Gln Lys Ser Gly Glu Glu Glu
              1845                1850                1855

Asp Ser Gly Ser Ala Ala Gln Leu Gly Met Cys Asn Arg Glu Ile Val
              1860                1865                1870

Arg Arg Gly Ala Leu Ile Leu Phe Cys Asp Tyr Val Cys Gln Asn Leu
              1875                1880                1885

His Asp Ser Glu His Leu Thr Trp Leu Ile Val Asn His Ile Gln Asp
              1890                1895                1900

Leu Ile Ser Leu Ser His Glu Pro Pro Val Gln Asp Phe Ile Ser Ala
1905                1910                1915                1920

Ile His Arg Asn Ser Ala Ala Ser Gly Leu Phe Ile Gln Ala Ile Gln
                   1925                1930                1935

Ser Arg Cys Glu Asn Leu Ser Thr Pro Thr Thr Leu Lys Lys Thr Leu
              1940                1945                1950

Gln Cys Leu Glu Gly Ile His Leu Ser Gln Ser Gly Ala Val Leu Thr
              1955                1960                1965

Leu Tyr Val Asp Arg Leu Leu Gly Thr Ser Ser Arg Ala Leu Ala Arg
         1970                1975                1980

Met Val Asp Thr Leu Ala Cys Arg Arg Val Glu Met Leu Leu Ala Ala
1985                1990                1995                2000

Asn Leu Gln Ser Ser Met Ala Gln Leu Pro Glu Glu Glu Leu Asn Arg
              2005                2010                2015

Ile Gln Glu His Leu Gln Asn Ser Gly Leu Ala Gln Arg His Gln Arg
              2020                2025                2030

Leu Tyr Ser Leu Leu Asp Arg Phe Arg Leu Ser Thr Val Gln Asp Ser
              2035                2040                2045

Leu Ser Pro Leu Pro Pro Val Thr Ser His Pro Leu Gly Gly Asp Gly
              2050                2055                2060

His Thr Ser Leu Glu Thr Val Ser Pro Asp Lys Asp Trp Tyr Leu Gln
2065                2070                2075                2080

Leu Val Arg Ser Gln Cys Trp Thr Arg Ser Asp Ser Ala Leu Leu Glu
              2085                2090                2095

Gly Ala Glu Leu Val Asn Arg Ile Pro Ala Glu Asp Met Asn Asp Phe
              2100                2105                2110

Met Met Ser Ser Glu Phe Asn Leu Ser Leu Leu Ala Pro Cys Leu Ser
              2115                2120                2125
```

```
Leu Gly Met Ser Glu Ile Ala Asn Gly Gln Lys Ser Pro Leu Phe Glu
        2130                2135                2140
Ala Ala Arg Gly Val Ile Leu Asn Arg Val Thr Ser Val Val Gln Gln
2145                2150                2155                2160
Leu Pro Ala Val His Gln Val Phe Gln Pro Phe Leu Pro Ile Glu Pro
                2165                2170                2175
Thr Ala Tyr Trp Asn Lys Leu Asn Asp Leu Leu Gly Asp Thr Thr Ser
        2180                2185                2190
Tyr Gln Ser Leu Thr Ile Leu Ala Arg Ala Leu Ala Gln Tyr Leu Val
            2195                2200                2205
Val Leu Ser Lys Val Pro Ala His Leu His Leu Pro Pro Glu Lys Glu
        2210                2215                2220
Gly Asp Thr Val Lys Phe Val Val Met Thr Val Glu Ala Leu Ser Trp
2225                2230                2235                2240
His Leu Ile His Glu Gln Ile Pro Leu Ser Leu Asp Leu Gln Ala Gly
                2245                2250                2255
Leu Asp Cys Cys Cys Leu Ala Leu Gln Val Pro Gly Leu Trp Gly Val
                2260                2265                2270
Leu Ser Ser Pro Glu Tyr Val Thr His Ala Cys Ser Leu Ile His Cys
            2275                2280                2285
Val Arg Phe Ile Leu Glu Ala Ile Ala Val Gln Pro Gly Asp Gln Leu
        2290                2295                2300
Leu Gly Pro Glu Ser Arg Ser His Thr Pro Arg Ala Val Arg Lys Glu
2305                2310                2315                2320
Glu Val Asp Ser Asp Ile Gln Asn Leu Ser His Val Thr Ser Ala Cys
                2325                2330                2335
Glu Met Val Ala Asp Met Val Glu Ser Leu Gln Ser Val Leu Ala Leu
            2340                2345                2350
Gly His Lys Arg Asn Ser Thr Leu Pro Ser Phe Leu Thr Ala Val Leu
            2355                2360                2365
Lys Asn Ile Val Ile Ser Leu Ala Arg Leu Pro Leu Val Asn Ser Tyr
        2370                2375                2380
Thr Arg Val Pro Pro Leu Val Trp Lys Leu Gly Trp Ser Pro Lys Pro
2385                2390                2395                2400
Gly Gly Asp Phe Gly Thr Val Phe Pro Glu Ile Pro Val Glu Phe Leu
            2405                2410                2415
Gln Glu Lys Glu Ile Leu Lys Glu Phe Ile Tyr Arg Ile Asn Thr Leu
            2420                2425                2430
Gly Trp Thr Asn Arg Thr Gln Phe Glu Glu Thr Trp Ala Thr Leu Leu
        2435                2440                2445
Gly Val Leu Val Thr Gln Pro Leu Val Met Glu Gln Glu Glu Ser Pro
2450                2455                2460
Pro Glu Glu Asp Thr Glu Arg Thr Gln Ile His Val Leu Ala Val Gln
2465                2470                2475                2480
Ala Ile Thr Ser Leu Val Leu Ser Ala Met Thr Val Pro Val Ala Gly
                2485                2490                2495
Asn Pro Ala Val Ser Cys Leu Glu Gln Gln Pro Arg Asn Lys Pro Leu
            2500                2505                2510
Lys Ala Leu Asp Thr Arg Phe Gly Arg Lys Leu Ser Met Ile Arg Gly
            2515                2520                2525
Ile Val Glu Gln Glu Ile Gln Glu Met Val Ser Gln Arg Glu Asn Thr
        2530                2535                2540
Ala Thr His His Ser His Gln Ala Trp Asp Pro Val Pro Ser Leu Leu
```

|  |  |  |  |
|---|---|---|---|
| 2545 | 2550 | 2555 | 2560 |

Pro Ala Thr Thr Gly Ala Leu Ile Asn His Asp Lys Leu Leu Gln
      2565      2570      2575

Ile Asn Pro Glu Arg Glu Pro Gly Asn Met Ser Tyr Lys Leu Gly Gln
      2580      2585      2590

Val Ser Ile His Ser Val Trp Leu Gly Asn Asn Ile Thr Pro Leu Arg
      2595      2600      2605

Glu Glu Glu Trp Asp Glu Glu Glu Glu Glu Ser Asp Val Pro Ala
    2610      2615      2620

Pro Thr Ser Pro Pro Val Ser Pro Val Asn Ser Arg Lys His Arg Ala
2625      2630      2635      2640

Gly Val Asp Ile His Ser Cys Ser Gln Phe Leu Leu Glu Leu Tyr Ser
      2645      2650      2655

Arg Trp Ile Leu Pro Ser Ser Ala Ala Arg Arg Thr Pro Val Ile Leu
      2660      2665      2670

Ile Ser Glu Val Val Arg Ser Leu Leu Val Val Ser Asp Leu Phe Thr
      2675      2680      2685

Glu Arg Thr Gln Phe Glu Met Met Tyr Leu Thr Leu Thr Glu Leu Arg
      2690      2695      2700

Arg Val His Pro Ser Glu Asp Glu Ile Leu Ile Gln Tyr Leu Val Pro
2705      2710      2715      2720

Ala Thr Cys Lys Ala Ala Ala Val Leu Gly Met Asp Lys Thr Val Ala
      2725      2730      2735

Glu Pro Val Ser Arg Leu Leu Glu Ser Thr Leu Arg Ser Ser His Leu
      2740      2745      2750

Pro Ser Gln Ile Gly Ala Leu His Gly Ile Leu Tyr Val Leu Glu Cys
      2755      2760      2765

Asp Leu Leu Asp Asp Thr Ala Lys Gln Leu Ile Pro Val Val Ser Asp
    2770      2775      2780

Tyr Leu Leu Ser Asn Leu Lys Gly Ile Ala His Cys Val Asn Ile His
    2785      2790      2795      2800

Ser Gln Gln His Val Leu Val Met Cys Ala Thr Ala Phe Tyr Leu Met
      2805      2810      2815

Glu Asn Tyr Pro Leu Asp Val Gly Pro Glu Phe Ser Ala Ser Val Ile
      2820      2825      2830

Gln Met Cys Gly Val Met Leu Ser Gly Ser Glu Glu Ser Thr Pro Ser
    2835      2840      2845

Ile Ile Tyr His Cys Ala Leu Arg Gly Leu Glu Arg Leu Leu Leu Ser
    2850      2855      2860

Val Gln Leu Ser Arg Leu Asp Thr Glu Ser Leu Gly Lys Leu Ser Val
2865      2870      2875      2880

Gly Arg Val Asn Val His Ser Pro His Arg Ala Met Ala Ala Leu Gly
      2885      2890      2895

Leu Met Leu Thr Cys Met Tyr Thr Gly Lys Glu Lys Ala Ser Pro Gly
      2900      2905      2910

Arg Thr Ser Asp Pro Ser Pro Ala Thr Pro Asp Ser Glu Ser Val Ile
    2915      2920      2925

Val Ala Met Glu Arg Val Ser Val Leu Phe Asp Arg Ile Arg Lys Gly
    2930      2935      2940

Phe Pro Cys Glu Ala Arg Val Val Ala Arg Ile Leu Pro Gln Phe Leu
2945      2950      2955      2960

Asp Asp Phe Phe Pro Pro Gln Asp Val Met Asn Lys Val Ile Gly Glu
      2965      2970      2975

```
Phe  Leu  Ser  Asn  Gln  Gln  Pro  Tyr  Pro  Gln  Phe  Met  Ala  Thr  Val  Val
               2980                2985                         2990

Tyr  Lys  Val  Phe  Gln  Thr  Leu  His  Ser  Ala  Gly  Gln  Ser  Ser  Met  Val
          2995                3000                    3005

Arg  Asp  Trp  Val  Met  Leu  Ser  Leu  Ser  Asn  Phe  Thr  Gln  Arg  Thr  Pro
     3010                3015                    3020

Val  Ala  Met  Ala  Met  Trp  Ser  Leu  Ser  Cys  Phe  Leu  Val  Ser  Ala  Ser
3025                3030                3035                              3040

Thr  Ser  Pro  Trp  Val  Ser  Ala  Ile  Leu  Pro  His  Val  Ile  Ser  Arg  Met
               3045                     3050                         3055

Gly  Lys  Leu  Glu  Leu  Met  Asp  Val  Asn  Leu  Phe  Cys  Leu  Val  Ala  Thr
               3060                3065                         3070

Asp  Phe  Tyr  Arg  His  Gln  Ile  Glu  Glu  Glu  Phe  Asp  Arg  Arg  Ala  Phe
          3075                3080                         3085

Gln  Ser  Val  Phe  Glu  Glu  Glu  Ala  Ala  Pro  Gly  Ser  Pro  Tyr  His  Arg
     3090                     3095                    3100

Leu  Leu  Ala  Cys  Leu  Gln  Asn  Val  His  Lys  Val  Thr  Thr  Cys
3105                     3110                    3115
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GGAGGCTAGA ATGCTTGCAG                                                  20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TCTATGGCTT CTGAGGCGGA                                                  20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TGGCAAGACA ATAGCAGGCA                                                  20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCAGACAGGA CATAGCTAGG                                                                      20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AGTTTGCGTG CTGCCCTGTG                                                                      20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AATTTCATTG TCATTTGCGA                                                                      20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CGATGCGGAG TCAGATGTCA                                                                      20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GGTCTTTTGC TTGTTCGGGT                                                                      20

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ATCTTCAGCA GGGATACGGT TGAC 24

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TGAGAAGAAA GAGAGAAGGG AG 22

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CAGTAAGCCG TCATGG 16

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTGAGTCCGG GCGCCGCAGC TC 22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTGAGTTTGG GCCCGCTGCA GC 22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTAATTGGCT TTTTAAAAAA AA 22

(2) INFORMATION FOR SEQ ID NO:23:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

GTAATTGCAC TTTGAACTGT CT 22

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GTAAGCGCCC CATAATGATG AT 22

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GTAAGAACCG TGTGGATGAT GT 22

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTGGGTGTTT GCTCTGCATT AT 22

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GTGGGCCTTG CTTTTCTTTT TT 22

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:28:

GTAAGTTGTA CCTCTGTATT ATTTTTAAGA　　　　　　　　　　　　　　　　　　　　30

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:29:

GTAAGTTGTA CACTCTGGAT GTTGGTTTTT　　　　　　　　　　　　　　　　　　　　30

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:30:

TTTTCCTCTT GTTTTTTTGT AG　　　　　　　　　　　　　　　　　　　　　　　　22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:31:

TCCTTCTTTT TTTTATTTTT AG　　　　　　　　　　　　　　　　　　　　　　　　22

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:32:

TCTCTCTCTC TTTTTTACTT AG　　　　　　　　　　　　　　　　　　　　　　　　22

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:33:

TTTCTCTTCT TTTTTTGCTT AG 22

( 2 ) INFORMATION FOR SEQ ID NO:34:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

AGTCTCTTCT ATTTCTTTGC AG 22

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

AATCTCTTGT GATTTGTTGT AG 22

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

ATCACTTGTT AACTCCACTT AG 22

( 2 ) INFORMATION FOR SEQ ID NO:37:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

AACCCTCATT GCACCCCCTC AG 22

( 2 ) INFORMATION FOR SEQ ID NO:38:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

GCCGCCGCCG CC 12

( 2 ) INFORMATION FOR SEQ ID NO:39:

( i ) SEQUENCE CHARACTERISTICS:
  ( A ) LENGTH: 9 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:39:

GCCGCCGCC 9

( 2 ) INFORMATION FOR SEQ ID NO:40:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:40:

GACGACGACG ACAACGACGA C 21

( 2 ) INFORMATION FOR SEQ ID NO:41:

( i ) SEQUENCE CHARACTERISTICS:
  ( A ) LENGTH: 10348 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:41:

| | | | | | |
|---|---|---|---|---|---|
| TTGCTGTGTG | AGGCAGAACC | TGCGGGGGCA | GGGGCGGGCT | GGTTCCCTGG | CCAGCCATTG | 60 |
| GCAGAGTCCG | CAGGCTAGGG | CTGTCAATCA | TGCTGGCCGG | CGTGGCCCCG | CCTCCGCCGG | 120 |
| CGCGGCCCCG | CCTCCGCCGG | CGCACGTCTG | GGACGCAAGG | CGCCGTGGGG | GCTGCCGGGA | 180 |
| CGGGTCCAAG | ATGGACGGCC | GCTCAGGTTC | TGCTTTTACC | TGCGGCCCAG | AGCCCCATTC | 240 |
| ATTGCCCCGG | TGCTGAGCGG | CGCCGCGAGT | CGGCCCGAGG | CCTCCGGGGA | CTGCCGTGCC | 300 |
| GGGCGGGAGA | CCGCCATGGC | GACCCTGGAA | AAGCTGATGA | AGGCTTCGA | GTCCCTCAAG | 360 |
| TCCTTCCAGC | AGCAGCAGCA | GCAGCAGCAG | CAGCAGCAGC | AGCAGCAGCA | GCAGCAGCAG | 420 |
| CAGCAGCAGC | AACAGCCGCC | ACCGCCGCCG | CCGCCGCCGC | CGCCTCCTCA | GCTTCCTCAG | 480 |
| CCGCCGCCGC | AGGCACAGCC | GCTGCTGCCT | CAGCCGCAGC | CGCCCCCGCC | GCCGCCCCCG | 540 |
| CCGCCACCCG | CCCGGCTGT | GGCTGAGGAG | CCGCTGCACC | GACCAAAGAA | AGAACTTTCA | 600 |
| GCTACCAAGA | AAGACCGTGT | GAATCATTGT | CTGACAATAT | GTGAAAACAT | AGTGGCACAG | 660 |
| TCTGTCAGAA | ATTCTCCAGA | ATTTCAGAAA | CTTCTGGGCA | TCGCTATGGA | ACTTTTTCTG | 720 |
| CTGTGCAGTG | ATGACGCAGA | GTCAGATGTC | AGGATGGTGG | CTGACGAATG | CCTCAACAAA | 780 |
| GTTATCAAAG | CTTTGATGGA | TTCTAATCTT | CCAAGGTTAC | AGCTCGAGCT | CTATAAGGAA | 840 |
| ATTAAAAAGA | ATGGTGCCCC | TCGGAGTTTG | CGTGCTGCCC | TGTGGAGGTT | TGCTGAGCTG | 900 |
| GCTCACCTGG | TTCGGCCTCA | GAAATGCAGG | CCTTACCTGG | TGAACCTTCT | GCCGTGCCTG | 960 |
| ACTCGAACAA | GCAAGAGACC | CGAAGAATCA | GTCCAGGAGA | CCTTGGCTGC | AGCTGTTCCC | 1020 |
| AAAATTATGG | CTTCTTTTGG | CAATTTTGCA | AATGACAATG | AAATTAAGGT | TTTGTTAAAG | 1080 |
| GCCTTCATAG | CGAACCTGAA | GTCAAGCTCC | CCCACCATTC | GGCGGACAGC | GGCTGGATCA | 1140 |
| GCAGTGAGCA | TCTGCCAGCA | CTCAAGAAGG | ACACAATATT | TCTATAGTTG | GCTACTAAAT | 1200 |

```
GTGCTCTTAG  GCTTACTCGT  TCCTGTCGAG  GATGAACACT  CCACTCTGCT  GATTCTTGGC  1260
GTGCTGCTCA  CCCTGAGGTA  TTTGGTGCCC  TTGCTGCAGC  AGCAGGTCAA  GGACACAAGC  1320
CTGAAAGGCA  GCTTCGGAGT  GACAAGGAAA  GAAATGGAAG  TCTCTCCTTC  TGCAGAGCAG  1380
CTTGTCCAGG  TTTATGAACT  GACGTTACAT  CATACACAGC  ACCAAGACCA  CAATGTTGTG  1440
ACCGGAGCCC  TGGAGCTGTT  GCAGCAGCTC  TTCAGAACGC  CTCCACCCGA  GCTTCTGCAA  1500
ACCCTGACCG  CAGTCGGGGG  CATTGGGCAG  CTCACCGCTG  CTAAGGAGGA  GTCTGGTGGC  1560
CGAAGCCGTA  GTGGGAGTAT  TGTGGAACTT  ATAGCTGGAG  GGGGTTCCTC  ATGCAGCCCT  1620
GTCCTTTCAA  GAAAACAAAA  AGGCAAAGTG  CTCTTAGGAG  AAGAAGAAGC  CTTGGAGGAT  1680
GACTCTGAAT  CGAGATCGGA  TGTCAGCAGC  TCTGCCTTAA  CAGCCTCAGT  GAAGGATGAG  1740
ATCAGTGGAG  AGCTGGCTGC  TTCTTCAGGG  GTTTCCACTC  CAGGGTCAGC  AGGTCATGAC  1800
ATCATCACAG  AACAGCCACG  GTCACAGCAC  ACACTGCAGG  CGGACTCAGT  GGATCTGGCC  1860
AGCTGTGACT  TGACAAGCTC  TGCCACTGAT  GGGGATGAGG  AGGATATCTT  GAGCCACAGC  1920
TCCAGCCAGG  TCAGCGCCGT  CCCATCTGAC  CCTGCCATGG  ACCTGAATGA  TGGGACCCAG  1980
GCCTCGTCGC  CCATCAGCGA  CAGCTCCCAG  ACCACCACCG  AAGGGCCTGA  TTCAGCTGTT  2040
ACCCCTTCAG  ACAGTTCTGA  AATTGTGTTA  GACGGTACCG  ACAACCAGTA  TTTGGGCCTG  2100
CAGATTGGAC  AGCCCCAGGA  TGAAGATGAG  GAAGCCACAG  GTATTCTTCC  TGATGAAGCC  2160
TCGGAGGCCT  TCAGGAACTC  TTCCATGGCC  CTTCAACAGG  CACATTTATT  GAAAAACATG  2220
AGTCACTGCA  GGCAGCCTTC  TGACAGCAGT  GTTGATAAAT  TTGTGTTGAG  AGATGAAGCT  2280
ACTGAACCGG  GTGATCAAGA  AAACAAGCCT  TGCCGCATCA  AAGGTGACAT  GGACAGTCC  2340
ACTGATGATG  ACTCTGCACC  TCTTGTCCAT  TGTGTCCGCC  TTTTATCTGC  TTCGTTTTTG  2400
CTAACAGGGG  GAAAAAATGT  GCTGGTTCCG  GACAGGGATG  TGAGGGTCAG  CGTGAAGGCC  2460
CTGGCCCTCA  GCTGTGTGGG  AGCAGCTGTG  GCCCTCCACC  CGGAATCTTT  CTTCAGCAAA  2520
CTCTATAAAG  TTCCTCTTGA  CACCACGGAA  TACCCTGAGG  AACAGTATGT  CTCAGACATC  2580
TTGAACTACA  TCGATCATGG  AGACCCACAG  GTTCGAGGAG  CCACTGCCAT  TCTCTGTGGG  2640
ACCCTCATCT  GCTCCATCCT  CAGCAGGTCC  CGCTTCCACG  TGGGAGATTG  GATGGGCACC  2700
ATTAGAACCC  TCACAGGAAA  TACATTTCT   TTGGCGGATT  GCATTCCTTT  GCTGCGGAAA  2760
ACACTGAAGG  ATGAGTCTTC  TGTTACTTGC  AAGTTAGCTT  GTACAGCTGT  GAGGAACTGT  2820
GTCATGAGTC  TCTGCAGCAG  CAGCTACAGT  GAGTTAGGAC  TGCAGCTGAT  CATCGATGTG  2880
CTGACTCTGA  GGAACAGTTC  CTATTGGCTG  GTGAGGACAG  AGCTTCTGGA  AACCCTTGCA  2940
GAGATTGACT  TCAGGCTGGT  GAGCTTTTG   GAGGCAAAAG  CAGAAAACTT  ACACAGAGGG  3000
GCTCATCATT  ATACAGGGCT  TTTAAAACTG  CAAGAACGAG  TGCTCAATAA  TGTTGTCATC  3060
CATTTGCTTG  GAGATGAAGA  CCCCAGGGTG  CGACATGTTG  CCGCAGCATC  ACTAATTAGG  3120
CTTGTCCCAA  AGCTGTTTTA  TAAATGTGAC  CAAGGACAAG  CTGATCCAGT  AGTGGCCGTG  3180
GCAAGAGATC  AAAGCAGTGT  TTACCTGAAA  CTTCTCATGC  ATGAGACGCA  GCCTCCATCT  3240
CATTTCTCCG  TCAGCACAAT  AACCAGAATA  TATAGAGGCT  ATAACCTACT  ACCAAGCATA  3300
ACAGACGTCA  CTATGGAAAA  TAACCTTTCA  AGAGTTATTG  CAGCAGTTTC  TCATGAACTA  3360
ATCACATCAA  CCACCAGAGC  ACTCACATTT  GGATGCTGTG  AAGCTTTGTG  TCTTCTTTCC  3420
ACTGCCTTCC  CAGTTTGCAT  TTGGAGTTTA  GGTTGGCACT  GTGGAGTGCC  TCCACTGAGT  3480
GCCTCAGATG  AGTCTAGGAA  GAGCTGTACC  GTTGGGATGG  CCACAATGAT  TCTGACCCTG  3540
CTCTCGTCAG  CTTGGTTCCC  ATTGGATCTC  TCAGCCCATC  AAGATGCTTT  GATTTTGGCC  3600
```

-continued

| | | | | | | |
|---|---|---|---|---|---|---|
| GGAAACTTGC | TTGCAGCCAG | TGCTCCCAAA | TCTCTGAGAA | GTTCATGGGC | CTCTGAAGAA | 3660 |
| GAAGCCAACC | CAGCAGCCAC | CAAGCAAGAG | GAGGTCTGGC | CAGCCCTGGG | GGACCGGGCC | 3720 |
| CTGGTGCCCA | TGGTGGAGCA | GCTCTTCTCT | CACCTGCTGA | AGGTGATTAA | CATTTGTGCC | 3780 |
| CACGTCCTGG | ATGACGTGGC | TCCTGGACCC | GCAATAAAGG | CAGCCTTGCC | TTCTCTAACA | 3840 |
| AACCCCCCTT | CTCTAAGTCC | CATCCGACGA | AAGGGGAAGG | AGAAAGAACC | AGGAGAACAA | 3900 |
| GCATCTGTAC | CGTTGAGTCC | CAAGAAAGGC | AGTGAGGCCA | GTGCAGCTTC | TAGACAATCT | 3960 |
| GATACCTCAG | GTCCTGTTAC | AACAAGTAAA | TCCTCATCAC | TGGGGAGTTT | CTATCATCTT | 4020 |
| CCTTCATACC | TCAAACTGCA | TGATGTCCTG | AAAGCTACAC | ACGCTAACTA | CAAGGTCACG | 4080 |
| CTGGATCTTC | AGAACAGCAC | GGAAAAGTTT | GGAGGGTTTC | TCCGCTCAGC | CTTGGATGTT | 4140 |
| CTTTCTCAGA | TACTAGAGCT | GGCCACACTG | CAGGACATTG | GGAAGTGTGT | TGAAGAGATC | 4200 |
| CTAGGATACC | TGAAATCCTG | CTTTAGTCGA | GAACCAATGA | TGGCAACTGT | TTGTGTTCAA | 4260 |
| CAATTGTTGA | AGACTCTCTT | TGGCACAAAC | TTGGCCTCCC | AGTTTGATGG | CTTATCTTCC | 4320 |
| AACCCCAGCA | AGTCACAAGG | CCGAGCACAG | CGCCTTGGCT | CCTCCAGTGT | GAGGCCAGGC | 4380 |
| TTGTACCACT | ACTGCTTCAT | GGCCCCGTAC | ACCCACTTCA | CCCAGGCCCT | CGCTGACGCC | 4440 |
| AGCCTGAGGA | ACATGGTGCA | GGCGGAGCAG | GAGAACGACA | CCTCGGGATG | GTTTGATGTC | 4500 |
| CTCCAGAAAG | TGTCTACCCA | GTTGAAGACA | AACCTCACGA | GTGTCACAAA | GAACCGTGCA | 4560 |
| GATAAGAATG | CTATTCATAA | TCACATTCGT | TTGTTTGAAC | CTCTTGTTAT | AAAAGCTTTA | 4620 |
| AAACAGTACA | CGACTACAAC | ATGTGTGCAG | TTACAGAAGC | AGGTTTTAGA | TTTGCTGGCG | 4680 |
| CAGCTGGTTC | AGTTACGGGT | TAATTACTGT | CTTCTGGATT | CAGATCAGGT | GTTTATTGGC | 4740 |
| TTTGTATTGA | AACAGTTTGA | ATACATTGAA | GTGGGCCAGT | TCAGGGAATC | AGAGGCAATC | 4800 |
| ATTCCAAACA | TCTTTTTCTT | CTTGGTATTA | CTATCTTATG | AACGCTATCA | TTCAAAACAG | 4860 |
| ATCATTGGAA | TTCCTAAAAT | CATTCAGCTC | TGTGATGGCA | TCATGGCCAG | TGGAAGGAAG | 4920 |
| GCTGTGACAC | ATGCCATACC | GGCTCTGCAG | CCCATAGTCC | ACGACCTCTT | TGTATTAAGA | 4980 |
| GGAACAAATA | AAGCTGATGC | AGGAAAAGAG | CTTGAAACCC | AAAAAGAGGT | GGTGGTGTCA | 5040 |
| ATGTTACTGA | GACTCATCCA | GTACCATCAG | GTGTTGGAGA | TGTTCATTCT | TGTCCTGCAG | 5100 |
| CAGTGCCACA | AGGAGAATGA | AGACAAGTGG | AAGCGACTGT | CTCGACAGAT | AGCTGACATC | 5160 |
| ATCCTCCCAA | TGTTAGCCAA | ACAGCAGATG | CACATTGACT | CTCATGAAGC | CCTTGGAGTG | 5220 |
| TTAAATACAT | TATTTGAGAT | TTTGGCCCCT | TCCTCCCTCC | GTCCGGTAGA | CATGCTTTTA | 5280 |
| CGGAGTATGT | TCGTCACTCC | AAACACAATG | GCGTCCGTGA | GCACTGTTCA | ACTGTGGATA | 5340 |
| TCGGGAATTC | TGGCCATTTT | GAGGGTTCTG | ATTTCCCAGT | CAACTGAAGA | TATTGTTCTT | 5400 |
| TCTCGTATTC | AGGAGCTCTC | CTTCTCTCCG | TATTTAATCT | CCTGTACAGT | AATTAATAGG | 5460 |
| TTAAGAGATG | GGGACAGTAC | TTCAACGCTA | GAAGAACACA | GTGAAGGGAA | ACAAATAAAG | 5520 |
| AATTTGCCAG | AAGAAACATT | TTCAAGGTTT | CTATTACAAC | TGGTTGGTAT | TCTTTTAGAA | 5580 |
| GACATTGTTA | CAAAACAGCT | GAAGGTGGAA | ATGAGTGAGC | AGCAACATAC | TTTCTATTGC | 5640 |
| CAGGAACTAG | GCACACTGCT | AATGTGTCTG | ATCCACATCT | TCAAGTCTGG | AATGTTCCGG | 5700 |
| AGAATCACAG | CAGCTGCCAC | TAGGCTGTTC | CGCAGTGATG | GCTGTGGCGG | CAGTTTCTAC | 5760 |
| ACCCTGGACA | GCTTGAACTT | GCGGGCTCGT | TCCATGATCA | CCACCCACCC | GGCCCTGGTG | 5820 |
| CTGCTCTGGT | GTCAGATACT | GCTGCTTGTC | AACCACACCG | ACTACCGCTG | GTGGGCAGAA | 5880 |
| GTGCAGCAGA | CCCCGAAAAG | ACACAGTCTG | TCCAGCACAA | AGTTACTTAG | TCCCCAGATG | 5940 |
| TCTGGAGAAG | AGGAGGATTC | TGACTTGGCA | GCCAAACTTG | GAATGTGCAA | TAGAGAAATA | 6000 |

| | | | | | | |
|---|---|---|---|---|---|---|
| GTACGAAGAG | GGGCTCTCAT | TCTCTTCTGT | GATTATGTCT | GTCAGAACCT | CCATGACTCC | 6060 |
| GAGCACTTAA | CGTGGCTCAT | TGTAAATCAC | ATTCAAGATC | TGATCAGCCT | TTCCCACGAG | 6120 |
| CCTCCAGTAC | AGGACTTCAT | CAGTGCCGTT | CATCGGAACT | CTGCTGCCAG | CGGCCTGTTC | 6180 |
| ATCCAGGCAA | TTCAGTCTCG | TTGTGAAAAC | CTTTCAACTC | CAACCATGCT | GAAGAAAACT | 6240 |
| CTTCAGTGCT | TGGAGGGGAT | CCATCTCAGC | CAGTCGGGAG | CTGTGCTCAC | GCTGTATGTG | 6300 |
| GACAGGCTTC | TGTGCACCCC | TTTCCGTGTG | CTGGCTCGCA | TGGTCGACAT | CCTTGCTTGT | 6360 |
| CGCCGGGTAG | AAATGCTTCT | GGCTGCAAAT | TTACAGAGCA | GCATGGCCCA | GTTGCCAATG | 6420 |
| GAAGAACTCA | ACAGAATCCA | GGAATACCTT | CAGAGCAGCG | GGCTCGCTCA | GAGACACCAA | 6480 |
| AGGCTCTATT | CCCTGCTGGA | CAGGTTTCGT | CTCTCCACCA | TGCAAGACTC | ACTTAGTCCC | 6540 |
| TCTCCTCCAG | TCTCTTCCCA | CCCGCTGGAC | GGGGATGGGC | ACGTGTCACT | GGAAACAGTG | 6600 |
| AGTCCGGACA | AAGACTGGTA | CGTTCATCTT | GTCAAATCCC | AGTGTTGGAC | CAGGTCAGAT | 6660 |
| TCTGCACTGC | TGGAAGGTGC | AGAGCTGGTG | AATCGGATTC | CTGCTGAAGA | TATGAATGCC | 6720 |
| TTCATGATGA | ACTCGGAGTT | CAACCTAAGC | CTGCTAGCTC | CATGCTTAAG | CCTAGGGATG | 6780 |
| AGTGAAATTT | CTGGTGGCCA | GAAGAGTGCC | CTTTTGAAG | CAGCCCGTGA | GGTGACTCTG | 6840 |
| GCCCGTGTGA | GCGGCACCGT | GCAGCAGCTC | CCTGCTGTCC | ATCATGTCTT | CCAGCCCGAG | 6900 |
| CTGCCTGCAG | AGCCGGCGGC | CTACTGGAGC | AAGTTGAATG | ATCTGTTTGG | GGATGCTGCA | 6960 |
| CTGTATCAGT | CCCTGCCCAC | TCTGGCCCGG | GCCCTGGCAC | AGTACCTGGT | GGTGGTCTCC | 7020 |
| AAACTGCCCA | GTCATTTGCA | CCTTCCTCCT | GAGAAAGAGA | AGGACATTGT | GAAATTCGTG | 7080 |
| GTGGCAACCC | TTGAGGCCCT | GTCCTGGCAT | TTGATCCATG | AGCAGATCCC | GCTGAGTCTG | 7140 |
| GATCTCCAGG | CAGGGCTGGA | CTGCTGCTGC | CTGGCCCTGC | AGCTGCCTGG | CCTCTGGAGC | 7200 |
| GTGGTCTCCT | CCACAGAGTT | TGTGACCCAC | GCCTGCTCCC | TCATCTACTG | TGTGCACTTC | 7260 |
| ATCCTGGAGG | CCGTTGCAGT | GCAGCCTGGA | GAGCAGCTTC | TTAGTCCAGA | AAGAAGGACA | 7320 |
| AATACCCCAA | AAGCCATCAG | CGAGGAGGAG | GAGGAAGTAG | ATCCAAACAC | ACAGAATCCT | 7380 |
| AAGTATATCA | CTGCAGCCTG | TGAGATGGTG | GCAGAAATGG | TGGAGTCTCT | GCAGTCGGTG | 7440 |
| TTGGCCTTGG | GTCATAAAAG | GAATAGCGGC | GTGCCGGCGT | TTCTCACGCC | ATTGCTCAGG | 7500 |
| AACATCATCA | TCAGCCTGGC | CCGCCTGCCC | CTTGTCAACA | GCTACACACG | TGTGCCCCCA | 7560 |
| CTGGTGTGGA | AGCTTGGATG | GTCACCCAAA | CCGGGAGGGG | ATTTTGGCAC | AGCATTCCCT | 7620 |
| GAGATCCCCG | TGGAGTTCCT | CCAGGAAAAG | GAAGTCTTTA | AGGAGTTCAT | CTACCGCATC | 7680 |
| AACACACTAG | GCTGGACCAG | TCGTACTCAG | TTTGAAGAAA | CTTGGGCCAC | CCTCCTTGGT | 7740 |
| GTCCTGGTGA | CGCAGCCCCT | CGTGATGGAG | CAGGAGGAGA | GCCCACCAGA | AGAAGACACA | 7800 |
| GAGAGGACCC | AGATCAACGT | CCTGGCCGTG | CAGGCCATCA | CCTCACTGGT | GCTCAGTGCA | 7860 |
| ATGACTGTGC | CTGTGGCCGG | CAACCCAGCT | GTAAGCTGCT | GGAGCAGCA | GCCCCGGAAC | 7920 |
| AAGCCTCTGA | AAGCTCTCGA | CACCAGGTTT | GGGAGGAAGC | TGAGCATTAT | CAGAGGGATT | 7980 |
| GTGGAGCAAG | AGATTCAAGC | AATGGTTTCA | AAGAGAGAGA | ATATTGCCAC | CCATCATTTA | 8040 |
| TATCAGGCAT | GGGATCCTGT | CCCTTCTCTG | TCTCCGGCTA | CTACAGGTGC | CCTCATCAGC | 8100 |
| CACGAGAAGC | TGCTGCTACA | GATCAACCCC | GAGCGGGAGC | TGGGGAGCAT | GAGCTACAAA | 8160 |
| CTCGGCCAGG | TGTCCATACA | CTCCGTGTGG | CTGGGAACA | GCATCACACC | CCTGAGGGAG | 8220 |
| GAGGAATGGG | ACGAGGAAGA | GGAGGAGGAG | GCCGACGCCC | CTGCACCTTC | GTCACCACCC | 8280 |
| ACGTCTCCAG | TCAACTCCAG | GAAACACCGG | GCTGGAGTTG | ACATCCACTC | CTGTTCGCAG | 8340 |
| TTTTTGCTTG | AGTTGTACAG | CCGCTGGATC | CTGCCGTCCA | GCTCAGCCAG | GAGGACCCCG | 8400 |

| | | | | | | |
|---|---|---|---|---|---|---|
| GCCATCCTGA | TCAGTGAGGT | GGTCAGATCC | CTTCTAGTGG | TCTCAGACTT | GTTCACCGAG | 8460 |
| CGCAACCAGT | TTGAGCTGAT | GTATGTGACG | CTGACAGAAC | TGCGAAGGGT | GCACCCTTCA | 8520 |
| GAAGACGAGA | TCCTCGCTCA | GTACCTGGTG | CCTGCCACCT | GCAAGGCAGC | TGCCGTCCTT | 8580 |
| GGGATGGACA | AGGCCGTGGC | GGAGCCTGTC | AGCCGCCTGC | TGGAGAGCAC | GCTCAGGAGC | 8640 |
| AGCCACCTGC | CCAGCAGGGT | TGGAGCCCTG | CACGGCGTCC | TCTATGTGCT | GGAGTGCGAC | 8700 |
| CTGCTGGACG | ACACTGCCAA | GCAGCTCATC | CCGGTCATCA | GCGACTATCT | CCTCTCCAAC | 8760 |
| CTGAAAGGGA | TCGCCCACTG | CGTGAACATT | CACAGCCAGC | AGCACGTACT | GGTCATGTGT | 8820 |
| GCCACTGCGT | TTTACCTCAT | TGAGAACTAT | CCTCTGGACG | TAGGGCCGGA | ATTTTCAGCA | 8880 |
| TCAATAATAC | AGATGTGTGG | GGTGATGCTG | TCTGGAAGTG | AGGAGTCCAC | CCCCTCCATC | 8940 |
| ATTTACCACT | GTGCCCTCAG | AGGCCTGGAG | CGCCTCCTGC | TCTCTGAGCA | GCTCTCCCGC | 9000 |
| CTGGATGCAG | AATCGCTGGT | CAAGCTGAGT | GTGGACAGAG | TGAACGTGCA | CAGCCCGCAC | 9060 |
| CGGGCCATGG | CGGCTCTGGG | CCTGATGCTC | ACCTGCATGT | ACACAGGAAA | GGAGAAAGTC | 9120 |
| AGTCCGGGTA | GAACTTCAGA | CCCTAATCCT | GCAGCCCCG | ACAGCGAGTC | AGTGATTGTT | 9180 |
| GCTATGGAGC | GGGTATCTGT | TCTTTTTGAT | AGGATCAGGA | AAGGCTTTCC | TTGTGAAGCC | 9240 |
| AGAGTGGTGG | CCAGGATCCT | GCCCCAGTTT | CTAGACGACT | TCTTCCCACC | CCAGGACATC | 9300 |
| ATGAACAAAG | TCATCGGAGA | GTTTCTGTCC | AACCAGCAGC | CATACCCCA | GTTCATGGCC | 9360 |
| ACCGTGGTGT | ATAAGGTGTT | TCAGACTCTG | CACAGCACCG | GGCAGTCGTC | CATGGTCCGG | 9420 |
| GACTGGGTCA | TGCTGTCCCT | CTCCAACTTC | ACGCAGAGGG | CCCCGGTCGC | CATGGCCACG | 9480 |
| TGGAGCCTCT | CCTGCTTCTT | TGTCAGCGCG | TCCACCAGCC | CGTGGGTCGC | GGCGATCCTC | 9540 |
| CCACATGTCA | TCAGCAGGAT | GGGCAAGCTG | GAGCAGGTGG | ACGTGAACCT | TTTCTGCCTG | 9600 |
| GTCGCCACAG | ACTTCTACAG | ACACCAGATA | GAGGAGGAGC | TCGACCGCAG | GGCCTTCCAG | 9660 |
| TCTGTGCTTG | AGGTGGTTGC | AGCCCCAGGA | AGCCCATATC | ACCGGCTGCT | GACTTGTTTA | 9720 |
| CGAAATGTCC | ACAAGGTCAC | CACCTGCTGA | GCGCCATGGT | GGGAGAGACT | GTGAGGCGGC | 9780 |
| AGCTGGGGCC | GGAGCCTTTG | GAAGTCTGTG | CCCTTGTGCC | CTGCCTCCAC | CGAGCCAGCT | 9840 |
| TGGTCCCTAT | GGGCTTCCGC | ACATGCCGCG | GGCGGCCAGG | CAACGTGCGT | GTCTCTGCCA | 9900 |
| TGTGGCAGAA | GTGCTCTTTG | TGGCAGTGGC | CAGGCAGGGA | GTGTCTGCAG | TCCTGGTGGG | 9960 |
| GCTGAGCCTG | AGGCCTTCCA | GAAAGCAGGA | GCAGCTGTGC | TGCACCCAT | GTGGGTGACC | 10020 |
| AGGTCCTTTC | TCCTGATAGT | CACCTGCTGG | TTGTTGCCAG | GTTGCAGCTG | CTCTTGCATC | 10080 |
| TGGGCCAGAA | GTCCTCCCTC | CTGCAGGCTG | GCTGTTGGCC | CCTCTGCTGT | CCTGCAGTAG | 10140 |
| AAGGTGCCGT | GAGCAGGCTT | TGGGAACACT | GGCCTGGGTC | TCCCTGGTGG | GGTGTGCATG | 10200 |
| CCACGCCCCG | TGTCTGGATG | CACAGATGCC | ATGGCCTGTG | CTGGGCCAGT | GGCTGGGGGT | 10260 |
| GCTAGACACC | CGGCACCATT | CTCCCTTCTC | TCTTTTCTTC | TCAGGATTTA | AAATTTAATT | 10320 |
| ATATCAGTAA | AGAGATTAAT | TTTAACGT | | | | 10348 |

( 2 ) INFORMATION FOR SEQ ID NO:42:

( i ) SEQUENCE CHARACTERISTICS:
        ( A ) LENGTH: 3144 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Met Ala Thr Leu Glu Lys Leu Met Lys Ala Phe Glu Ser Leu Lys Ser

```
  1               5                          10                         15

Phe Gln Gln Gln Gln Gln Gln Gln Gln Gln Gln Gln Gln Gln Gln
            20                  25                    30

Gln Gln Gln Gln Gln Gln Gln Gln Pro Pro Pro Pro Pro Pro Pro
        35                  40                    45

Pro Pro Pro Gln Leu Pro Gln Pro Pro Gln Ala Gln Pro Leu Leu
        50                  55                    60

Pro Gln Pro Gln Pro Pro Pro Pro Pro Pro Pro Pro Pro Gly Pro
65              70                  75                    80

Ala Val Ala Glu Glu Pro Leu His Arg Pro Lys Lys Glu Leu Ser Ala
            85                  90                    95

Thr Lys Lys Asp Arg Val Asn His Cys Leu Thr Ile Cys Glu Asn Ile
            100                 105                   110

Val Ala Gln Ser Val Arg Asn Ser Pro Glu Phe Gln Lys Leu Leu Gly
            115                 120                   125

Ile Ala Met Glu Leu Phe Leu Leu Cys Ser Asp Asp Ala Glu Ser Asp
        130                 135                   140

Val Arg Met Val Ala Asp Glu Cys Leu Asn Lys Val Ile Lys Ala Leu
145                 150                 155                   160

Met Asp Ser Asn Leu Pro Arg Leu Gln Leu Glu Leu Tyr Lys Glu Ile
                165                 170                   175

Lys Lys Asn Gly Ala Pro Arg Ser Leu Arg Ala Ala Leu Trp Arg Phe
            180                 185                   190

Ala Glu Leu Ala His Leu Val Arg Pro Gln Lys Cys Arg Pro Tyr Leu
        195                 200                   205

Val Asn Leu Leu Pro Cys Leu Thr Arg Thr Ser Lys Arg Pro Glu Glu
        210                 215                   220

Ser Val Gln Glu Thr Leu Ala Ala Ala Val Pro Lys Ile Met Ala Ser
225                 230                 235                   240

Phe Gly Asn Phe Ala Asn Asp Asn Glu Ile Lys Val Leu Leu Lys Ala
                245                 250                   255

Phe Ile Ala Asn Leu Lys Ser Ser Ser Pro Thr Ile Arg Arg Thr Ala
        260                 265                   270

Ala Gly Ser Ala Val Ser Ile Cys Gln His Ser Arg Arg Thr Gln Tyr
        275                 280                   285

Phe Tyr Ser Trp Leu Leu Asn Val Leu Leu Gly Leu Leu Val Pro Val
290                 295                 300

Glu Asp Glu His Ser Thr Leu Leu Ile Leu Gly Val Leu Leu Thr Leu
305                 310                 315                   320

Arg Tyr Leu Val Pro Leu Leu Gln Gln Gln Val Lys Asp Thr Ser Leu
                325                 330                   335

Lys Gly Ser Phe Gly Val Thr Arg Lys Glu Met Glu Val Ser Pro Ser
                340                 345                   350

Ala Glu Gln Leu Val Gln Val Tyr Glu Leu Thr Leu His His Thr Gln
        355                 360                   365

His Gln Asp His Asn Val Val Thr Gly Ala Leu Glu Leu Leu Gln Gln
        370                 375                   380

Leu Phe Arg Thr Pro Pro Pro Glu Leu Leu Gln Thr Leu Thr Ala Val
385                 390                 395                   400

Gly Gly Ile Gly Gln Leu Thr Ala Ala Lys Glu Glu Ser Gly Gly Arg
                405                 410                   415

Ser Arg Ser Gly Ser Ile Val Glu Leu Ile Ala Gly Gly Gly Ser Ser
            420                 425                   430
```

```
Cys  Ser  Pro  Val  Leu  Ser  Arg  Lys  Gln  Lys  Gly  Lys  Val  Leu  Leu  Gly
          435                      440                     445

Glu  Glu  Glu  Ala  Leu  Glu  Asp  Asp  Ser  Glu  Ser  Arg  Ser  Asp  Val  Ser
450                           455                     460

Ser  Ser  Ala  Leu  Thr  Ala  Ser  Val  Lys  Asp  Glu  Ile  Ser  Gly  Glu  Leu
465                      470                     475                          480

Ala  Ala  Ser  Ser  Gly  Val  Ser  Thr  Pro  Gly  Ser  Ala  Gly  His  Asp  Ile
               485                          490                     495

Ile  Thr  Glu  Gln  Pro  Arg  Ser  Gln  His  Thr  Leu  Gln  Ala  Asp  Ser  Val
               500                 505                          510

Asp  Leu  Ala  Ser  Cys  Asp  Leu  Thr  Ser  Ser  Ala  Thr  Asp  Gly  Asp  Glu
               515                 520                          525

Glu  Asp  Ile  Leu  Ser  His  Ser  Ser  Gln  Val  Ser  Ala  Val  Pro  Ser
     530                      535                     540

Asp  Pro  Ala  Met  Asp  Leu  Asn  Asp  Gly  Thr  Gln  Ala  Ser  Ser  Pro  Ile
545                      550                 555                          560

Ser  Asp  Ser  Ser  Gln  Thr  Thr  Thr  Glu  Gly  Pro  Asp  Ser  Ala  Val  Thr
               565                      570                          575

Pro  Ser  Asp  Ser  Ser  Glu  Ile  Val  Leu  Asp  Gly  Thr  Asp  Asn  Gln  Tyr
          580                      585                     590

Leu  Gly  Leu  Gln  Ile  Gly  Gln  Pro  Gln  Asp  Glu  Asp  Glu  Glu  Ala  Thr
          595                      600                     605

Gly  Ile  Leu  Pro  Asp  Glu  Ala  Ser  Glu  Ala  Phe  Arg  Asn  Ser  Ser  Met
     610                      615                     620

Ala  Leu  Gln  Gln  Ala  His  Leu  Leu  Lys  Asn  Met  Ser  His  Cys  Arg  Gln
625                           630                 635                          640

Pro  Ser  Asp  Ser  Ser  Val  Asp  Lys  Phe  Val  Leu  Arg  Asp  Glu  Ala  Thr
               645                      650                          655

Glu  Pro  Gly  Asp  Gln  Glu  Asn  Lys  Pro  Cys  Arg  Ile  Lys  Gly  Asp  Ile
               660                      665                     670

Gly  Gln  Ser  Thr  Asp  Asp  Asp  Ser  Ala  Pro  Leu  Val  His  Cys  Val  Arg
          675                      680                     685

Leu  Leu  Ser  Ala  Ser  Phe  Leu  Leu  Thr  Gly  Gly  Lys  Asn  Val  Leu  Val
     690                      695                     700

Pro  Asp  Arg  Asp  Val  Arg  Val  Ser  Val  Lys  Ala  Leu  Ala  Leu  Ser  Cys
705                           710                     715                      720

Val  Gly  Ala  Ala  Val  Ala  Leu  His  Pro  Glu  Ser  Phe  Phe  Ser  Lys  Leu
                    725                     730                          735

Tyr  Lys  Val  Pro  Leu  Asp  Thr  Thr  Glu  Tyr  Pro  Glu  Glu  Gln  Tyr  Val
               740                     745                          750

Ser  Asp  Ile  Leu  Asn  Tyr  Ile  Asp  His  Gly  Asp  Pro  Gln  Val  Arg  Gly
          755                      760                     765

Ala  Thr  Ala  Ile  Leu  Cys  Gly  Thr  Leu  Ile  Cys  Ser  Ile  Leu  Ser  Arg
770                           775                     780

Ser  Arg  Phe  His  Val  Gly  Asp  Trp  Met  Gly  Thr  Ile  Arg  Thr  Leu  Thr
785                      790                      795                          800

Gly  Asn  Thr  Phe  Ser  Leu  Ala  Asp  Cys  Ile  Pro  Leu  Leu  Arg  Lys  Thr
                    805                      810                          815

Leu  Lys  Asp  Glu  Ser  Ser  Val  Thr  Cys  Lys  Leu  Ala  Cys  Thr  Ala  Val
               820                      825                     830

Arg  Asn  Cys  Val  Met  Ser  Leu  Cys  Ser  Ser  Ser  Tyr  Ser  Glu  Leu  Gly
          835                      840                     845

Leu  Gln  Leu  Ile  Ile  Asp  Val  Leu  Thr  Leu  Arg  Asn  Ser  Ser  Tyr  Trp
     850                      855                     860
```

```
Leu  Val  Arg  Thr  Glu  Leu  Leu  Glu  Thr  Leu  Ala  Glu  Ile  Asp  Phe  Arg
865            870                 875                 880

Leu  Val  Ser  Phe  Leu  Glu  Ala  Lys  Ala  Glu  Asn  Leu  His  Arg  Gly  Ala
               885                 890                 895

His  His  Tyr  Thr  Gly  Leu  Leu  Lys  Leu  Gln  Glu  Arg  Val  Leu  Asn  Asn
               900                 905                 910

Val  Val  Ile  His  Leu  Leu  Gly  Asp  Glu  Asp  Pro  Arg  Val  Arg  His  Val
          915                 920                 925

Ala  Ala  Ala  Ser  Leu  Ile  Arg  Leu  Val  Pro  Lys  Leu  Phe  Tyr  Lys  Cys
930                      935                 940

Asp  Gln  Gly  Gln  Ala  Asp  Pro  Val  Val  Ala  Val  Ala  Arg  Asp  Gln  Ser
945                      950                 955                      960

Ser  Val  Tyr  Leu  Lys  Leu  Leu  Met  His  Glu  Thr  Gln  Pro  Pro  Ser  His
                    965                 970                      975

Phe  Ser  Val  Ser  Thr  Ile  Thr  Arg  Ile  Tyr  Arg  Gly  Tyr  Asn  Leu  Leu
               980                 985                      990

Pro  Ser  Ile  Thr  Asp  Val  Thr  Met  Glu  Asn  Asn  Leu  Ser  Arg  Val  Ile
          995                 1000                1005

Ala  Ala  Val  Ser  His  Glu  Leu  Ile  Thr  Ser  Thr  Arg  Ala  Leu  Thr
     1010                1015                1020

Phe  Gly  Cys  Cys  Glu  Ala  Leu  Cys  Leu  Leu  Ser  Thr  Ala  Phe  Pro  Val
1025                1030                1035                     1040

Cys  Ile  Trp  Ser  Leu  Gly  Trp  His  Cys  Gly  Val  Pro  Pro  Leu  Ser  Ala
               1045                1050                1055

Ser  Asp  Glu  Ser  Arg  Lys  Ser  Cys  Thr  Val  Gly  Met  Ala  Thr  Met  Ile
               1060                1065                1070

Leu  Thr  Leu  Leu  Ser  Ser  Ala  Trp  Phe  Pro  Leu  Asp  Leu  Ser  Ala  His
               1075                1080                1085

Gln  Asp  Ala  Leu  Ile  Leu  Ala  Gly  Asn  Leu  Leu  Ala  Ala  Ser  Ala  Pro
               1090                1095                1100

Lys  Ser  Leu  Arg  Ser  Ser  Trp  Ala  Ser  Glu  Glu  Ala  Asn  Pro  Ala
1105                1110                1115                     1120

Ala  Thr  Lys  Gln  Glu  Glu  Val  Trp  Pro  Ala  Leu  Gly  Asp  Arg  Ala  Leu
               1125                1130                1135

Val  Pro  Met  Val  Glu  Gln  Leu  Phe  Ser  His  Leu  Leu  Lys  Val  Ile  Asn
               1140                1145                1150

Ile  Cys  Ala  His  Val  Leu  Asp  Asp  Val  Ala  Pro  Gly  Pro  Ala  Ile  Lys
               1155                1160                1165

Ala  Ala  Leu  Pro  Ser  Leu  Thr  Asn  Pro  Pro  Ser  Leu  Ser  Pro  Ile  Arg
     1170                1175                1180

Arg  Lys  Gly  Lys  Glu  Lys  Glu  Pro  Gly  Glu  Gln  Ala  Ser  Val  Pro  Leu
1185                1190                1195                     1200

Ser  Pro  Lys  Lys  Gly  Ser  Glu  Ala  Ser  Ala  Ala  Ser  Arg  Gln  Ser  Asp
               1205                1210                1215

Thr  Ser  Gly  Pro  Val  Thr  Thr  Ser  Lys  Ser  Ser  Ser  Leu  Gly  Ser  Phe
               1220                1225                1230

Tyr  His  Leu  Pro  Ser  Tyr  Leu  Lys  Leu  His  Asp  Val  Leu  Lys  Ala  Thr
               1235                1240                1245

His  Ala  Asn  Tyr  Lys  Val  Thr  Leu  Asp  Leu  Gln  Asn  Ser  Thr  Glu  Lys
     1250                1255                1260

Phe  Gly  Gly  Phe  Leu  Arg  Ser  Ala  Leu  Asp  Val  Leu  Ser  Gln  Ile  Leu
1265                1270                1275                     1280

Glu  Leu  Ala  Thr  Leu  Gln  Asp  Ile  Gly  Lys  Cys  Val  Glu  Glu  Ile  Leu
```

-continued

```
                    1285                       1290                      1295
        Gly Tyr Leu Lys Ser Cys Phe Ser Arg Glu Pro Met Met Ala Thr Val
                            1300                1305                1310
        Cys Val Gln Gln Leu Leu Lys Thr Leu Phe Gly Thr Asn Leu Ala Ser
                    1315                1320                1325
        Gln Phe Asp Gly Leu Ser Ser Asn Pro Ser Lys Ser Gln Gly Arg Ala
                    1330                1335                1340
        Gln Arg Leu Gly Ser Ser Ser Val Arg Pro Gly Leu Tyr His Tyr Cys
        1345                1350                1355                1360
        Phe Met Ala Pro Tyr Thr His Phe Thr Gln Ala Leu Ala Asp Ala Ser
                            1365                1370                1375
        Leu Arg Asn Met Val Gln Ala Glu Gln Glu Asn Asp Thr Ser Gly Trp
                    1380                1385                1390
        Phe Asp Val Leu Gln Lys Val Ser Thr Gln Leu Lys Thr Asn Leu Thr
                    1395                1400                1405
        Ser Val Thr Lys Asn Arg Ala Asp Lys Asn Ala Ile His Asn His Ile
                    1410                1415                1420
        Arg Leu Phe Glu Pro Leu Val Ile Lys Ala Leu Lys Gln Tyr Thr Thr
        1425                1430                1435                1440
        Thr Thr Cys Val Gln Leu Gln Lys Gln Val Leu Asp Leu Leu Ala Gln
                            1445                1450                1455
        Leu Val Gln Leu Arg Val Asn Tyr Cys Leu Leu Asp Ser Asp Gln Val
                            1460                1465                1470
        Phe Ile Gly Phe Val Leu Lys Gln Phe Glu Tyr Ile Glu Val Gly Gln
                    1475                1480                1485
        Phe Arg Glu Ser Glu Ala Ile Ile Pro Asn Ile Phe Phe Phe Leu Val
                    1490                1495                1500
        Leu Leu Ser Tyr Glu Arg Tyr His Ser Lys Gln Ile Ile Gly Ile Pro
        1505                1510                1515                1520
        Lys Ile Ile Gln Leu Cys Asp Gly Ile Met Ala Ser Gly Arg Lys Ala
                            1525                1530                1535
        Val Thr His Ala Ile Pro Ala Leu Gln Pro Ile Val His Asp Leu Phe
                    1540                1545                1550
        Val Leu Arg Gly Thr Asn Lys Ala Asp Ala Gly Lys Glu Leu Glu Thr
                    1555                1560                1565
        Gln Lys Glu Val Val Val Ser Met Leu Leu Arg Leu Ile Gln Tyr His
        1570                1575                1580
        Gln Val Leu Glu Met Phe Ile Leu Val Leu Gln Gln Cys His Lys Glu
        1585                1590                1595                1600
        Asn Glu Asp Lys Trp Lys Arg Leu Ser Arg Gln Ile Ala Asp Ile Ile
                            1605                1610                1615
        Leu Pro Met Leu Ala Lys Gln Gln Met His Ile Asp Ser His Glu Ala
                    1620                1625                1630
        Leu Gly Val Leu Asn Thr Leu Phe Glu Ile Leu Ala Pro Ser Ser Leu
                    1635                1640                1645
        Arg Pro Val Asp Met Leu Leu Arg Ser Met Phe Val Thr Pro Asn Thr
                    1650                1655                1660
        Met Ala Ser Val Ser Thr Val Gln Leu Trp Ile Ser Gly Ile Leu Ala
        1665                1670                1675                1680
        Ile Leu Arg Val Leu Ile Ser Gln Ser Thr Glu Asp Ile Val Leu Ser
                            1685                1690                1695
        Arg Ile Gln Glu Leu Ser Phe Ser Pro Tyr Leu Ile Ser Cys Thr Val
                    1700                1705                1710
```

```
Ile Asn Arg Leu Arg Asp Gly Asp Ser Thr Ser Thr Leu Glu Glu His
        1715                1720                1725

Ser Glu Gly Lys Gln Ile Lys Asn Leu Pro Glu Glu Thr Phe Ser Arg
        1730                1735                1740

Phe Leu Leu Gln Leu Val Gly Ile Leu Leu Glu Asp Ile Val Thr Lys
1745                1750                1755                1760

Gln Leu Lys Val Glu Met Ser Glu Gln Gln His Thr Phe Tyr Cys Gln
        1765                1770                1775

Glu Leu Gly Thr Leu Leu Met Cys Leu Ile His Ile Phe Lys Ser Gly
        1780                1785                1790

Met Phe Arg Arg Ile Thr Ala Ala Ala Thr Arg Leu Phe Arg Ser Asp
        1795                1800                1805

Gly Cys Gly Gly Ser Phe Tyr Thr Leu Asp Ser Leu Asn Leu Arg Ala
        1810                1815                1820

Arg Ser Met Ile Thr Thr His Pro Ala Leu Val Leu Leu Trp Cys Gln
1825                1830                1835                1840

Ile Leu Leu Leu Val Asn His Thr Asp Tyr Arg Trp Trp Ala Glu Val
        1845                1850                1855

Gln Gln Thr Pro Lys Arg His Ser Leu Ser Ser Thr Lys Leu Leu Ser
        1860                1865                1870

Pro Gln Met Ser Gly Glu Glu Asp Ser Asp Leu Ala Ala Lys Leu
        1875                1880                1885

Gly Met Cys Asn Arg Glu Ile Val Arg Arg Gly Ala Leu Ile Leu Phe
        1890                1895                1900

Cys Asp Tyr Val Cys Gln Asn Leu His Asp Ser Glu His Leu Thr Trp
1905                1910                1915                1920

Leu Ile Val Asn His Ile Gln Asp Leu Ile Ser Leu Ser His Glu Pro
        1925                1930                1935

Pro Val Gln Asp Phe Ile Ser Ala Val His Arg Asn Ser Ala Ala Ser
        1940                1945                1950

Gly Leu Phe Ile Gln Ala Ile Gln Ser Arg Cys Glu Asn Leu Ser Thr
        1955                1960                1965

Pro Thr Met Leu Lys Lys Thr Leu Gln Cys Leu Glu Gly Ile His Leu
        1970                1975                1980

Ser Gln Ser Gly Ala Val Leu Thr Leu Tyr Val Asp Arg Leu Leu Cys
1985                1990                1995                2000

Thr Pro Phe Arg Val Leu Ala Arg Met Val Asp Ile Leu Ala Cys Arg
                2005                2010                2015

Arg Val Glu Met Leu Leu Ala Ala Asn Leu Gln Ser Ser Met Ala Gln
                2020                2025                2030

Leu Pro Met Glu Glu Leu Asn Arg Ile Gln Glu Tyr Leu Gln Ser Ser
                2035                2040                2045

Gly Leu Ala Gln Arg His Gln Arg Leu Tyr Ser Leu Leu Asp Arg Phe
        2050                2055                2060

Arg Leu Ser Thr Met Gln Asp Ser Leu Ser Pro Ser Pro Pro Val Ser
2065                2070                2075                2080

Ser His Pro Leu Asp Gly Asp Gly His Val Ser Leu Glu Thr Val Ser
                2085                2090                2095

Pro Asp Lys Asp Trp Tyr Val His Leu Val Lys Ser Gln Cys Trp Thr
                2100                2105                2110

Arg Ser Asp Ser Ala Leu Leu Glu Gly Ala Glu Leu Val Asn Arg Ile
        2115                2120                2125

Pro Ala Glu Asp Met Asn Ala Phe Met Met Asn Ser Glu Phe Asn Leu
        2130                2135                2140
```

```
Ser Leu Leu Ala Pro Cys Leu Ser Leu Gly Met Ser Glu Ile Ser Gly
2145                2150                2155                2160

Gly Gln Lys Ser Ala Leu Phe Glu Ala Ala Arg Glu Val Thr Leu Ala
            2165                2170                2175

Arg Val Ser Gly Thr Val Gln Gln Leu Pro Ala Val His His Val Phe
        2180                2185                2190

Gln Pro Glu Leu Pro Ala Glu Pro Ala Ala Tyr Trp Ser Lys Leu Asn
    2195                2200                2205

Asp Leu Phe Gly Asp Ala Ala Leu Tyr Gln Ser Leu Pro Thr Leu Ala
2210                2215                2220

Arg Ala Leu Ala Gln Tyr Leu Val Val Ser Lys Leu Pro Ser His
2225                2230                2235                2240

Leu His Leu Pro Pro Glu Lys Glu Lys Asp Ile Val Lys Phe Val Val
            2245                2250                2255

Ala Thr Leu Glu Ala Leu Ser Trp His Leu Ile His Glu Gln Ile Pro
            2260                2265                2270

Leu Ser Leu Asp Leu Gln Ala Gly Leu Asp Cys Cys Leu Ala Leu
            2275                2280                2285

Gln Leu Pro Gly Leu Trp Ser Val Val Ser Ser Thr Glu Phe Val Thr
2290                2295                2300

His Ala Cys Ser Leu Ile Tyr Cys Val His Phe Ile Leu Glu Ala Val
2305                2310                2315                2320

Ala Val Gln Pro Gly Glu Gln Leu Leu Ser Pro Glu Arg Arg Thr Asn
            2325                2330                2335

Thr Pro Lys Ala Ile Ser Glu Glu Glu Glu Val Asp Pro Asn Thr
            2340                2345                2350

Gln Asn Pro Lys Tyr Ile Thr Ala Ala Cys Glu Met Val Ala Glu Met
            2355                2360                2365

Val Glu Ser Leu Gln Ser Val Leu Ala Leu Gly His Lys Arg Asn Ser
            2370                2375                2380

Gly Val Pro Ala Phe Leu Thr Pro Leu Leu Arg Asn Ile Ile Ile Ser
2385                2390                2395                2400

Leu Ala Arg Leu Pro Leu Val Asn Ser Tyr Thr Arg Val Pro Pro Leu
            2405                2410                2415

Val Trp Lys Leu Gly Trp Ser Pro Lys Pro Gly Gly Asp Phe Gly Thr
            2420                2425                2430

Ala Phe Pro Glu Ile Pro Val Glu Phe Leu Gln Glu Lys Glu Val Phe
            2435                2440                2445

Lys Glu Phe Ile Tyr Arg Ile Asn Thr Leu Gly Trp Thr Ser Arg Thr
            2450                2455                2460

Gln Phe Glu Glu Thr Trp Ala Thr Leu Leu Gly Val Leu Val Thr Gln
2465                2470                2475                2480

Pro Leu Val Met Glu Gln Glu Glu Ser Pro Pro Glu Glu Asp Thr Glu
            2485                2490                2495

Arg Thr Gln Ile Asn Val Leu Ala Val Gln Ala Ile Thr Ser Leu Val
            2500                2505                2510

Leu Ser Ala Met Thr Val Pro Val Ala Gly Asn Pro Ala Val Ser Cys
            2515                2520                2525

Leu Glu Gln Gln Pro Arg Asn Lys Pro Leu Lys Ala Leu Asp Thr Arg
            2530                2535                2540

Phe Gly Arg Lys Leu Ser Ile Ile Arg Gly Ile Val Glu Gln Glu Ile
2545                2550                2555                2560

Gln Ala Met Val Ser Lys Arg Glu Asn Ile Ala Thr His His Leu Tyr
```

```
                               2565                        2570                        2575
        Gln  Ala  Trp  Asp  Pro  Val  Pro  Ser  Leu  Ser  Pro  Ala  Thr  Thr  Gly  Ala
                       2580                      2585                      2590

Leu  Ile  Ser  His  Glu  Lys  Leu  Leu  Leu  Gln  Ile  Asn  Pro  Glu  Arg  Glu
                       2595                      2600                      2605

Leu  Gly  Ser  Met  Ser  Tyr  Lys  Leu  Gly  Gln  Val  Ser  Ile  His  Ser  Val
                       2610                      2615                      2620

Trp  Leu  Gly  Asn  Ser  Ile  Thr  Pro  Leu  Arg  Glu  Glu  Glu  Trp  Asp  Glu
        2625                      2630                      2635                      2640

Glu  Glu  Glu  Glu  Glu  Ala  Asp  Ala  Pro  Ala  Pro  Ser  Ser  Pro  Pro  Thr
                       2645                      2650                      2655

Ser  Pro  Val  Asn  Ser  Arg  Lys  His  Arg  Ala  Gly  Val  Asp  Ile  His  Ser
                       2660                      2665                      2670

Cys  Ser  Gln  Phe  Leu  Leu  Glu  Leu  Tyr  Ser  Arg  Trp  Ile  Leu  Pro  Ser
                       2675                      2680                      2685

Ser  Ser  Ala  Arg  Arg  Thr  Pro  Ala  Ile  Leu  Ile  Ser  Glu  Val  Val  Arg
                       2690                      2695                      2700

Ser  Leu  Leu  Val  Val  Ser  Asp  Leu  Phe  Thr  Glu  Arg  Asn  Gln  Phe  Glu
        2705                      2710                      2715                      2720

Leu  Met  Tyr  Val  Thr  Leu  Thr  Glu  Leu  Arg  Arg  Val  His  Pro  Ser  Glu
                       2725                      2730                      2735

Asp  Glu  Ile  Leu  Ala  Gln  Tyr  Leu  Val  Pro  Ala  Thr  Cys  Lys  Ala  Ala
                       2740                      2745                      2750

Ala  Val  Leu  Gly  Met  Asp  Lys  Ala  Val  Ala  Glu  Pro  Val  Ser  Arg  Leu
                       2755                      2760                      2765

Leu  Glu  Ser  Thr  Leu  Arg  Ser  Ser  His  Leu  Pro  Ser  Arg  Val  Gly  Ala
                       2770                      2775                      2780

Leu  His  Gly  Val  Leu  Tyr  Val  Leu  Glu  Cys  Asp  Leu  Leu  Asp  Asp  Thr
        2785                      2790                      2795                      2800

Ala  Lys  Gln  Leu  Ile  Pro  Val  Ile  Ser  Asp  Tyr  Leu  Leu  Ser  Asn  Leu
                       2805                      2810                      2815

Lys  Gly  Ile  Ala  His  Cys  Val  Asn  Ile  His  Ser  Gln  Gln  His  Val  Leu
                       2820                      2825                      2830

Val  Met  Cys  Ala  Thr  Ala  Phe  Tyr  Leu  Ile  Glu  Asn  Tyr  Pro  Leu  Asp
                       2835                      2840                      2845

Val  Gly  Pro  Glu  Phe  Ser  Ala  Ser  Ile  Ile  Gln  Met  Cys  Gly  Val  Met
                       2850                      2855                      2860

Leu  Ser  Gly  Ser  Glu  Glu  Ser  Thr  Pro  Ser  Ile  Ile  Tyr  His  Cys  Ala
        2865                      2870                      2875                      2880

Leu  Arg  Gly  Leu  Glu  Arg  Leu  Leu  Leu  Ser  Glu  Gln  Leu  Ser  Arg  Leu
                       2885                      2890                      2895

Asp  Ala  Glu  Ser  Leu  Val  Lys  Leu  Ser  Val  Asp  Arg  Val  Asn  Val  His
                       2900                      2905                      2910

Ser  Pro  His  Arg  Ala  Met  Ala  Ala  Leu  Gly  Leu  Met  Leu  Thr  Cys  Met
                       2915                      2920                      2925

Tyr  Thr  Gly  Lys  Glu  Lys  Val  Ser  Pro  Gly  Arg  Thr  Ser  Asp  Pro  Asn
                       2930                      2935                      2940

Pro  Ala  Ala  Pro  Asp  Ser  Glu  Ser  Val  Ile  Val  Ala  Met  Glu  Arg  Val
        2945                      2950                      2955                      2960

Ser  Val  Leu  Phe  Asp  Arg  Ile  Arg  Lys  Gly  Phe  Pro  Cys  Glu  Ala  Arg
                       2965                      2970                      2975

Val  Val  Ala  Arg  Ile  Leu  Pro  Gln  Phe  Leu  Asp  Asp  Phe  Phe  Pro  Pro
                       2980                      2985                      2990
```

-continued

| | | | | | | | | | | | | | | |
|---|---|---|---|---|---|---|---|---|---|---|---|---|---|---|
| Gln | Asp | Ile<br>2995 | Met | Asn | Lys | Val | Ile<br>3000 | Gly | Glu | Phe | Leu | Ser<br>3005 | Asn | Gln | Gln |
| Pro | Tyr<br>3010 | Pro | Gln | Phe | Met | Ala<br>3015 | Thr | Val | Val | Tyr | Lys<br>3020 | Val | Phe | Gln | Thr |
| Leu<br>3025 | His | Ser | Thr | Gly | Gln<br>3030 | Ser | Ser | Met | Val | Arg<br>3035 | Asp | Trp | Val | Met | Leu<br>3040 |
| Ser | Leu | Ser | Asn | Phe<br>3045 | Thr | Gln | Arg | Ala | Pro<br>3050 | Val | Ala | Met | Ala | Thr<br>3055 | Trp |
| Ser | Leu | Ser | Cys<br>3060 | Phe | Phe | Val | Ser | Ala<br>3065 | Ser | Thr | Ser | Pro<br>3070 | Trp | Val | Ala |
| Ala | Ile | Leu<br>3075 | Pro | His | Val | Ile | Ser<br>3080 | Arg | Met | Gly | Lys | Leu<br>3085 | Glu | Gln | Val |
| Asp | Val<br>3090 | Asn | Leu | Phe | Cys | Leu<br>3095 | Val | Ala | Thr | Asp | Phe<br>3100 | Tyr | Arg | His | Gln |
| Ile<br>3105 | Glu | Glu | Glu | Leu | Asp<br>3110 | Arg | Arg | Ala | Phe | Gln<br>3115 | Ser | Val | Leu | Glu | Val<br>3120 |
| Val | Ala | Ala | Pro | Gly<br>3125 | Ser | Pro | Tyr | His | Arg<br>3130 | Leu | Leu | Thr | Cys | Leu<br>3135 | Arg |
| Asn | Val | His | Lys<br>3140 | Val | Thr | Thr | Cys | | | | | | | | |

That which is claimed is:

1. A purified DNA molecule comprising SEQ ID NO:7.

2. A transgenic mouse having a CAG trinucleotide repeat expansion in excess of 35 commencing at about nucleotide 169 in the translated coding region of the murine HD gene, said transgenic mouse exhibiting cognitive or motor dysfunction demonstrable by comparing said transgenic mouse to a normal control mouse in at least one test selected from the group consisting of motor activity testing, the T-maze alteration test, the radial-arm test and the Morris water maze task.

3. A targeting vector for introducing a heterologous nucleotide sequence into exon five of DNA of SEQ ID NO:7, whereby transcription of said exon is disrupted.

4. A targeting vector of claim 3 wherein said vector is pHdhneo6 and contains the neomycin resistance gene.

5. A transgenic mouse whose diploid cells contain one nucleotide sequence of SEQ ID NO:7 that has been modified by introduction of heterologous DNA within exon five of said nucleotide sequence, whereby transcription of said nucleotide sequence is disrupted so that a full-length protein product is not produced, said transgenic mouse exhibiting cognitive or motor dysfunction demonstrable by comparing said transgenic mouse to a normal control mouse in at least one test selected from the group consisting of motor activity testing, the T-maze alteration test, the radial-arm test and the Morris water maze task.

6. A transgenic mouse of claim 5 wherein said heterologous DNA contains a neomycin resistance gene.

7. A transgenic mouse of claim 5 which has a smaller volume of the subthalamic nucleus compared to a normal control mouse, said volume measured histologically or morphometrically.

8. A transgenic mouse whose diploid cells contain, within exon five of one allele of the murine HD gene, a heterologous DNA sequence that disrupts transcription of the murine HD gene, so that a full-length murine HD protein product is not produced, and wherein said transgenic mouse exhibits cognitive or motor dysfunction demonstrable by comparing said transgenic mouse to a normal control mouse in at least one test selected from the group consisting of motor activity testing, the T-maze alteration test, the radial-arm maze test and the Morris water maze task.

9. A heterozygous transgenic mouse of claim 5 or 8 which has fewer neurons in the globus pallidus compared to a normal control mouse.

10. A transgenic mouse having a trinucleotide CAG repeat expansion in excess of 35 commencing at about nucleotide 169 of the translated coding region of the murine HD gene, wherein said transgenic mouse exhibits cognitive or motor dysfunction demonstrable by comparing said transgenic mouse to a normal control mouse in at least one test selected from the group consisting of motor activity testing, the T-maze alteration test, the radial-arm maze test and the Morris water maze task.

11. A transgenic mouse whose cells contain a nucleotide sequence encoding a human huntingtin protein, said nucleotide sequence comprising a region containing more than 35 CAG trinucleotide repeats, wherein said transgenic mouse exhibits cognitive or motor dysfunction demonstrable by comparing said transgenic mouse to a normal control mouse in at least one test selected from the group consisting of motor activity testing, the T-maze alteration test, the radial-arm maze test and the Morris water maze task.

12. A DNA molecule of claim 1, further comprising additional CAG trinucleotide repeats, whereby the CAG trinucleotide repeats beginning at nucleic acid position 169 of SEQ ID NO:7 comprise more than seven CAG trinucleotide repeats.

13. A DNA molecule of claim 12 comprising at least 50 CAG trinucleotide repeats.

14. An oligonucleotide useful as an RT-PCR primer selected from the group consisting of:

MG3 (SEQ ID NO:1): GTAACACTAGGAGAATG-CAGCGAAG

MG4 (SEQ ID NO:2): GCCTTTGGTGTCTTTGTG-CAAG

MG7 (SEQ ID NO:3): GAAGGAAGGCCGTTACACAT-GCTA

MG8 (SEQ ID NO:4): CTGGGATCTGACAAGCTG-GAGGTA.

15. An oligonucleotide probe consisting of at least 18 contiguous nucleic acid residues selected from SEQ ID NO:7.

16. An isolated DNA molecule having SEQ ID NO:7.

17. A cloning vector comprising DNA of SEQ ID NO:7, wherein said DNA molecule is operatively linked to an expression control sequence.

18. A method of screening a compound for neurological effects, comprising the steps of:
   (i) behaviorally assessing a transgenic mouse according to claim 2, claim 5, claim 8, claim 10 or claim 11; and comparing said assessment to that of a normal control mouse to identify a behavioral defect in said transgenic mouse,
   (ii) administering said compound to said transgenic mouse; and
   (iii) reassessing behavior in said transgenic mouse;
wherein an amelioration of the behavioral defect identified in said transgenic mouse in step (I) following administration of said compound indicates said compound has neurological effects.

19. A method for assessing the effects of a compound on brain structure, comprising:
   (i) administering a compound to a first mouse according to claim 2, claim 5, claim 8, claim 10 or claim 11;
   (ii) sacrificing said mouse; and
   (iii) comparing brain tissue of said first mouse to brain tissue of a control mouse according to claim 2, claim 5, or claim 8 to assess the effects of said compound on brain structures.

20. A method of screening a compound for neurological effects, comprising the steps of:
   (i) obtaining a transgenic mouse according to claim 2, claim 5, claim 8, claim 10 or claim 11, said mouse having a known measurable behavioral defect compared to a normal control mouse;
   (ii) administering said compound to said transgenic mouse; and
   (iii) reassessing behavior in said transgenic mouse;
wherein amelioration of said behavioral defect following administration of said compound indicates said compound has neurological effects.

* * * * *